United States Patent
Boyes et al.

(10) Patent No.: US 7,396,468 B2
(45) Date of Patent: *Jul. 8, 2008

(54) METHODS AND SYSTEM FOR PROTEIN SEPARATION

(75) Inventors: Barry Edward Boyes, Wilmington, DE (US); James D. Martosella, Downingtown, PA (US)

(73) Assignee: Agilent Technologies, Inc., Santa Clara, CA (US)

( * ) Notice: Subject to any disclaimer, the term of this patent is extended or adjusted under 35 U.S.C. 154(b) by 55 days.

This patent is subject to a terminal disclaimer.

(21) Appl. No.: 11/404,295

(22) Filed: Apr. 14, 2006

(65) Prior Publication Data

US 2006/0186049 A1 Aug. 24, 2006

Related U.S. Application Data

(63) Continuation-in-part of application No. 11/055,260, filed on Feb. 8, 2005.

(60) Provisional application No. 60/615,176, filed on Oct. 1, 2004.

(51) Int. Cl.
    *B01D 15/08* (2006.01)
(52) U.S. Cl. ............... 210/635; 210/656; 210/198.2; 210/502.1; 530/413; 530/417
(58) Field of Classification Search ............ 210/656, 210/198.2, 502.1, 635; 530/413, 417
    See application file for complete search history.

(56) References Cited

U.S. PATENT DOCUMENTS

| | | | |
|---|---|---|---|
| 3,505,785 A | 4/1970 | Kirkland | |
| 4,070,283 A | 1/1978 | Kirkland | |
| 4,477,492 A | 10/1984 | Bergna et al. | |
| 4,847,159 A | 7/1989 | Glajch et al. | |
| 4,920,152 A * | 4/1990 | Regnier et al. | ............... 521/31 |
| 4,929,700 A | 5/1990 | Halenbeck et al. | |
| 5,108,595 A | 4/1992 | Kirkland et al. | |
| 5,439,829 A | 8/1995 | Anderson et al. | |
| 5,731,166 A | 3/1998 | Geczy et al. | |
| 5,948,531 A | 9/1999 | Kirkland et al. | |
| 5,990,284 A | 11/1999 | Mahiou et al. | |
| 6,057,468 A | 5/2000 | Kirkland et al. | |
| 6,538,126 B1 | 3/2003 | Cho et al. | |
| 6,730,228 B2 | 5/2004 | Petro et al. | |
| 6,866,782 B2 | 3/2005 | Scapol et al. | |
| 2002/0035241 A1 | 3/2002 | Buchacher et al. | |

(Continued)

FOREIGN PATENT DOCUMENTS

WO  WO 02/055654  7/2002

(Continued)

OTHER PUBLICATIONS

High Velocity Chromatography of Biomacromolecules, Brian A. Bidlingmeyer and Robert D. Ricker, Copyright 2001.

(Continued)

*Primary Examiner*—Ernest G Therkorn

(57) ABSTRACT

The present disclosure relates to a system and method for membrane protein separation including: fractionating a membrane sample on a reversed-phase superficially porous stationary phase at a temperature of greater than or equal to about 40° C. to recover a protein greater than about 70 weight percent of the mixture of proteins.

19 Claims, 24 Drawing Sheets

U.S. PATENT DOCUMENTS

| | | | |
|---|---|---|---|
| 2002/0168682 A1* | 11/2002 | Goodlett et al. | 435/7.1 |
| 2003/0010715 A1 | 1/2003 | Scapol et al. | |
| 2003/0027354 A1* | 2/2003 | Geli | 436/178 |
| 2003/0229212 A1 | 12/2003 | Fahmer et al. | |
| 2004/0115725 A1 | 6/2004 | Pieper et al. | |
| 2004/0200776 A1* | 10/2004 | Ivanov et al. | 210/656 |
| 2006/0240633 A1 | 10/2006 | Martosella et al. | |

FOREIGN PATENT DOCUMENTS

| | | |
|---|---|---|
| WO | WO 2004/035169 | 4/2004 |

OTHER PUBLICATIONS

A family of superficially porous particle HPLC columns for versatility in the rapid analysis of proteins and polypeptides at low and high pH, Robert D. Ricker, Wu Chen, Bernard J. Permar, and Cliff Woodward, HPLC 2004, Philadelphia, PA, Wed.-Jun. 16, 2004, Poster P-1020.

High velocity chromatography A new technique for macromolecule separation, R.D. Ricker, B.J. Permar, and B.A. Bidlingmeyer Life Science and Chemical Analysis Group, Talk # 763, Presented at Pittcon 2002, Mar. 17-21, New Orleans, LA, USA.

Fast Separation of Large and Heterogeneous Proteins Using ZORBAX Poroshell C18, C8, and C3 Phases, Cliff Woodward and Robert D. Ricker, Agilent Technologies, Inc. 2003, Printed in the USA, Oct. 17, 2003.

Comparison of ZORBAX Poroshell 300Extend-C18 and Totally Porous Packing in Achieving Very Rapid, High-pH Separation of Peptides, Biotechnology/QA/QC/Basic R&D, Robert Ricker, Agilent Technologies, Inc., 2004, Printed in the USA, Feb. 20, 2004.

Ultrafiltration for proteomic sample separation, Elena Chernokalskaya, Sara Gutierrez, Aldo M. Pitt, and Jack T. Leonard, Millipore Corporation, Life Science Division, Danvers, MA USA, Electrophoresis 2004, 25, 2461-2468.

H. Liu, R. Sadygov, and J.R. Yates, III, A Model for Random Sampling and Estimation of Relative Protein Abundance in Shotgun Proteomics, Analytical Chemistry, vol. 76, No. 14, Jul. 15, 2004, pp. 4193-4201.

P. Girogion Righetti, A. Castagna, B. Herbert, F. Reymond, and J. Rossier, Prefractionation techniques in proteoma analysis, Proteomics 2003, 3, 1397-1407. DOI 10.1002/pmic.200300472. 2003 Wiley-VCH Verlad GmbH & Co. KGaA, Weinheim.

HPLC 2004, Philadelphia, PA, Wed.-Jun. 16, 2004, Poster P-1020. Reversed-phase high-performance liquid chromatography prefractionation prior to two-dimensional difference gel electrophoresis and mass spectrometry identifies new differentially expressed proteins, between striate cortex of kitten and adult cat, Electrophoresis 2003, 24, 1471-1481. 2003 Wiley-VCH Verlag GmbH & Co. KGaA, Weinham.

Neverova, I. and J.E. Van Eyk, Application of reversed phase high performance liquid chromatography for subproteomic analysis of cardiac muscle. Proteomics 2002. 2(1): p. 22-31. Wiley-VCH Verland GmbH, 69451 Weinheim, 2002.

Lescuyer, P., D.F. Hochstrasser, and J.C. Sanchez, Comprehensive proteome analysis by chromatographic protein prefractionation. Electrophoresis, 2004. 25(7-8): p. 1125-1135. Wiley-VCH Verlag GmbH & Co. KGaA, Weinheim.

J. Martosella, N. Zolotarjova, G. Nicol, C. Miller, R. Ricker, H. Liu, and B. Boyes, Optimization of Reversed-Phase Separations of Human Serum Proteins and Use in Proteins Identification Human Serum Proteins and Use in Protein Identification Agilent Technologies, Wilmington DE 19808; ASMS 2004 ThPF483.

James Martosella, Nina Zolotarjova, Hongbin Liu, Gordon Nicol, and Barry E. Boyes; Reversed-Phase High-Performance Liquid Chromatographic Prefractionation of Immunodepleted Human Serum Proteins to Enhance Mass Spectrometry Identification of Lower-Abundant Proteins: Agilent Technologies, Wilmington DE 19808; Journal of Proteome Research 2005, 4, 1522-1537; published Aug. 4, 2005.

F. Elortza, T.S. Nuhse, L.J. Foster, A. Stensballe, S.C. Peck, and O.N. Jensen; Proteomic Analysis of Glycosylphosphatidylinositol-anchored Membrane Proteins, The American Society for Biochemistry and Molecular Biology, Inc. © 2003; Molecular & Cellular Proteomics 2.12, 1261-1270.

L.A. Eichacker, B. Granvoigl, O. Mirus, B.C. Muller, C.Miess, and E. Schleiff; Hiding behind Hydrophobicity Department fur Biologie I, Ludwig=Masimilians Universitat Muchen, Muchen, Germany and Hoffmann-La Roche, Roche Centre for Medical Geomics, Basel, Switzerland; Journal of Biological Chemistry © 2004 by the American Society for Biochemistry and Molecular Biology, Inc., vol. 279, No. 49, Issue of Dec. 3, pp. 50915-50922, 2004.

Jun Han and Kevin L. Schey; Proteolysis and Mass Spectrometric Analysis of an Integral Membrane: Aquaporin 0; Deptartment of Cell and Molecular Pharmacology, Medical University of South Carolina, Charleston, SC; Journal of Proteome Research, 2004, 3, 807-812; © 2004 American Chemical Society, published on the web May 19, 2004.

T.J. Nuhse, A. Stensballe, O.N. Jensen, and S.C. Peck; Large-scale Analysis of in Vivo Phosphorylated Membrane Proteins by Immobilized Metal Ion Affinity Chromatography and Mass Spectrometry; © 2003 by The American Society for Biochemistry and Molecular Biology, Inc.; Molecular & Cellular Proteomics 2.11, pp. 1234-1243.

Agnew et al., 2004, "A rapid solid-phase fluorescence-based protein assay for quantitation of protein electrophoresis samples containing detergents, chaotropes, dyes, and reducing agents", *Electrophoresis*, 25(15):2478-2485.

Albouz-Abo et al., "A conformational study of the human and rat encephalitogenic myelin oligodendrocyte glycoprotein peptides", *Eur. J. Biochem.*, 246:59-70 (1997).

Antia et al., 1988, "High-Performance liquid chromatography at elevated temperatures: examination of conditions for the rapid separation of large molecules", *Journal of Chromatography A*, 435:1-15.

Badock et al., 2001, "Prefractionation of protein samples for proteome analysis using reversed-phase high-performance liquid chromatography", *Electrophoresis*, 22(14):2856-2864.

Becher et al., "Eptopically expressed -aminobutyric acid receptor B is functionally down-regulated in isolated lipid raft-enriched membranes", Biochemical and Biophysical Research Communications, 321:981-987 (2004).

Becher et al., "The -aminobutyric acid receptor B, but not the metabotropic glutamate receptor type-1, associates with lipid rafts in the rat cerebellum", *Journal of Neurochemistry*, 79:787-795 (2001).

Bhardwaj et al., 1997, "Detection of Intra-Cellular Protein-Protein Interactions: Penicillin Interactive Proteins and Morphogene Proteins", *Techniques in Protein Chemistry VIII*, p. 469-480.

Bhardwaj et al., 1999, "Trifluoroethanol Removes Bound Proteins from Reversed-Phase Columns", *LC-GC*, 17(4):354-355.

Biel et al., "Tissue-specific expression of high-voltage-activated dihydropyridine-sensitive L-type calcium channels", *Eur. J. Biochem.*, 200:81-88 (1991).

Bledi et al., "Proceed: A proteomic method for analyzing plasma membrane proteins in living mammalian cells", *Briefings in Functional Genomics & Proteomics*, 2, 3, Research Library (2003).

Blonder et al., "Enrichment of Integral Membrane Proteins for Proteomic Analysis Using Liquid Chromatography-Tandem Mass Spectrometry", Journal of Proteome Research, 1:351-360 (2002).

Bruins et al., 1987, "Ion Spray Interface for Combined Liquid Chromatography/Atmospheric Pressure Ionization Mass Spectrometry", *Anal Chem.*, 59: 2642-2647.

Castro et al., "Lipid Removal from Human Serum Samples", *Clinical and Diagnostic Laboratory Immunology*, 7(2):197-199 (Mar. 2000).

Chen et al., 2003, "Temperature selectivity effects in reversed-phase liquid chromatography due to conformation differences between helical and non-helical peptides", *J Chromatogr A*, 1010(1): 45-61.

Cohen et al., 1984, "Mobile-phase and temperature effects in the reversed phase chromatographic separation of proteins", *Anal. Biochem.*, 140(1):223-235.

Duan et al., 2004, "A mouse serum two-dimensional gel map: Application to profiling burn injury and infection", *Electrophoresis*, 25(17):3055-3065.

Fenn et al., 1989, "Electrospray Ionization for Mass Spectrometry of Large Biomolecules", *Science*, 246: 64-71.

Figeys et al., "Optimization of solid phase microextraction—capillary zone electrophoresis—mass spectrometry for high sensitivity protein identification", 1998, *Electrophoresis*, 19: 2338-2347.

Foster et al., "Unbiased quantitative proteomics of lipid rafts reveals high specificity for signaling factors", *Proceedings of the National Academy of Sciences of the United States of America*, 100(10):5813-5818 (May 13, 2003).

Fujii et al., 2004, "Multidimensional protein profiling technology and its application to human plasma proteome", *J Proteome Res.*, 3(4):712-718.

Galmarini et al., "Multidrug resistance in cancer therapy: Role of the microenvironment", Current Opinion in Investigational Drugs, 4(12):1418-1421 (2003).

Goshe et al., "Affinity Labeling of Highly Hydrophobic Integral Membrane Proteins for Proteome-Wide Analysis", Journal of Proteome Research, 2:153-161 (2003).

Griffiths, "Tandem Mass Spectrometry in the Study of Fatty Acids, Bile Acids and Steriods", Mass Spectrometry Reviews, 22:81-152 (2003).

Guillarme et al., 2004, "Effect of temperature in reversed phase liquid chromatography", *J. Chromatogr., A*, 1052(1-2):39-51.

Heukeshoven et al., "Reversed-Phase High-Performance Liquid Chromatography of Virus Proteins and Other Large Hydrophobic Proteins in Formic Acid Containing Solvents", Journal of Chromatography, 252:241-254 (1982).

Hsu et al., "Electrospray ionization/Tandem Quadrupole Mass Spectrometric Studies on Phosphatidylcholines: The Fragmentation Processes", *J. Am. Soc. Mass Spectrom*, 14:352-363 (2003).

Isaac et al., "Analysis of phosphatidylcholine and sphingomyelin molecular species from brain extracts using capillary liquid chromatography electrospray ionization mass spectrometry", Journal of Neuroscience Methods, 128:111-119 (2003).

Jack, G.W., 1994, "Immunoaffinity Chromatography", *Mol. Biotech*, 1:59-86.

Janini et al., 2004, "Two-dimensional liquid chromatography-capillary zone electrophoresis-sheathless electrospray ionization-mass spectrometry: evaluation for peptide analysis and protein identification", *Electrophoresis*, 25(13):1973-1980.

Josic et al., "Use of selective extraction and fast chromatographic separation combined with electrophoretic methods for mapping of membrane proteins", *Electrophoresis*, 26:2809-2822 (2005).

Kalghatgi et al., 1987, "Rapid analysis of proteins and peptides by reversed-phase chromatography", *J. Chromatogr.*, 398:335-339.

Karsan et al., "Proteomic Analysis of Lipid Microdomains from Lipopolysaccharide-Activated Human Endothelial Cells", Journal of Proteome Research, 4:349-357 (2005).

Lee et al., "Purification of hydrophobic integral membrane proteins from Mycoplasma hyopneumoniae by reversed-phase high-performance liquid chromatography", Journal of Chromatography A, 737:273-279 (1996).

Lee et al., 2004, "Applications of affinity chromatography in proteomics", *Anal BioChem.*, 324:1-10.

Lee et al., 2004, "Optimization of reversed-phase microcapillary liquid chromatography for quantitative proteomics", *J Chromatogr B Analyt Technol Biomed Life Sci*, 803(1):101-110.

Licklider et al., 2000, "A Micromachined Chip-Based Electrospray Source for Mass Spectrometry", *Anal. Chem.*, 72: 367-375.

Maa et al., 1988, "Rapid analysis of proteins and peptides by reversed-phase chromatography with polymeric micropellicular sorbents", *Journal of Chromatography A*, 445:71-86.

Maine et al., "Measles Virus Structural Components Are Enriched into Lipid Raft Microdomains: a Potential Cellular Location for Virus Assembly", *Journal of Virology*, 74(1):305-311 (Jan. 2000).

Marshall et al., 2004, "Human serum proteins preseparated by electrophoresis or chromatography followed by tandem mass spectrometry", *J Proteome Res*, 3(3):364-382.

Martosella, "Reversed-Phase High-Performance Liquid Chromatographic Prefraction of Immunodepleted Human Serum Proteins to Enhance Mass Spectrometry Identification of Lower Abundant Proteins", *Journal of Proteome Research*, 4:1522-1537 (2005).

Mastro et al., "Protein Delipidation and Precipitation by Tri-n-butylphosphate, Acetone, and Methanol Treatment for Isoelectric Focusing and Two-Dimensional Gel Electrophoresis", Analytical Biochemistry, 273:313-315 (1999).

McDonald et al., "Comparison of three directly coupled HPLC MS/MS strategies for identification of proteins from complex mixtures: single-dimension LC-MS/MS, 2-phase MudPIT, and 3-phase MudPIT", International Journal of Mass Spectrometry, 219:245-251 (2002).

Meza et al., "Improved Tryptic Digestion of Proteins Using 2,2,2-Trifluoroethanol (TFE)", Agilent Technologies, Poster-ABRF (2004).

Mikol et al., "A Phosphatidylinositol-linked Peanut Agglutinin-binding Glycoprotein in Central Nervous System Myelin and on Oligodendrocytes", *The Journal of Cell Biology*, 106:1273-1279 (Apr. 1988).

Moffatt et al., 2000, "Approaches towards the quantitative analysis of peptides and proteins by reversed-phase high-performance liquid chromatography in the absence of a pure reference sample", *J Chromatogr A*, 891(2):235-242.

Nebl et al., "Proteomic Analysis of a Detergent-resistant Membrane Skeleton form Neutrophil Plasma Membranes", *The Journal of Biological Chemistry*, 277(45):43399-43409 (Nov. 8, 2002).

Oh et al., "Segregation of Heterotrimeric G Proteins in Cell Surface Microdomains", *Molecular Biology of the Cell*, 12:685-698 (Mar. 2001).

Oh-Ishi et al., "Separation techniques for high-molecular-mass proteins", Journal of Chromatography B, 771:49-66 (2002).

Pike, "Lipid rafts: bringing order to chaos", *Journal of Lipid Research*, 44:655-667 (2003).

Pike, "Lipid rafts: heterogeneity on the high seas", *Biochem. J.*, 378:281-292 (2004).

Rahbar et al., "Unbiased Examination of Changes in Plasma Membrane Proteins in Drug Resistant Cancer Cells", Journal of Proteome Research, 4:2148-2153 (2005).

Riddell et al., "Compartmentalization of -secretase (Asp2) into low-buoyant density, noncaveolar lipid rafts", *Current Biology*, 11:1288-1293 (2001).

Rose et al., 2004, "Industrial-scale proteomics: from liters of plasma to chemically synthesized proteins", *Proteomics*, 4(7):2125-2150.

Scherer et al., 1999, "Ultra-high throughput rotary capillary array electrophoresis scanner for fluorescent DNA sequencing and analysis", *Electrophoresis*, 20: 1508-1517.

Schluesener et al., "Mapping the membrane proteome of *Cornyebacterium glutamicum*", Proteomics, 5:1317-1330 (2005).

Simons et al., "Functional rafts in cell membranes", Nature, 387:569-572 (Jun. 5, 1997).

Simons et al., "Lipid Rafts and Signal Transduction", Nature Reviews/Molecular Cell Biology, 1:31-39 (Oct. 2000).

Slaughter et al., "The flotillins are integral membrane proteins in lipid rafts that contains TCR-associated signaling components: Implications for T-cell activation", Clinical Immunology, 108:138-151 (2003).

Szafranski et al., 2004, "Enhancing Analytical Access to Low-abundant Proteins in the Human Plasma Proteome", *Pharmagenomics*, pp. 40-46.

Tirumalai et al., 2003, "Characterization of the low molecular weight human serum proteome", *Mol Cell Proteomics*, 2(10):1096-1103.

Tu et al., "Proteome Analysis of Lipid Rafts in Jurkat Cells Characterizes a Raft Subset that is Involved in NF-K B Activation", Journal of Proteome Research, 3:445-454 (2004).

Welling et al., "Column Liquid Chromatography of Integral Membrane Proteins", Journal of Chromatography, 418:223-243 (1987).

Whitelegge et al., "Electrospray-ionization mass spectrometry of intact intrinsic membrane proteins", *Protein Science*, 7, 1423-1430, Cambridge University Press (1998).

Whitelegge et al., "Full Subunit Coverage Liquid Chromatography Electrospray Ionization Mass Spectrometry (LCMS+) of an Oligomeric Membrane Protein", *Molecular & Cellular Proteomics* 1.10, 816-827 (2007).

Whitelegge et al., "Proteomics of Membrane Proteins", Advances in Protein Chemistry, 65:271-307 (2003).

Whitelegge et al., Sequence analysis of photoaffinity-labelled peptides derived by proteolysis of photosystem-2 reaction centres from thylakoid membranes treated with [14C]azidoatrazine, *Eur. J. Biochem.*, 207:1077-1084 (1992).

Whitelegge et al., "Tandem mass spectrometry of integral membrane proteins for top-down proteomics", Trends in Analytical Chemistry, 24(7):576-582 (2005).

Williams et al., "Structure and Functional Express of a1, 1s and Subunits of a Novel Human Neuronal Calcium Channel Subtype", Neuron, 8:71-84 (Jan. 1992).

Zeeberg et al., "GoMiner: a resource for biological interpretation of genomic and proteomic data", *Genome Biology*, vol. 4, Issue 4, Article R28, R28.1-R28.8 (2003).

Zubritsky et al., 2000, "Multisample nanoelectrospray", *Anal. Chem.*, 72:22A.

Huang et al., "Applications of Preparative High-Performance Liquid Chromatography to the Separation and Purification of Peptides and Proteins", *J. of Chromatography*, 492:431-469 (1989).

Hage, "Survey of recent advances in analytical applications of immunoaffinity chromatography", *J. of Chromatography B*, 715:3-28 (1998).

Hage, "Affinity Chromatography: A Review of Clinical Applications", *Clinical Chemistry*, 45(5):593-615 (1999).

Communication dated Nov. 23, 2006 enclosing the EP Search Report for EP Application No. 05255933.3 dated Nov. 9, 2006, and Annex to the EP Search Report, 4 pp. —Counterpart of U.S. Appl. No. 11/055,260.

* cited by examiner

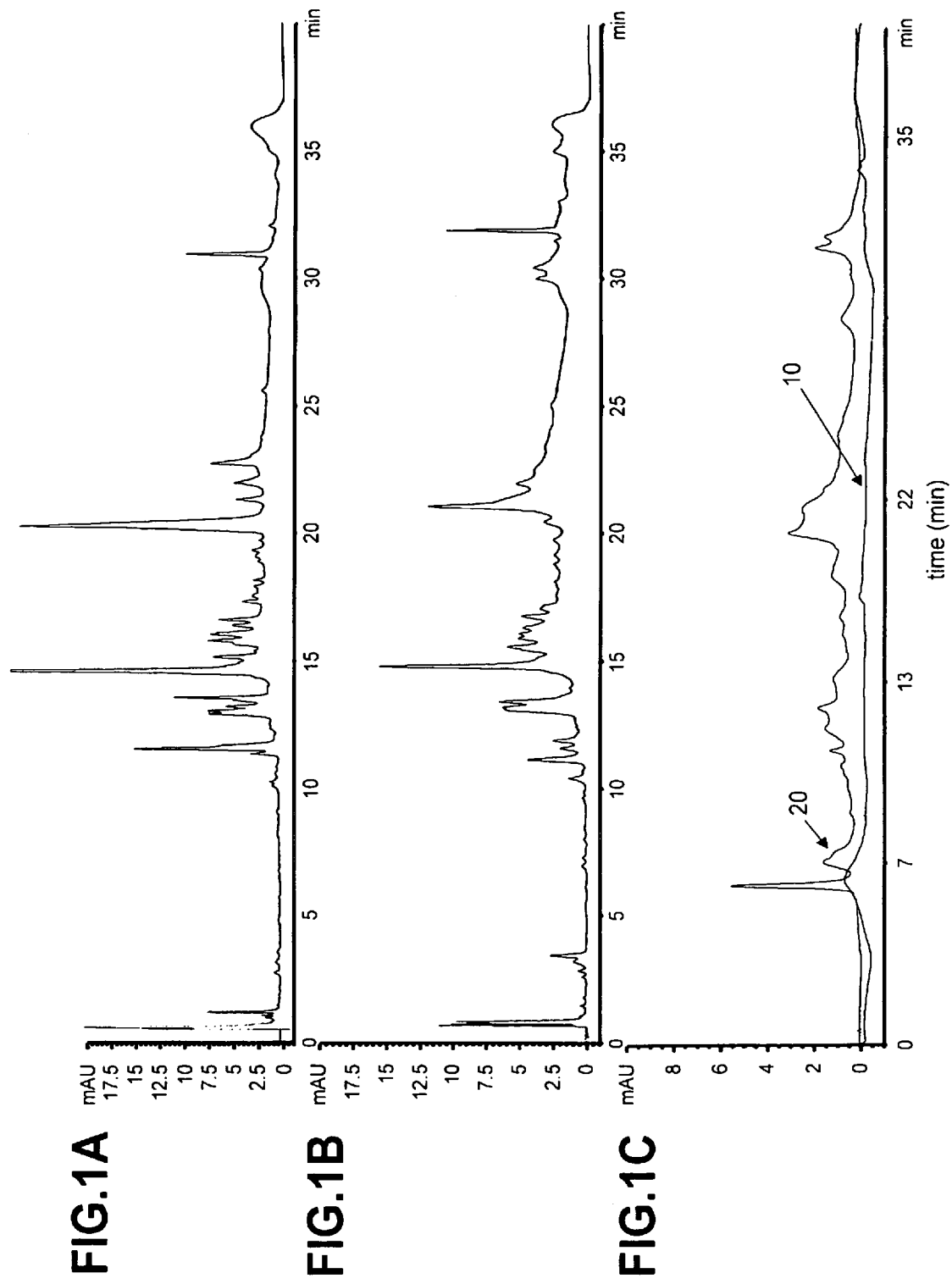

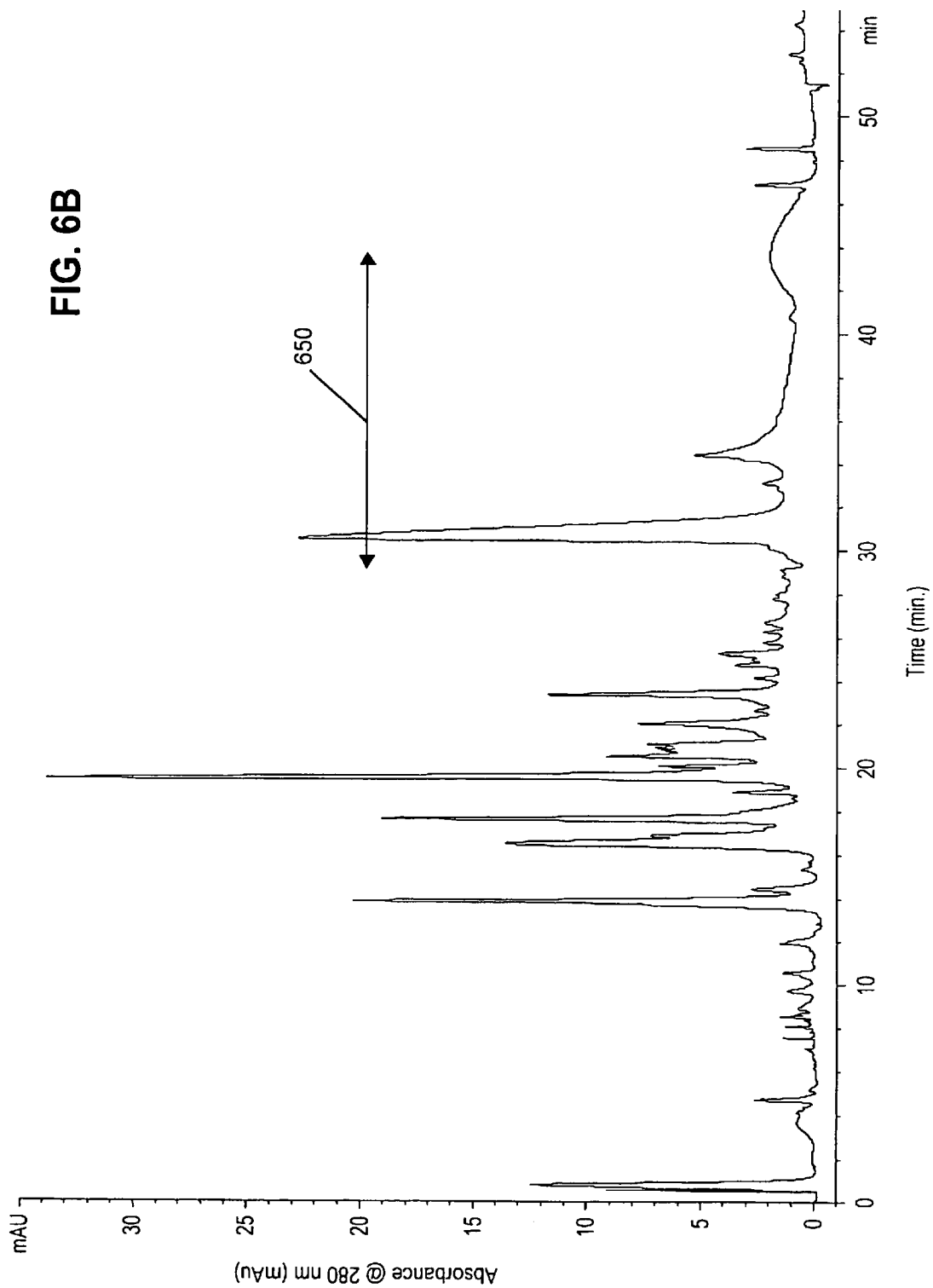

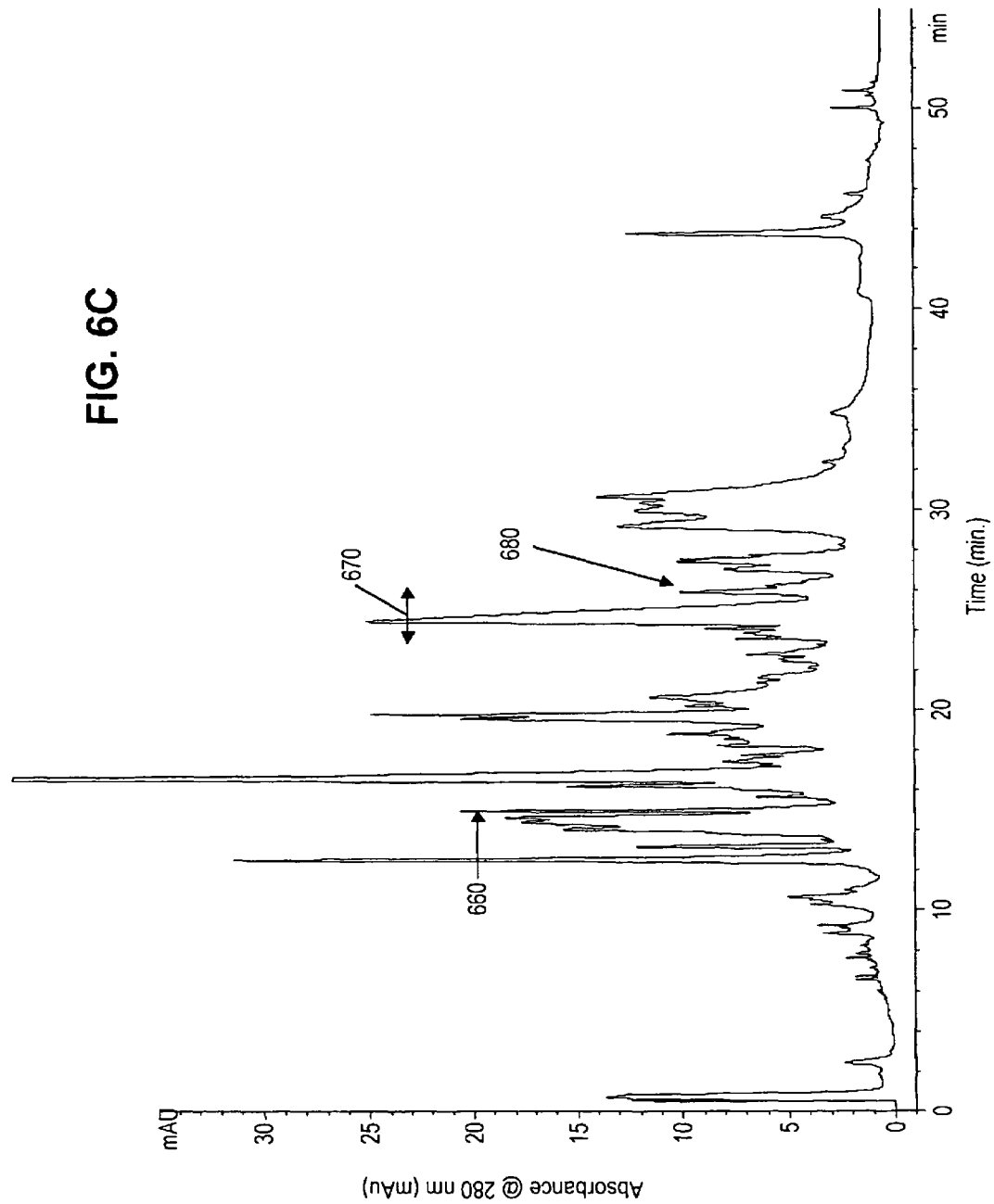

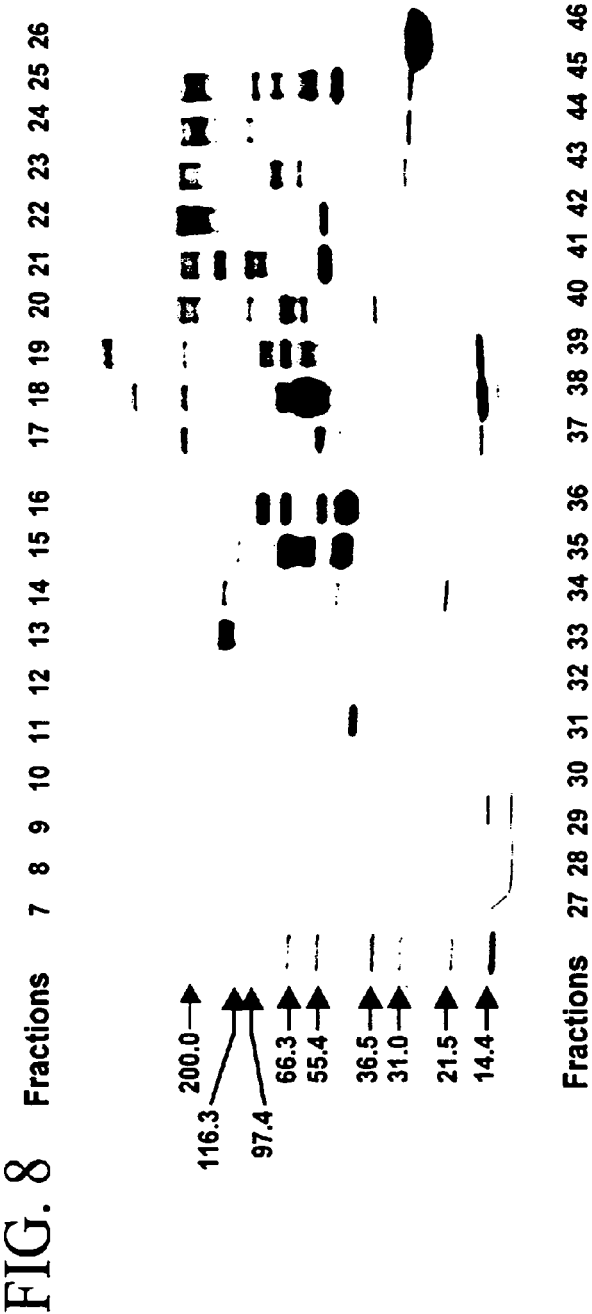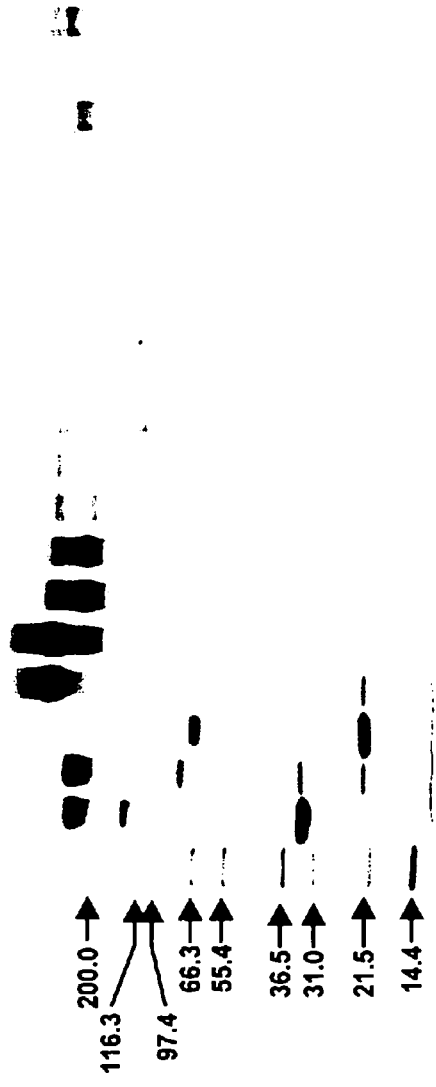
FIG. 8

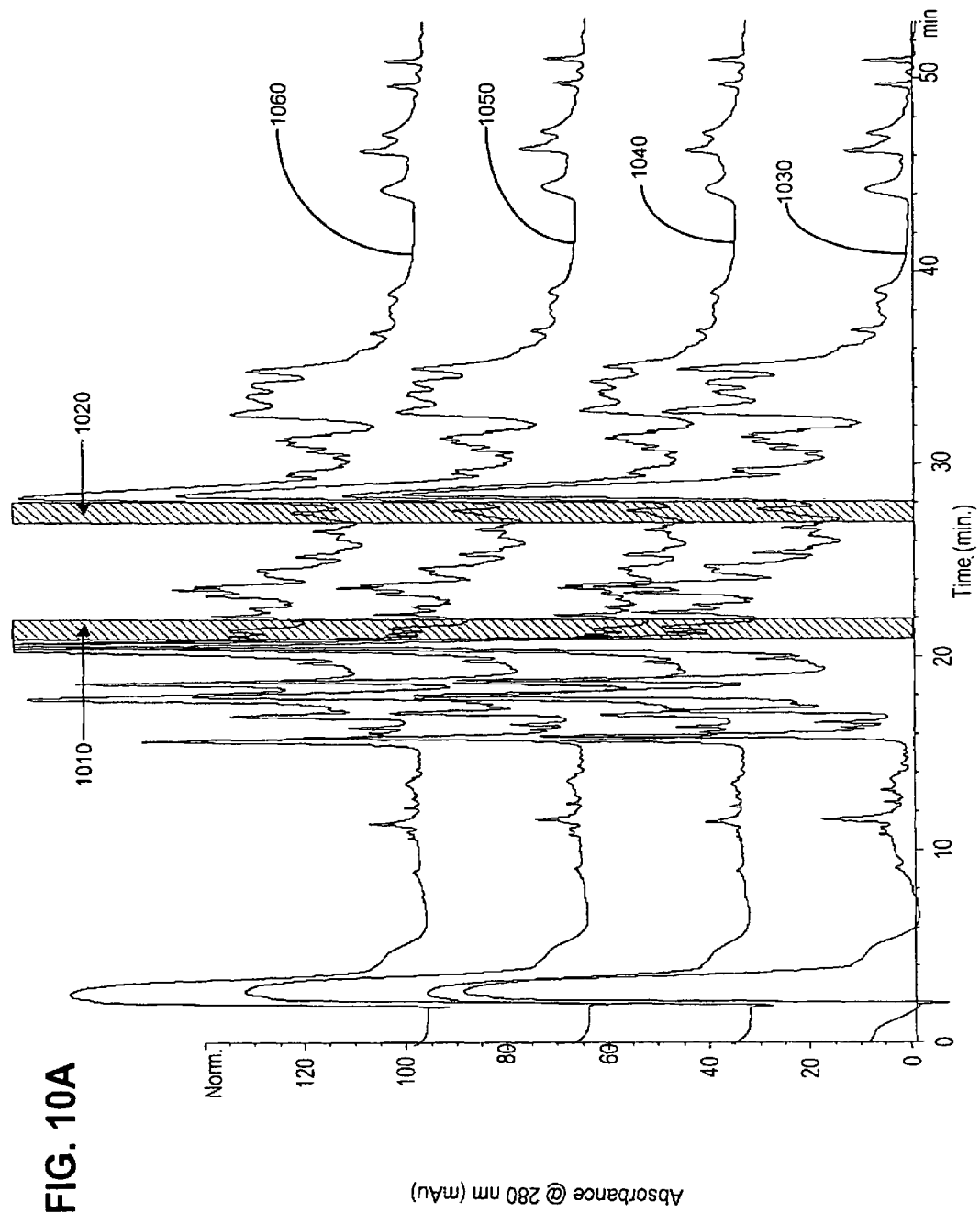

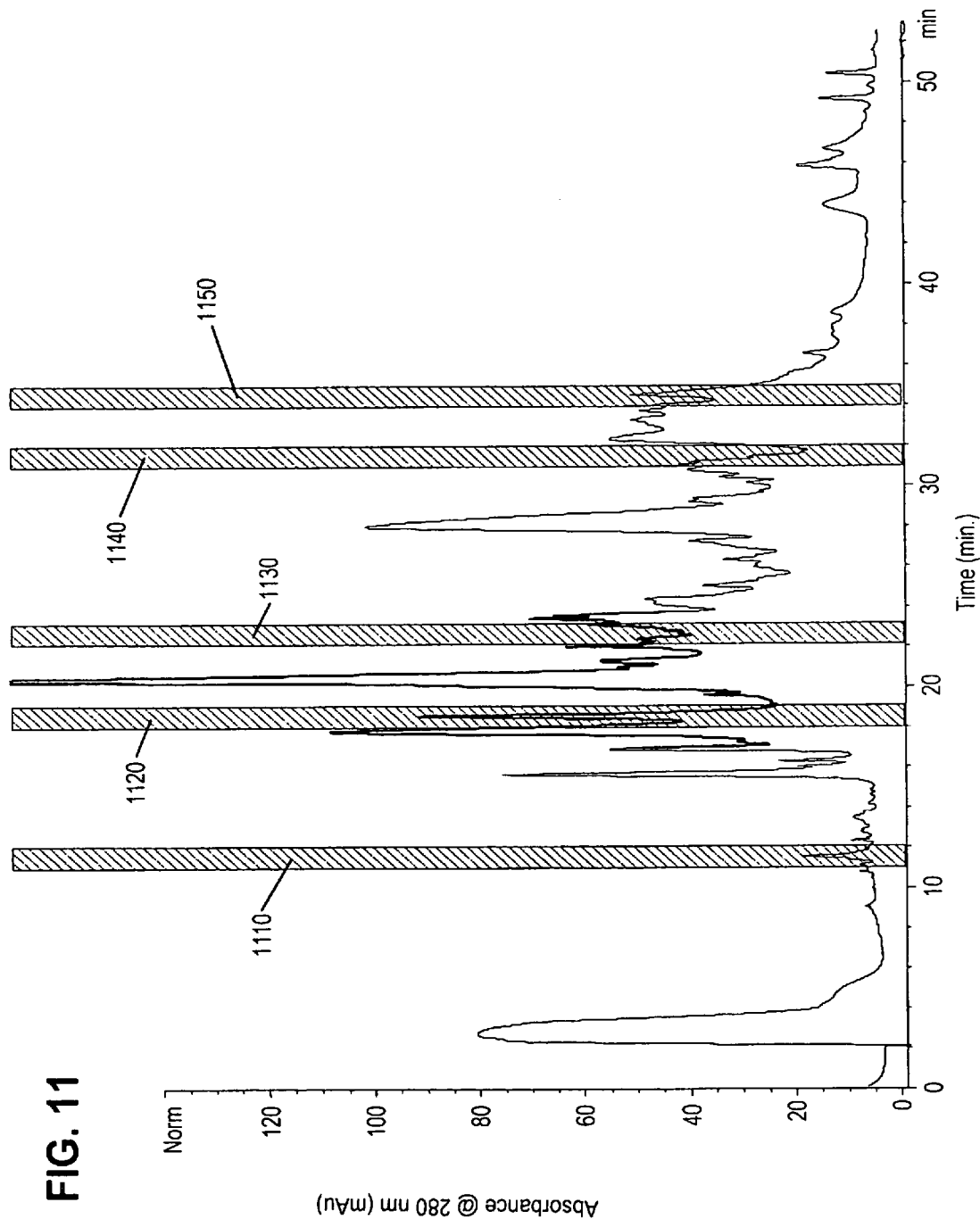

METHODS AND SYSTEM FOR PROTEIN SEPARATION

REFERENCE TO RELATED APPLICATIONS

This application is a U.S. continuation-in-part application and is related to and claims priority to U.S. application Ser. No. 11/055,260, filed Feb. 8, 2005, which claims priority to U.S. provisional application Ser. No. 60/615,176, filed Oct. 1, 2004, the disclosure of which is incorporated herein by reference in its entirety.

BACKGROUND

Interest in proteomic analysis of human serum has been greatly elevated during the past several years. Proteomic analysis of human serum represents an extreme challenge due to the dynamic range of the proteins of interest. In serum, the quantities of proteins and peptides of interest range from those considered "high abundance", present at 2-50% by mass of total protein, to those present at $10^{-12}$ or less. This range of analytical target molecules is outside the realm of available technologies for proteomic analysis. One way to address the complexity of these samples is the application of multidimensional separation techniques.

At present, two major approaches are being used as pre-fractionation techniques: chromatographic and electrophoretic. Liquid chromatography equipment and methods, such as high-performance liquid chromatography (HPLC), can be used in a variety of applications, such as, for example, in chemical analysis or diagnostics, to separate, isolate, and identify chemical compounds in mixtures. A significant problem encountered in liquid chromatographic methods is the lack of methods to reliably separate, detect, or distinguish low abundance protein constituents from high abundance protein constituents in a sample of interest. Consequently, lower abundance proteins, for example, of significant biological interest, can be incompletely detected or can go undetected or overlooked. Additionally, recovery of proteins from currently used HPLC columns is often unsatisfactory for proteomic analysis since lower abundance proteins may be present at concentrations that are at or below the detection limits of conventional instrumentation used in proteomic analysis (e.g., such as mass spectrometers).

SUMMARY

The present disclosure generally relates to methods and systems for separating biopolymers such as proteins, polypeptides, peptides, polynucleotides, their chemical synthetic or biosynthetic equivalents, and like polymers, or combinations thereof. In one aspect, the disclosure provides a method of protein separation, comprising: fractionating a membrane sample on a superficially porous stationary phase at elevated temperature (e.g., greater than about 39° C.). The method may comprise reversed phase high pressure liquid chromatography (RP-HPLC). In another aspect, the disclosure provides a method of protein separation comprising: fractionating a membrane sample on a superficially porous phase at a temperature of, for example, greater than about 40° C., such as from about 40 to about 95° C., or from about 60 to about 95° C. In another aspect, the recovery of separated proteins increases with increasing temperature. In still another aspect, the disclosure provides methods and systems for separating biopolymers which can further include additional processing steps, before or after the reversed phase chromatography, and as illustrated herein.

BRIEF DESCRIPTION OF THE DRAWINGS

FIGS. 1A-1C illustrates protein separations, recoveries and resolutions of the present method compared to an alternative method, in embodiments of the present disclosure.

FIG. 6A-6C illustrate the effect of temperature on chromatographic separation using a 3-step gradient, in embodiments of the present disclosure.

FIG. 8 illustrates an SDS-PAGE analysis of HPLC fractionated immunodepleted human serum from a reversed-phase macroporous column, in embodiments of the present disclosure.

FIG. 10A-10B illustrate a composite overlay of chromatograms from four reversed-phase separations of immunodepleted human serum on a macroporous column, in embodiments of the present disclosure, and a 1-D gel analysis of selected fractions from a reversed-phase separation, respectively, in embodiments of the present disclosure.

FIG. 11 illustrates a macroporous RP-HPLC immunodepleted human serum separation under gradient conditions, in embodiments of the present disclosure.

DETAILED DESCRIPTION

Figures 2A, 2B:
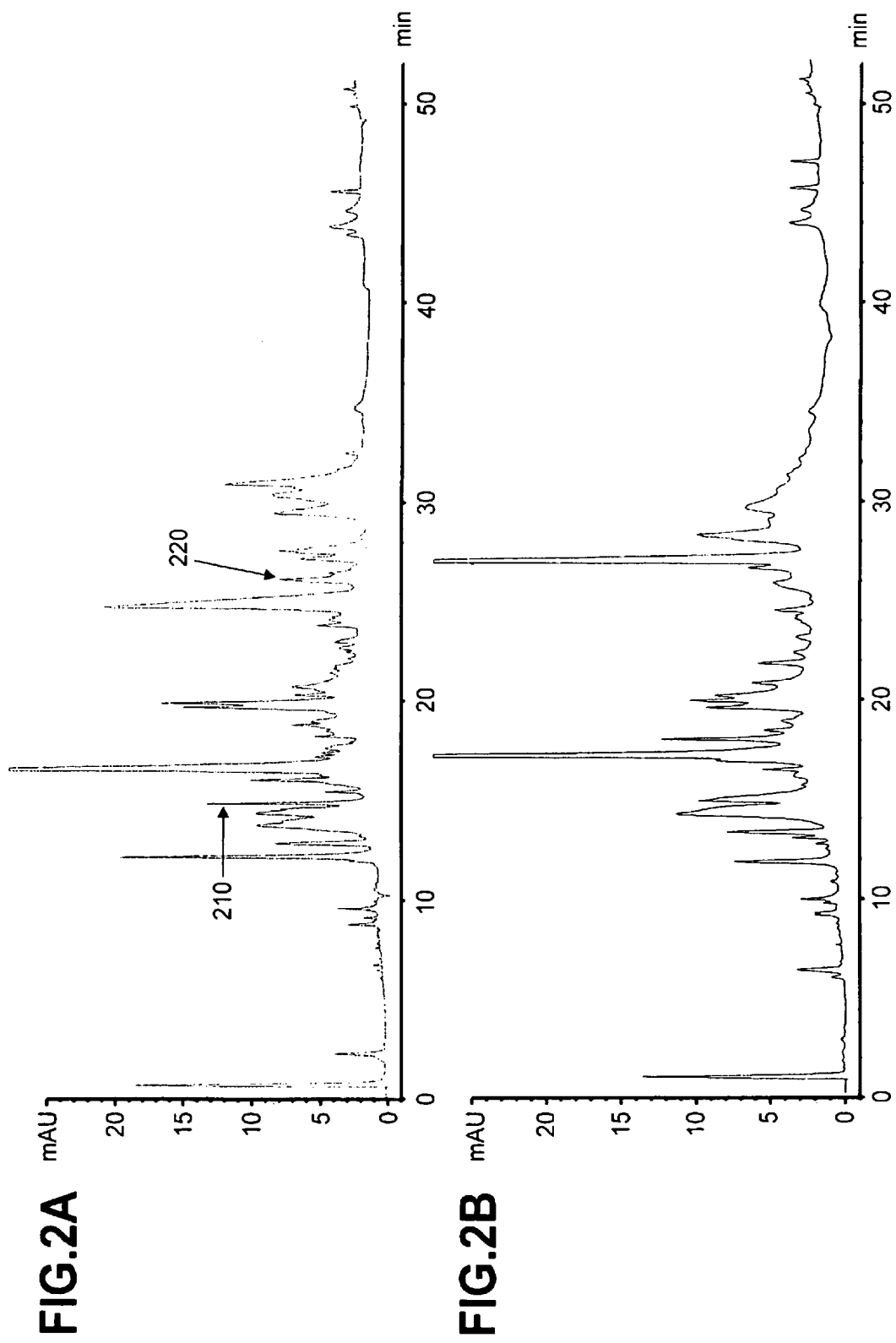
FIG. 2A-2B further illustrates protein separations, separation selectivities, and resolutions of the present method compared to an alternative method, in embodiments of the present disclosure.

Various embodiments of the present disclosure will be described in detail with reference to drawings, if any. Reference to various embodiments does not limit the scope of the disclosure, which is limited only by the scope of the claims attached hereto. Additionally, any examples set forth in this specification are not intended to be limiting and merely set forth some of the many possible embodiments for the claimed invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present disclosure, the preferred methods and materials are now described. Methods recited herein may be carried out in any order that is logically possible, in addition to a particular order disclosed.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

The practice of the present disclosure will employ, unless otherwise indicated, conventional techniques of chemistry, biochemistry, molecular biology, and medicine, including diagnostics, which are within the skill of the art. Such techniques are explained fully in the literature.

The following definitions are provided for specific terms that are used in the following written description.

It must be noted that as used herein and in the appended claims, the singular forms "a", "and", and "the" include plural referents unless the context clearly dictates otherwise. Thus, for example, reference to "a protein" includes a plurality of such proteins and reference to "protein" includes reference to one or more proteins and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that can occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

Where a range of values is provided, it is understood that each intervening value, to the tenth of the unit of the lower limit unless the context clearly dictates otherwise, between the upper and lower limit of that range and any other stated or intervening value in that stated range is encompassed within the disclosure. The upper and lower limits of these smaller ranges may independently be included in the smaller ranges is also encompassed within the disclosure, subject to any specifically excluded limit in the stated range. Where the stated range includes one or both of the limits, ranges excluding either both of those included limits are also included in the disclosure.

A "set" or "sub-set" of any item (such as a set of proteins or peptides) may contain only one of the item, or only two, or three, or any multiple number of the items.

As used herein, a "peptide mixture" is typically a complex mixture of peptides obtained as a result of the cleavage of a sample comprising proteins.

As used herein, a "sample of proteins" is typically any complex mixture of proteins and/or their modified and/or processed forms, which may be obtained from sources, including, without limitation: a cell sample (e.g., lysate, suspension, collection of adherent cells on a culture plate, a scraping, a fragment or slice of tissue, a tumor, biopsy sample, an archival cell or tissue sample, laser-capture dissected cells, etc), an organism (e.g., a microorganism such as a bacteria or yeast), a subcellular fraction (e.g., comprising organelles such as nuclei or mitochondria, large protein complexes such as ribosomes or golgi, and the like), an egg, sperm, embryo, a biological fluid, viruses, and the like.

The term "peptide" as used herein refers to an entity comprising at least one peptide bond, and can comprise either D and/or L amino acids. A peptide can have, for example, about 2 to about 20 amino acids (e.g., about 2, 3, 4, 5, 6, 7, 8, 9, or 10 amino acids).

"Protein", as used herein, means any protein, including, but not limited to peptides, enzymes, glycoproteins, hormones, receptors, antigens, antibodies, growth factors, etc., without limitation. Proteins include those comprised of greater than about 20 amino acids, greater than about 35 amino acid residues, or greater than about 50 amino acid residues.

The terms "peptide," "polypeptide," and "protein" are generally used interchangeably herein.

As used herein, "a biological fluid" includes, but is not limited to, blood, plasma, serum, sputum, urine, tears, saliva, sputum, cerebrospinal fluid, lavages, leukapheresis samples, milk, ductal fluid, perspiration, lymph, semen, umbilical cord fluid, and amniotic fluid, as well as fluid obtained by culturing cells, such as fermentation broth and cell culture medium.

As used herein, "a sample of complex proteins" may contain greater than about 100, about 500, about 1,000, about 5,000, about 10,000, about 20,000, about 30,000, about 100,000 or more different proteins. Such samples may be derived from a natural biological source (e.g., cells, tissue, bodily fluid, soil or water sample, and the like) or may be artificially generated (e.g., by combining one or more samples of natural and/or synthetic or recombinant sources of proteins).

As used herein, "a membrane sample" is a sample of proteins including membrane components such as membrane-associated proteins and lipids (i.e. phospholipids). Membrane-associated proteins includes extrinsic or peripheral proteins and intrinsic proteins, including receptor proteins and cell adhesion proteins, as well as or including modified proteins such as glycoproteins. A membrane sample may also include structures such as lipid rafts and caveolae. Membrane samples may also include cholesterol, fatty acids, glycoproteins, and hopanoids. In an embodiment, the membrane sample is a sample of complex proteins.

As used herein, "expression" refers to a level, form, or localization of product. For example, "expression of a protein" refers to one or more of the level, form (e.g., presence, absence or quantity of modifications, or cleavage or other processed products), or localization of the protein.

The term "proteome" refer to the protein constituents expressed by a genome, typically represented at a given point in time. A "sub-proteome" is a portion or subset of the proteome, for example, the proteins involved in a selected metabolic pathway, or a set of proteins having a common enzymatic activity.

A "remote location," refers to location other than the location at which the affinity purification and/or mass spectroscopy occurs. For example, a remote location could be another location (e.g., office, lab, etc.) in the same city, another location in a different city, another location in a different state, another location in a different country, etc. As such, when one item is indicated as being "remote" from another, what is meant is that the two items are at least in different rooms or different buildings, and may be at least one mile, ten miles, or at least one hundred miles apart.

"Communicating information" refers to transmitting the data representing that information as signals (e.g., electrical, optical, radio, magnetic, etc) over a suitable communication channel (e.g., a private or public network).

As used herein, a component of a system which is "in communication with" or "communicates with" another component of a system receives input from that component and/or provides an output to that component to implement a system function. A component which is "in communication with" or which "communicates with" another component may be, but is not necessarily, physically connected to the other component. For example, the component may communicate information to the other component and/or receive information from the other component. "Input" or "Output" may be in the form of electrical signals, light, data (e.g., spectral data), materials, or may be in the form of an action taken by the system or component of the system. The term "in communication with" also encompasses a physical connection that may be direct or indirect between one system and another or one component of a system and another.

"Forwarding" an item refers to any means of getting that item from one location to the next, whether by physically transporting that item or otherwise (where that is possible) and includes, at least in the case of data, physically transporting a medium carrying the data or communicating the data.

A "computer-based system" refers to the hardware means, software means, and data storage means used to analyze the information of the present disclosure. The minimum hardware of the computer-based systems of the present disclosure comprises a central processing unit (CPU), input means, output means, and data storage means. A skilled artisan can readily appreciate that any one of the currently available computer-based system are suitable for use in the present disclosure. The data storage means may comprise any manufacture comprising a recording of the present information as described above, or a memory access means that can access such a manufacture. In certain instances a computer-based system may include one or more wireless devices.

To "record" data, programming or other information on a computer readable medium refers to a process for storing information, using any such methods as known in the art. Any convenient data storage structure may be chosen, based on the means used to access the stored information. A variety of data processor programs and formats can be used for storage, e.g. word processing text file, database format, etc.

A "processor" references any hardware and/or software combination which will perform the functions required of it. For example, any processor herein may be a programmable digital microprocessor such as available in the form of a electronic controller, mainframe, server or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic medium or optical disk may carry the programming, and can be read by a suitable reader communicating with each processor at its corresponding station.

As used herein, a "database" is a collection of information or facts organized according to a data model, which determines whether the data is ordered using linked files, hierarchically, according to relational tables, or according to some other model determined by the system operator.

As used herein, an "information management system" refers to a program, or series of programs, which can search a database and determine relationships between data identified as a result of such a search.

As used herein, an "interface on the display of a user device" or "user interface" or "graphical user interface" is a display (comprising text and/or graphical information) displayed by the screen or monitor of a user device connectable to the network which enables a user to interact with a system processor and/or system memory (e.g., including a data base and information management system).

As used herein, "providing access to at least a portion of a database" refers to making information in the database available to user(s) through a visual or auditory means of communication.

As used herein, "separation" refers to chromatographically dividing, partially or completely, a substance, such as a protein mixture, into its component parts, such as like similar protein molecules, and optionally the removal of impurities.

The term "assessing" and "evaluating" are used interchangeably to refer to any form of measurement, and includes determining if an element is present or not. The terms "determining," "measuring," and "assessing," and "assaying" are used interchangeably and include both quantitative and qualitative determinations. Assessing may be relative or absolute. "Assessing the presence of" includes determining the amount of something present, as well as determining whether it is present or absent.

Methods of the Present Invention

In embodiments, the disclosure provides a method of protein separation, comprising: fractionating a mixture of proteins on a superficially porous phase with a gradient composition comprised of varying amounts of an ion-pairing agent, a pH-conditioning solvent and/or organic modifier and thereafter contacting the stationary phase with a greater than about 80% organic phase (e.g., such as an organic phase comprising an organic modifier such as acetonitrile), a greater than about 85% organic phase, a greater than about 90% organic phase, a greater than about 95% organic phase or a 100% organic phase. In certain aspects, after equilibration in a greater than 80% organic phase, the stationary phase is reused to separate another protein sample. In one aspect, the stationary phase is reused at least about 5 times, at least about 10 times, at least about 20 times, at least about 30 times, at least about 40 times, or at least about 50 times.

In certain aspects, prior to separating proteins using superficially porous phases according to the disclosure, a protein sample is contacted with an immunoaffinity stationary phase to deplete the sample of undesired proteins (e.g., such as high abundance proteins).

In certain aspects, prior to separating proteins using superficially porous stationary phase according to the disclosure, a protein sample is contacted with an immunoaffinity stationary phase to enrich the sample for one or more types of proteins or protein fragments (e.g., such as glycoproteins, cysteine-containing proteins, or phosphopeptides). Both immunodepletion and enrichment of a sample may be performed prior to using the superficially porous phase according to the disclosure.

In certain other aspects, proteins may be contacted with a cleaving agent (e.g., such as trypsin) to generate a peptide sample. Such contacting may be done prior to or after an immunoaffinity separation step or prior to or after separating using the superficially porous phase.

Proteins or peptides separated using superficially porous phases may be detected and/or quantitated and/or further characterized to determine their properties (e.g., such as amino acid sequence, mass/charge ratio and the like). In one aspect, separated proteins or peptides are analyzed by a proteome analysis system such as one including a mass spectrometer.

In one embodiment, the disclosure also provides systems for performing protein separations. In one aspect, a system according to the disclosure comprises a module for performing an immunoaffinity separation operably interfaced with a module comprising a superficially porous stationary phase. In another aspect, the system comprises a separation module comprising a superficially porous phase operably interfaced with a proteomic analysis system such as a mass spectrometer. In a further aspect, the system comprises a module for performing an immunoaffinity separation, a separation module comprising a superficially porous stationary phase and a proteomic analysis system. In one aspect, the system comprises a processor for providing instructions to various modules of the system to implement system functions.

In one aspect, the processor provides instructions to the separation module to perform a separation at a temperature of at least about 40° C., at least about 45° C., at least about 50° C., at least about 60° C., at least about 70° C., and up to about 95° C. or greater. In another aspect, the separation module comprises a mechanism for controlling the temperature of the separation module that is controllable by the system processor. For example, in one aspect, the separation module comprises a column comprising a heatable column jacket, responsive to instructions from the system processor.

In a further aspect, the system processor provides instructions to fluidics in communication with the separation module to contact a superficially porous stationary phase in the separation module with a gradient composition comprising varying amounts of an ion-pairing agent, a pH-conditioning solvent and/or organic modifier after selected intervals of time (e.g., pre-programmed). In still a further aspect, the system processor provides instructions for equilibrating the separation module in an at least about 80% organic phase (e.g., such as an organic phase comprising an organic modifier such as acetonitrile), a greater than about 85% organic phase, a greater than about 90% organic phase, a greater than about 95% organic phase or a 100% organic phase, prior to performing a new separation procedure. In one aspect, the system processor instructs the system to repeat at least about 5 separation cycles, at least about 10 separation cycles, at least about 20 separation cycles, at least about 30 separation cycles or at least about 50 separation cycles. In certain aspects, new separation modules are provided to the system (either manually or in an automated process) after at least about 5 separation cycles, at least about 10 separation cycles, at least about 20 separation cycles, at least about 30 separation cycles or at least about 50 separation cycles.

Protein analysis, such as proteomic analysis of human serum, presents a formidable challenge due to the dynamic range of the proteins of interest. In serum, for example, the quantities of proteins and peptides of interest can range from those considered "high abundance," for example, present at from about 2 to about 50% by weight or more of total protein, to those present at, for example, from about 10-12% by weight or less. An approach to address the complexity of samples having both high and low abundance proteins has been the application of multidimensional separation techniques, see for example, U.S. Published Patent Application No. 20040115725, to Pieper, et al.

A number of other techniques or methodologies are available to accomplish, for example, pre-fractionation depletion of high abundance components, see for example the following documents: Chernokalskaya, et al., *Electrophoresis*, 2004, 25, 2461-2468 (ultrafiltration); Liu, et al., *Anal. Chem.*, 2004, 76, 4193-4201 (model for sampling and estimation of relative protein abundance); Righetti, et al., *Proteomics*, 2003, 3, 1397-1407 (review of prefractionation techniques); Van den Bergh, et al., *Electrophoresis*, 2003, 24, 1471-1481 (reversed-phase HPLC prefractionation prior to 2-D DIGE and MS); Neverova, et al., *Proteomics*, 2002, 2, 22-31 (RP-HPLC in subproteomic analysis) techniques); and Lescuyer, et al., *Electrophoresis*, 2004, 25, 1125-1135 (review of proteome analysis by chromatographic prefractionation), the entire disclosures of which are incorporated herein by reference.

In embodiments, the present disclosure provides methods for the separation and fractionation, of protein samples. In embodiments, the present disclosure provides RP HPLC methods for the separation and fractionation of protein samples. In certain aspects, the protein samples are immunodepleted to reduce the complexity of the samples, to remove undesired constituents (such as high abundance proteins), by binding desired proteins (e.g., such as cysteine-containing proteins) to an affinity matrix and recovering the bound proteins or by using a combination of the above techniques.

In embodiments, the present disclosure provides a method of protein separation, comprising: fractionating a mixture of proteins on a superficially porous stationary phase at a temperature of, for example, from about 40 to about 95° C. or from about 70 to about 95° C.

In one aspect, the superficially porous stationary phase comprises a core of non-porous material and an outer layer of porous material. The outer layer of porous material comprises a chromatographically active material, such as an organosilane or modified form thereof. In certain aspects, the outer layer of porous material comprises silica particles stably associated with the non-porous core (i.e., the particles remain associated with the core under the conditions being used for separation).

In one embodiment, the recovery of separated proteins increases with an increase in the temperature selected and using stationary phases and conditions according to the present disclosure. In one aspect, the method yields separated proteins in recoveries of from about 70-100 weight percent of the mixture of proteins, or from about 95-100 weight percent of the mixture of proteins.

In embodiments, the method can further comprise, prior to fractionating, depleting undesired proteins in a sample with, for example, an immunoaffinity matrix, or using like techniques, to provide a depleted mixture of proteins for fractionating on a superficially porous stationary phase according to the disclosure. In one aspect, the undesired proteins comprise abundant sample proteins. As used herein, "abundant sample proteins" can comprise, for example, from about 50 to about 95 percent by weight of the total protein sample prior to depletion, and the mixture of proteins for fractionating can comprise, for example, less than about 50 percent by weight of the total protein prior to depleting.

Superficially Porous Stationary Phase

A superficially porous stationary phase is a stationary phase suitable for use in chromatographic separations wherein the stationary phase is formed of superficially porous particles. The superficially porous particles include a core surrounded by porous coating. In various embodiments, a superficially porous particle includes a core coated with microparticles and in some embodiments ultramicroparticles. The microparticles and ultramicroparticles provide a porous outer region and surface of the macroparticle. Examples of superficially porous stationary phases are disclosed, for example, in U.S. Pat. Nos. 3,505,785, 4,070,283, and 4,477,492, the disclosures of which are incorporated by reference herein in their entirety.

The superficially porous stationary phase, in embodiments, can have particles having an average particle diameter of, for example, about 2 to about 20 micrometers, such as about 10 micrometers, and preferably an average particle diameter of about 3 to about 5 micrometers. In certain aspects, where the stationary phases are used in RP-HPLC, the reversed-phase of the porous stationary phase is a silane, in embodiments, comprising a $C_6$ to about $C_{30}$ hydrocarbon, such as an alkane, a substituted alkane, an alkene, a substituted alkene, an aryl or substituted aryl, and like hydrocarbons, or combinations thereof. Similarly, possible silane substituents of a hydrocarbon can be, for example, either partially or fully substituted fluorocarbons, or may contain additionally, or alternatively, other halogen atoms in positions occupied by hydrogen atoms in hydrocarbons. Additional possible substituents of a "substituted" hydrocarbon can be, for example, a saturated or unsaturated, straight or branched $C_1$ to about $C_6$ hydrocarbon, a cyano, an amino, an hydroxyl, a carbamate, an amide, an urea, a succinimide, a saturated or unsaturated, straight or branched $C_1$ to about $C_6$ alkyl ether such as an alkoxy group, an ester, an aryl, and like groups, and combinations thereof. In various embodiments, halo includes fluoro, chloro, bromo, or iodo. Alkyl, alkoxy, etc., include both straight, branched, and cyclic groups; but reference to an individual radical such as "propyl" embraces only the straight chain radical, a branched chain isomer such as "isopropyl" being specifically referred to. "Alkyl" includes linear alkyls, branched alkyls, and cycloalkyls. "Aryl" includes a phenyl radical or an ortho-fused bicyclic carbocyclic radical having about nine to twenty ring atoms in which at least one ring is aromatic. Aryl (Ar) can include substituted aryls, such as a phenyl radical having from 1 to 5 substituents, for example, alkyl, alkoxy, halo, and like substituents.

Pore sizes of stationary phases used in methods according to the disclosure may vary and may be varied to suit a particular biomolecule being separated. In one aspect, the average pore size is greater than or equal to about 300 Å, while in another aspect, stationary phases having pore sizes of less than 300 Å are used.

The reversed-phase of the superficially porous stationary phase can be, for example, a silane compound having a C6 to about $C_{30}$ hydrocarbon group. The reversed-phase of the superficially porous stationary phase can be, for example, a divalent silane having a structure:

wherein, for example, R is an n-octadecyl group, an n-tetradecyl group, or mixtures thereof, and Me is methyl. The terminal "-" marks represent points of attachment of the divalent silane to a surface group or stationary phase. U.S. Pat. Nos. 6,057,468 and 5,948,531, disclose bidentate silanes suitable for use in forming the bonded reversed-phase of the macroporous or superficially porous phases of the present disclosure. Additionally or alternatively, the reversed-phase of the superficially porous stationary phase can be, for example, a silane of the formula:

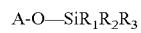

where $R_1$, $R_2$, and $R_3$ are each independently alkane, substituted alkane, alkene, substituted alkene, aryl or substituted aryl; and A is a surface group of the substrate to which the silane is attached. In embodiments, the reversed-phase can be, for example, a $C_3$ to about $C_{30}$ hydrocarbon or a corresponding monovalent or bivalent silane compound having a $C_{10}$ to about $C_{30}$ hydrocarbon, such as a —$SiR_2C_{3-30}$ for a monovalent silane, of the formula —Si(R)(Me)—(R')—Si(R)(Me)— for a bivalent silane where R' is a divalent hydrocarbon spacer group with from 1 to about 10 carbon atoms, such as —Si($C_{3-30}$)(Me)—(CH$_2$)$_3$—Si($C_{3-30}$)(Me)—. In embodiments, the hydrocarbon of the reversed-phase hydrocarbon or the corresponding monovalent or bivalent silanes can be, for example, a substituted or unsubstituted, straight or branched, $C_3$ to $C_{20}$ hydrocarbon, such as a $C_{18}$ hydrocarbon. U.S. Pat. No. 4,847,159, discloses substrates coated with sterically protected organo-silanes suitable for use in preparing the bonded reverse-phase of the macroporous or superficially porous phases of the present disclosure.

Sample Preparation

The mixture of proteins, prior to fractionating, can be, for example, in an aqueous mixture of urea and acetic acid, such as about 6 M urea and about 5 weight % aqueous acetic acid. The mixture of proteins can be eluted, for example, with a gradient composition comprised of varying amounts of an ion-pairing agent, a pH-conditioning solvent and/or organic modifier.

Mobile Phase

In one aspect, the gradient composition comprises an ion-pairing agent that binds by ionic interaction to solute molecules to increase their hydrophobicity. Suitable ion-pairing agents include, but are not limited to: anionic ion pairing agents, such as, for example, trifluoroacetic acid (TFA), pentafluoroproprionic acid (PFPA), heptafluorobutyric acid (HFBA), and cationic ion pairing agents, such as, for example, tetramethyl ammonium chloride, tetrabutylammonium chloride, and tri ethyl amine.

In another aspect, a pH-conditioning solvent is provided which comprises a solvent suitable for providing a desired pH for the gradient composition. In one aspect, the pH-conditioning solvent comprises a low pH-conditioning solvent, e.g., for providing a gradient composition comprising a pH of less than about 5, less than about 4 or between about 2-4. Suitable low pH-conditioning solvents include, but are not limited to, trifluoroacetic acid, heptafluorobutyric acid and ortho-phosphoric acid. Mobile phases containing ammonium acetate or phosphate salts are suitable for use at pH's closer to neutrality. Mobile phases suitable for use at pHs above neutrality include, but are not limited to, buffers containing borate salts, glycine, or ammonium hydroxide.

In certain aspects, the ion-pairing agent also may serve as the pH-conditioning solvent. For example, one ion-pairing agent, such as trifluoroacetic acid, may also be used to maintain a low pH of the mobile phase.

In a further aspect, the gradient composition comprises one or more organic modifiers. As used herein, an "organic modifier" refers to a solvent or a compound which can be used in chromatographic procedures and like separation methods, to alter the properties of the mobile phase to controllably effect serial elution of desired materials. In one aspect, an organic modifier decreases ionic interactions between molecules in the mobile phase and the solid phase. For example, in one aspect, an organic modifier comprises a solvent added to a mobile phase to decrease its polarity. Suitable organic modifiers include, but are not limited to, acetonitrile, ethanol, methanol, ethanol, n-propanol or iso-propanol (e.g., 1- or 2-propanol).

In embodiments, the gradient elution can be accomplished, for example, stepwise, linearly, with multisegmented linear or stepwise changes in composition, or with a combination thereof. In one aspect, gradient elution is performed in increasing amounts of organic modifier and elution is completed in greater than about 10%, greater than about 20%, greater than about 30%, greater than about 90%, or up to and including about 100% of organic modifier. In certain aspects, elution is completed in decreasing amount of organic modifier, e.g., less than about 20%, less than about 15%, less than about 10%, less than about 5%, less than about 2%, less than about 1% or about 0% of organic modifier.

The separating can be accomplished with any suitable solvent or solvent combination. In one aspect, the gradient composition comprises aqueous trifluoroacetic acid and acetonitrile. For example, fractionating can be accomplished using a mobile phase including: about 0.01 to about 2 weight % trifluoroacetic acid in water, referred to as solvent (A); 0.01 to about 2 weight % trifluoroacetic acid in acetonitrile, referred to solvent (B); and combinations or mixtures thereof. In embodiments, the mobile phase can be, for example, from about 0.01 to about 2 weight % trifluoroacetic acid in water, for example, 0.1 weight % trifluoroacetic acid in water and having increasing amounts of an organic modifier over time. In embodiments, the mobile phase can be from about 0.01 to about 2 weight % trifluoroacetic acid in water, such as 0.08 weight % aqueous trifluoroacetic acid in acetonitrile and having increasing amounts of acetonitrile over time.

In a further aspect, the gradient composition comprises aqueous trifluoroacetic acid, acetonitrile, formic acid, and isopropanol. For example, fractionating can be accomplished using a mobile phase including one or more of the following: (A) about 0.01 to about 2 weight % trifluoroacetic acid in water; (B) about 0.01 to about 2 weight % trifluoroacetic acid in acetonitrile; (C) 5 to about 50 weight % formic acid in acetonitrile; and (D) about 100% weight isopropanol; and combinations or mixtures thereof. In further embodiments, the mobile phase can be (A) about 0.01 to about 2 weight % trifluoroacetic acid in water, with increasing amounts over time of (B) about 0.01 to about 2 weight % trifluoroacetic acid in acetonitrile, followed by increasing amounts over time of (C) about 5 to about 50 weight % formic acid in acetonitrile. In still further embodiments, the mobile phase can be (A) about 0.01 to about 2 weight % trifluoroacetic acid in water with increasing amounts over time of (B) 0.01 to about 2 weight % trifluoroacetic acid in acetonitrile, followed by increasing amounts over time of (C) 5 to about 50 weight % formic acid in acetonitrile, and followed by increasing amounts over time of (D) 100% weight isopropanol.

In embodiments, fractionating a mixture of proteins on a reversed-phase superficially porous stationary phase at a temperature of greater than or equal to about 40° C. separates proteins in high recoveries. In embodiments, fractionating a mixture of proteins on a reversed-phase superficially porous stationary phase at elevated temperatures, and optionally with a multi-segment gradient elution as illustrated herein, provides, compared to a porous phase material, improved chromatographic performance such as enhanced peak selectivity, enhanced peak resolution, reduced band-broadening, and like improvements, or combinations thereof. For additional descriptions of chromatographic methods, performance, and terminology, see for example in: 1) *HPLC of Biological Macromolecules, Methods and Applications*, Marcel Decker, Inc., vol. 51, 1990, chap. 1, *Silica as a Support*, Unger, K. K.; chap. 3, *Size Exclusion Chromatography*, Gooding, K. M., Regnier, F. E.; and chap. 6, *Reverse Phase Chromatography in Analytical Biotechnology of Proteins*, Frenz, J., Hancock, W. S., Henzel, W. J.; and in 2) *Practical HPLC Method Development*, Snyder, L. R., Kirkland, J. J., Glajch, J. L., $2^{nd}$ Ed, John Wiley & Sons, Inc. 1997, chap. 11, *Biochemical Samples: Proteins, Nucleic Acids, Carbohydrates, and Related Compounds*, Boyes, B. E., Alpert, A.

In embodiments, the mixture of proteins can be eluted, for example, with an elution gradient comprised of:

from about 5 to about 30 weight % of from about 0.1 weight % aqueous trifluoroacetic acid in acetonitrile;

from about 30 to about 55 weight % of from about 0.1 weight % aqueous trifluoroacetic acid in acetonitrile;

from about 55 to about 100 weight % of from about 0.1 weight % aqueous trifluoroacetic acid in acetonitrile; and about 100 weight % of from about 0.1 weight % aqueous trifluoroacetic acid.

In one specific example, the mixture of proteins can be eluted, for example, with a gradient comprised of:

from about 5 to about 30 weight % of from about 0.1 weight % aqueous trifluoroacetic acid in acetonitrile for about 1 to about 10 min;

from about 30 to about 55 weight % of from about 0.1 weight % aqueous trifluoroacetic acid in acetonitrile for about 5 to about 60 min.;

from about 55 to about 100 weight % of from about 0.1 weight % aqueous trifluoroacetic acid in acetonitrile about 1 to about 20 min.; and about 100 weight % of from about 0.1 weight % aqueous trifluoroacetic acid for about 1 to about 20 min.

In another specific example, the mixture of proteins can be eluted, for example, with a gradient comprised of:

from about 5 to about 30 weight % of 0.08 weight % aqueous trifluoroacetic acid in acetonitrile in 5 min;

from about 30 to about 55 weight % of 0.08 weight % aqueous trifluoroacetic acid in acetonitrile in 33 min.;

from about 55 to about weight 100% of 0.08 weight % aqueous trifluoroacetic acid in acetonitrile in 10 min.; and about 100 weight % of 0.08 weight % aqueous trifluoroacetic acid in 4 min.

In additional embodiments, a membrane sample can be fractionated (i.e. eluted), for example, with an elution gradient comprised of:

about 80% weight percent (A) 0.01 to about 2 weight % trifluoroacetic acid in water and about 20 weight % of (B) about 0.01 to about 2 weight % trifluoroacetic acid in acetonitrile with addition over time of:

from about 20 to about 100 weight % of (B) about 0.01 to about 2 weight % trifluoroacetic acid in acetonitrile, in about 1 to 70 minutes;

from about 0 to about 100 weight % of (C) about 5 to about 50 weight % formic acid in acetonitrile, in about 1 to 20 minutes; and from about 0 to 100 weight % of (D) about 100% weight isopropanol, in about 1 to 20 minutes.

In further embodiments, a membrane sample can be fractionated, for example, with an elution gradient comprised of:

about 80% weight percent (A) 0.01 to about 2 weight % trifluoroacetic acid in water and about 20 weight % of (B) about 0.01 to about 2 weight % trifluoroacetic acid in acetonitrile with addition over time of:

from about 20 to about 50 weight % of (B) about 0.01 to about 2 weight % trifluoroacetic acid in acetonitrile, in about 1 to 50 minutes;

from about 50 to about 100 weight % of (B) about 0.01 to about 2 weight % trifluoroacetic acid in acetonitrile, in about 1 to 20 minutes;

from about 0 to about 100 weight % of (C) about 5 to about 50 weight % formic acid in acetonitrile, in about 1-20 minutes; and from about 0 to 100 weight % of (D) about 100% weight isopropanol, in about 1 to 20 minutes.

In further specific embodiments, a membrane sample can be fractionated, for example, with an elution gradient comprised of:

about 80% weight percent of (A) 0.01 to about 2 weight % trifluoroacetic acid in water, and about 20 weight % of (B) about 0.01 to about 2 weight % trifluoroacetic acid in acetonitrile, with addition over time of:

from about 20 to about 50 weight % of (B) about 0.01 to about 2 weight % trifluoroacetic acid in acetonitrile in about 40 minutes;

from about 50 to about 100 weight % of (B) about 0.01 to about 2 weight % trifluoroacetic acid in acetonitrile in about 10 minutes;

from about 0 to about 100 weight % of (C) about 5 to about 50 weight % formic acid in acetonitrile in about 10 minutes; and from about 0 to 100 weight % of (D) about 100% weight isopropanol, in about 5 minutes.

The disclosure further provides methods for regenerating superficially porous solid phases described above. In one aspect, the solid phase may be used greater than about 5 times at temperatures of from about 40° C. to about 95° C., greater than about 10 times, greater than about 20 times, greater than about 30 times, greater than about 40 times, and greater than about 50 times. In certain aspects, after contacting the solid phase with the gradient compositions described above, the solid phase is contacted with a 100% organic phase, containing 0.08% trifluoroacetic acid. For example, in one aspect, the gradient is completed with 100% acetonitrile, containing 0.08% trifluoroacetic acid.

The load of proteins, such as a membrane sample, on the solid phase can be, in embodiments, for example, from about 100 micrograms to about 2 grams, and preferably from about 100 micrograms to about 2,000 micrograms, and more preferably about 100 micrograms to about 200 micrograms.

The method can further comprise collecting each of the resulting separated or fractionated membrane sample proteins.

Reduction in Sample Complexity

As discussed above, in certain aspects, the complexity of the sample is reduced prior to contacting with a superficially porous phase. For example, the sample may be contacted with an affinity matrix for depleting a sample of undesired proteins, such as high abundance proteins. The nature of the protein to be removed will generally depend on the sample, and may include albumin, in the case of serum; phaseolin, zein, globulins, protamines and glutinins, in the case of certain plants. Other proteins which may be removed from a sample include, but are not limited to: oil seed proteins, Rubisco, ribosomal proteins, both chloroplast and cytosolic, thylacoit, photosynthesis system I proteins, photosynthesis system II proteins, chloroplast membrane binding proteins and other structural proteins, viral proteins, bacterial proteins, and the like.

The immunoaffinity phase, if selected for depletion in the method, can comprise for example, an affinity binding composition comprising:

a first and second solid phase matrix comprising a first receptor immobilized on a first solid phase matrix, capable of specific binding to a first ligand but not a second ligand; and a second receptor immobilized on a second solid phase matrix, capable of specific binding to the second ligand but not the first ligand (e.g., under binding conditions to which the solid phase is exposed).

In certain aspects, the first and second sold phase matrix are mixed together in a column or in a solution. For example, the first and second solid phase matrix may contact each other. In certain other aspects, the first and second solid phase matrix do not form discrete zones as in a test strip. The solid phase may comprise additional receptor molecules, such as an optional third receptor immobilized on a third solid phase matrix, capable of specific binding to a third ligand but not the first ligand or the second ligand;

an optional fourth receptor immobilized on a fourth solid phase matrix, capable of specific binding to a fourth ligand but not the first ligand, the second ligand or the third ligand; and an optional a fifth receptor immobilized on a fifth solid phase matrix, capable of specific binding to a fifth ligand but not the first ligand, the second ligand, the third ligand or the fourth ligand.

As used herein, a "receptor" may include any molecule that may serve as a binding partner for any molecule to be depleted from a sample. For example a receptor may comprise an antibody or antigenic fragment thereof. However, a "receptor" as used herein is not necessarily a protein, but may also comprise a polypeptide, peptide, metal, metal coordination compound, carbohydrate (e.g., a lectin, such as concanavalin A or wheat germ agglutinin), aptamer, nucleic acid, co-factor, heparin, polymyxin, dye (such as Cibacron blue F3GA), a hydrocarbon (such as a methyl and phenyl radical that binds hydrophobic proteins), an agent comprising a functional group with affinity for protein moieties (such as a hydrazide, amine, N-hydroxy-succinimide, carboxyl, boronate and organomercury molecule) and generally, or any other molecule with the desired binding specificity.

Immunoaffinity liquid chromatography stationary phases or solid phases are described, for example, in the above mentioned U.S. Published Patent Application No. 20040115725, to Pieper, et al.

Immunoaffinity columns may also be used to enrich for desired proteins. In this embodiment, a sample is contacted with an immunoaffinity solid phase comprising at least a first receptor that is a binding partner for a protein (or type of protein) to be enriched for in the sample. In this aspect, the proteins bound to the immunoaffinity solid phase are of interest for further separation by superficially porous phases according to the disclosure, rather than those proteins that are in the immunodepleted sample flowing past the immunoaffinity stationary phase. Thus, in one aspect, a sample may be contacted with an immunoaffinity stationary phase to provide complexes of proteins bound to the immunoaffinity stationary phase and the bound proteins are then eluted for further separation by the superficially porous phase.

As with the immunodepletion columns described above, immunoaffinity stationary phases for enriching protein samples may comprise a plurality of different binding molecules or receptors with different and exclusive affinities (e.g., binding to one ligand but not another) under the conditions being used. In one aspect, for example, an immunoaffinity stationary phase comprises a binding partner (e.g., such as an iodacetate derivative) for selecting cysteine-containing peptides. In another aspect, the immunoaffinity column comprises a binding partner for binding carbohydrate-comprising proteins and the like. In a further aspect, the immunoaffinity stationary phase binds both types of proteins. A receptor for enrichment of a sample may include, but is not limited to, an antibody or antigenic fragment thereof, a polypeptide, peptide, metal, metal coordination compound, carbohydrate (e.g., a lectin, such as concanavalin A or wheat germ agglutinin), aptamer, nucleic acid, co-factor, heparin, polymyxin, dye (such as Cibacron blue F3GA), a hydrocarbon (such as a methyl and phenyl radical that binds hydrophobic proteins), an agent comprising a functional group with affinity for protein moieties (such as a hydrazide, amine, N-hydroxy-succinimide, carboxyl, boronate and organomercury molecule) and generally, may comprise any molecule with the desired binding specificity.

In certain aspects, a sample is both immunodepleted to remove undesired proteins and immunoselected to enrich for desired proteins, prior to contacting with superficially porous phase according to the disclosure.

An affinity-purified population of proteins may comprise natural proteins, synthetic proteins, modified proteins, unmodified proteins, processed proteins or unprocessed proteins, and combinations thereof.

Suitable stationary phase materials for use as immunoaffinity depletion include but are not limited to gels, fibers, microspheres, spheres, cubes, particles, beads (including porous beads), pellets, planar substrates (e.g., slides, discs, wafers, chips), channels, microchannels, nanochannels, capillaries, walls of containers, membranes, webs, gels, sheets, tubing, spheres, containers, pads, slices, films, plates, slides, strips, plates, disks, rods, particles, beads, and filters.

Immunoaffinity phases may be formed of a variety of materials and the size and shape of the substrate is not a limiting feature of the disclosure. The substrate may be rigid or flexible or semi-flexible. The term "rigid" is used herein to refer to a structure e.g., a bottom surface that does not readily bend without breakage, i.e., the structure is not flexible. The term "flexible" is used herein to refer to a structure, e.g., a bottom surface or a cover, which is capable of being bent, folded or similarly manipulated without breakage. In one aspect, the substrate comprises a flexible web that can be bent 180 degrees around a roller of less than 1.25 cm in radius at a temperature of 20° C.

Rigid solid stationary phases may be made from silicon, glass, rigid plastics, e.g. polytetrafluoroethylene, polypropylene, polystyrene, polycarbonate, etc., or metals, e.g. gold, platinum, etc. Flexible stationary phases may be made from a variety of materials, such as, for example, nylon, nitrocellulose, polypropylene, polyester films, e.g., polyethylene terephthalate, polymethyl methacrylate or other acrylics, polyvinyl chloride or other vinyl resin. Various plasticizers and modifiers may be used with polymeric substrate materials to achieve selected flexibility characteristics.

Other Aspects of the Invention

In one aspect, a separation method described above may be combined with one or more additional separation methods. For example, the separation method may be combined with one or more of: gel filtration, liquid chromatography, ion exchange chromatography, electrophoresis (e.g., such as gel electrophoresis, capillary electrophoresis) and the like. Accordingly, phases according to the disclosure may be interfaced via fluidic couplings, e.g., columns, capillaries, microfluidic chips, combinations thereof, and the like, to devices for performing any of the above-mentioned separation techniques.

The method can further comprise analyzing at least one of the separated proteins. For example, any of the separation methods described above may be combined with a method for proteomic analysis, such as two-dimensional gel electrophoresis, mass spectrometry (including, but not limited to MALDI-TOF-MS, ESI, TOF, ion trap mass spectrometry, ion trap/TOF mass spectrometry, quadrupole mass spectrometry, Fourier Transform mass spectrometry, fast atomic bombardment (FAB), plasma desorption (PD), thermospray (TS), and magnetic sector mass spectrometry and the like), NMR and other techniques. The separated proteins can be analyzed, collectively or individually, to identify protein(s) of interest.

In certain aspects, prior to analysis, and/or prior to separation and/or prior to affinity selection or immunodepletion, proteins are fragmented by a cleaving agent to generate peptides which can be analyzed and which may provide a signature for a protein from which it is derived, e.g., detection of the peptide may be diagnostic of the presence of the protein in a sample.

Suitable cleaving agents include, but are not limited to, enzymes, for example, one or more of: serine proteases (e.g., such as trypsin, hepsin, SCCE, TADG12, TADG14); metallo proteases (e.g., such as PUMP-1); chymotrypsin; cathepsin; pepsin; elastase; pronase; Arg-C; Asp-N; Glu-C; Lys-C; carboxypeptidases A, B. and/or C; dispase; thermolysin; cysteine proteases such as gingipains, TEV protease, factor Xa and the like. Proteases may be isolated from cells or obtained through recombinant techniques. The cleaving agent is not limited to an enzyme and can be a chemical reagent, for example, cyanogen bromide (CNBr), 2-nitro-5-thiocyanobenzoic acid, N-bromosuccinamide and other reactive halogen compounds, hydroxylamine, 1-2M formic or acetic acid, periodate oxidation, 2-(2-nitrophenylsulfenyl)-3-methyl-3-bromoindolenine or o-iodosobenzoic acid (See, for example, Hermodson et al., "Methods in Protein Sequence Analysis", ed. Elzinga, Humans Press, Clifton, N.J., pp. 313-323, 1982).

In some aspects, the cleaving agent may be associated with the substrate. For example, the cleaving agent may be disposed within the pores of substrates comprising porous beads or may be immobilized via a binding partner.

Peptide sequence information may be automatically generated by selecting peptide ions of a particular mass-to-charge (m/z) ratio for collision-induced dissociation (CID) or other means for generating peptide ions known in the art. The resulting ionization spectra may then be correlated with sequences in sequence databases to identify the protein from which the sequenced peptide originated, e.g., using computer searching algorithms known in the art.

Peptides may be quantified by measuring the relative signal intensities for pairs of peptide ions of identical sequence that are tagged using different mass-altering labels, e.g., such as light or heavy forms of isotope, or which comprise label and unlabeled peptide pairs (which differ in mass by the mass of the label). In certain aspects, a peptide or mass-altering portion of a peptide may comprise a detectable label such as a radioactive label, spin label, chemiluminescent label, and the like.

In some aspects, mass spectrometry analysis may be used to determine both the quantity and identity of proteins from which labeled peptides are derived, for example, by using an automated multistage mass spectrometer and alternating scans which measure quantities of peptides eluting from a separation column and record sequence information from selected peptides.

In one embodiment, methods according to the disclosure are used to evaluate samples which have been exposed to an agent, e.g., proteins from a sample exposed to an agent are separated using superficially porous phases under conditions described above and may be analyzed using proteomic analysis methods such as mass spectrometry. The proteins may be compared to proteins in a reference sample may comprise a sample which is not exposed to the agent. Additional samples may comprise samples exposed to different concentrations of agents. Suitable agents which can be evaluated include, but are not limited to: drugs; toxins; proteins; proteins; peptides; amino acids; antigens; cells, cell nuclei, organelles, portions of cell membranes; viruses; receptors; modulators of receptors (e.g., agonists, antagonists, and the like); enzymes; enzyme modulators (e.g., such as inhibitors, cofactors, and the like); enzyme substrates; hormones; nucleic acids (e.g., such as oligonucleotides; polynucleotides; genes, cDNAs; RNA; antisense molecules, ribozymes, aptamers), and combinations thereof. Agents also can be obtained from synthetic libraries that are commercially available or generated through combinatorial synthesis using methods well known in the art.

Agents associated with a desired cell state or the transition from an undesired cell state (e.g., a pathology) to a desired cell state (e.g., absence of the pathology or reduction in symptoms or biomarkers diagnostic of the pathology) may be identified as candidate compounds for treating the undesired cell state, for example, in a patient from whom the sample of cells was derived. Such compounds may be formulated as pharmaceutical compositions using methods known in the art.

In certain aspects, expression of a protein or set or proteins, and/or modified and/or cleaved forms thereof, associated with a particular cell state may be used to generate diagnostic probes to detect or screen for the cell states. Such proteins (or modified or cleaved forms) may be detected directly, e.g., using mass spectrometry techniques or indirectly, e.g., using antibody probes.

In one embodiment, the disclosure further provides a system that interfaces superficially porous phases according to the disclosure with a protein/peptide analysis system such as a mass spectrometer.

In some aspects throughput can be increased by dividing eluted peptides into a plurality of sets and separating the sets using a plurality of separation devices and/or immunoaffinity columns operating in parallel and/or in series.

In one aspect, the system comprises a superficially porous phase provided in a column, capillary, or a channel (e.g., a microchannel or nanochannel) in a substrate. The superficially porous phase may itself be operably interfaced with an immunoaffinity phase, for example, provided upstream of the superficially porous phase in a column, capillary or channel format which operably interfaces with a column, capillary, or channel comprising the superficially porous phase by an appropriate fluidic connection (e.g., tubing, capillary, conduit, microfluidic system, and the like). As used herein, the term "operably interfaced" means that the interface is provided at an appropriate time such that fluid from an upstream column (e.g., an immunoaffinity support or stationary phase) may be provided to a downstream column (e.g., a separation column comprising superficially porous phase) at an appropriate time (e.g., to collect the flow through from an immunodepletion column or to collect eluted proteins previously bound to an immunoaffinity column which selects desired proteins).

In one aspect, a separation module (e.g., capillary, column, channel or the like) comprising superficially porous phases according to the disclosure interfaces with an mass spectrometer device through an interfacing module (e.g., an electrospray device, such as an electrospray capillary or nozzle) which delivers substantially purified proteins/peptides to the mass spectrometer. In the case where the analysis system comprises a MALDI device, an automated spotter may be used to connect a separation capillary to a MALDI device (see, e.g., Figeys et al., 1998, *Electrophoresis* 19: 2338-2347).

Throughput of the delivery process may be increased using arrays of electrospray or nanospray needles. See, e.g., Zubritsky et al., 2000, *Anal. Chem.*, 72: 22A; Licklider et al., *Anal. Chem.* 72: 367-375; Scherer et al., 1999, *Electrophoresis* 20: 1508-1517.

In another aspect, the system comprises one or more detectors for detecting movements of fluids, proteins, and/or peptides through the system.

Generally, the mass spectrometer device of the system comprises an ionizer, an ion analyzer and a detector. Any ionizer that is capable of producing ionized peptides in the gas phase can be used, such as an ion spray mass spectrometer (Bruins et al., 1987, *Anal Chem.* 59: 2642-2647), an electrospray mass spectrometer (Fenn et al., 1989, *Science* 246: 64-71), and laser desorption device (including matrix-assisted desorption ionization and surfaced enhanced desorption ionization devices). Any appropriate ion analyzer can be used as well, including, but not limited to, quadropole mass filters, ion-traps, magnetic sectors, time-of-flight, and Fourier Transform Ion Cyclotron Resonance (FTICR). In a preferred aspect, a tandem MS instrument such as a triple quadropole, ion-trap, quadropole-time-of flight, ion-trap-time of flight, or an FTICR is used to provide ion spectra. A FAB ionizer may also be used.

In one aspect, molecular ions generated by ionization of peptides delivered, for example, from an electrospray or nanospray are accelerated through an ion analyzer as charged molecules. Ions generated may be detected using any suitable detector. In one aspect, ions are isolated and fragmented to generate daughter ions which may detected which may provide a unique signature for the peptide.

Generally, peptides typically fragment at the amide bond between amino acid residues and peaks correspond to particular amino acids or combinations of amino acids. While there may be additional peaks (ions) present in the product ion spectra, many of these other peaks can be predicted and their presence explained by comparison with spectral data of known compounds (e.g., standards). Many different processes can be used to fragment the parent ion to form product ions, including, but not limited to, collision-induced dissociation (CID), electron capture dissociation, and post-source decay.

In another aspect, the system further comprises a system processor which can convert signals obtained from different components of the system (e.g., such as electrical signals) into data and can provide instructions for controlling one or more system functions. In one aspect, data includes, but is not limited to, data relating to binding conditions and/or elution conditions during affinity purification, data relating to separation, concentration, and/or purification of proteins/peptides eluted from a separation module comprising superficially porous phases, data relating to fluid movement in the system (e.g., the operation of pressure or electroosmotic pumps), as well as data relating to peptide fragmentation, ionization, peptide quantity and amino acid sequence.

In some aspects, the processor compares mass spectral data to sequences in a protein and/or nucleic acid sequence database which the processor may access remotely. Thus, in a further aspect, the system further comprises a memory for storing data relating to peptide masses, and/or amino acid sequence. In another aspect, the system additionally comprises an information management system for searching and comparing data in the memory and obtained from mass spectrometry analysis. However, in other aspects, the processor obtains sequence information directly from mass spectral data provided to it from the mass spectrometer. The type of protein or peptide analysis performed by the system processor will relate to the type of mass spectrometer or other protein analysis device used in the system.

In still another aspect, in response to data from various system components, the processor alters one or more functions of the system. In additional or alternative embodiments, the processor is programmed, for example, by a user of the system and/or remotely to provide particular system instructions.

The disclosure additionally provides computer program products comprising computer readable medium providing instructions to a processor in communication with a system described above to control one or more system functions, e.g., exposure of superficially porous phases to gradient compositions and/or temperature conditions, contacting proteins to a cleaving agent, ionization or peptide fragments, delivery of peptides to a mass spectrometer, analysis of mass spectra, and the like.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the claims appended hereto.

Materials and Methods

Materials. HPLC-grade acetonitrile was purchased from Burdick & Jackson. The water used was Milli-Q grade (Millipore, Bedford, Mass.). Trifluoroacetic acid 99%+ was purchased from Sigma. Urea, sequanal grade, was obtained from Pierce (Rockford, Ill.). The 15 mL and 50 mL conical BD polystyrene tubes were obtained from VWR International. Pre-cast gels were obtained from Novex/Invitrogen (Carlsbad, Calif.). The Multiple Affinity Removal System column, reversed-phase porous and macroporous resins, were provided by Agilent Technologies (Wilmington, Del.). Serum samples were collected from a healthy male volunteer.

Immunoaffinity Depletion of High-abundant Proteins from Human Serum

The blood was collected in a BD Vacutainer tube with SST gel and clot activator (Becton Dickinson, #367988). After clot formation, the sample was centrifuged at 1,000×g for 15 minutes. The serum was removed, aliquoted, and stored at −70° C. Total time for serum processing was less than 60 min.

High-abundant protein removal from human serum was performed on a 4.6×100 mm immunodepletion column (Agilent Technologies, #5185-5985). This column specifically removed albumin, IgG, anti-trypsin, IgA, transferrin and haptoglobin in a single column run. Prior to injection on the column, serum samples were thawed and diluted five times with Buffer A—a salt-containing neutral buffer (pH-7.4) used for loading, washing and re-equilibrating the column (Agilent Technologies, #5185-5987). "Complete" protease inhibitors cocktail (Roche, #1 873 580) was added to serum to prevent proteolytic degradation. The sample was transferred to a 0.22 μm pore size spin tube (Agilent Technologies, #5185-5990) for removal of particulates by centrifugation at 16,000×g for 1 minute at room temperature. The prepared samples were maintained at 4° C. in the temperature-controlled autosampler stage of the Agilent 1100 LC system. 180 μl (36 μl sera diluted 5× with Buffer A) of sample was injected onto the 4.6×100 mm column in 100% Buffer A at a flow rate of 0.5 ml/min for 10.0 minutes. After collection of the flow-through fraction, the column was washed and the bound proteins eluted with 100% Buffer B—a low pH urea buffer (Agilent Technologies, #5185-5988) at a flow rate of 1.0 ml/min for 7.0 minutes. Afterward, the column was regenerated by equilibrating it with Buffer A (0% B) for 11.0 minutes for a total run cycle of 28.0 minutes.

Fraction collection of flow-through proteins was time-controlled and corresponded to the UV 280 nm absorbance of the eluting proteins. The flow-through fraction was collected into a polypropylene conical tube (Sarstedt, #72.692), and cooled to 4° C. using the thermostat-controlled fraction collector.

Processing of Depleted Serum and Bound Fractions for Electrophoretic Analysis

Flow-through fractions or bound fractions from several injections were pooled and buffer-exchanged in 4 mL spin concentrators with 5 kDa molecular weight cutoffs (Agilent Technologies, #5185-5991). The sample was centrifuged at 7,500×g for 20 minutes at 4° C. Buffer was exchanged into 20 mM Tris-HCl, pH-7.4 by 3 rounds of addition of the buffer, with centrifugation for 20 minutes each time. The concentrated samples were aliquoted and stored at −70° C. until analysis. Protein concentrations were analyzed using a BCA protein assay kit (Pierce, #23225).

Liquid Chromatography

HPLC was performed on an automated Agilent 1100 LC system (Chemstation A.10.01 software) using standard configurations with operation at ambient and elevated temperatures. The LC station components included a binary pump, degasser, solvent cabinet, autosampler (900 μL loop) with thermostat, diode-array detector (280 nm) with 6 mm flow cell, column oven and analytical scale thermostat-controlled fraction collector. The LC system set-up allowed automated separations of multiple samples and fulfilled necessary requirements such as monitoring, precise fraction collection, injection and cooling of injected and collected samples. A reversed-phase 5.0 μm particle diameter superficially porous C18 resin was prepared and packed into 2.1×75 mm, 4.6×50 mm and 9.4 mm×50 mm stainless steel HPLC columns. Alternatively, for comparative purposes, a column of 4.6×50 mm Zorbax 300SB-C8 (totally porous, 300 Å pore diameter, 5 μm particle diameter) was employed. In embodiments, the protein separation methods of the present disclosure can be accomplished at elevated temperatures by an RP-HPLC system having a superficially porous phase, for example, as illustrated herein. In embodiments, the RP-HPLC system can include, for example, a pressure restrictor, or like devices or apparatus that can prevent or minimize solvent(s) boil-off to maintain the performance characteristics of the mobile phase and the integrity of the separation method.

In embodiments, the protein separation methods of the present disclosure can be accomplished using a superficially porous phase at elevated temperature and which elevated temperature can be maintained relatively uniform, that is substantially isothermally, throughout the superficially porous phase separation, such as at a temperature or temperature range as illustrated herein, and having a temperature variation of, for example, from about plus or minus 10° C., from about plus or minus 5° C., from about plus or minus 2.5° C., from about plus or minus 1.0° C., or from about plus or minus 0.5° C.

HPLC Sample Preparation, Separation and Fraction Collection 1.0 mL immunodepleted human serum flow-through fractions containing approximately 380 µg protein (0.25 µg/µL) were added to 480 mg of solid urea and dissolved to a final volume of 1.3 mL. After dissolution, 13 µL AcOH was added (final concentration equal to 6 M urea/1.0% AcOH) and the samples stored at −80° C. Immunodepleted serum flow-throughs in 6 M urea/1.0% AcOH were pooled as needed and injected onto 4.6×50 mm or 9.4×50 mm superficially porous particle columns for fraction collecting. Separations were performed using a stepwise gradient elution, with buffer A, 0.1% TFA in water and buffer B, 0.08% TFA in acetonitrile. The step gradient consisted of three steps with increasing concentrations of buffer B in buffer A: 3-30% B 6 min., 30-55% B 33 min., 55-100% B 10 min., hold 100% B 4 min. at a flow rate of 0.75 mL/min for a total runtime of 54.0 min. During consecutive runs, a 5.0 min. post run comprising of 3.0% buffer B was added to re-equilibrate the column. For performing multiple flow-through injections of 900 µL, a 1.0 min. gradient delay was added to allow the injector loop to empty prior to the next injection. The chromatograms were monitored at 280 nm and 50 fractions collected at 1.0 min. intervals from 3.0-53.0 min. Each fraction was dried in a speed vacuum concentrator and stored at −80° C. for LC/MS/MS and 1D SDS-PAGE analysis.

Electrophoretic Analysis

1D SDS-PAGE analysis was carried out using Invitrogen Tris-glycine precast gels (4-20% acrylamide, 10 wells, 1 mm, #EC6025BOX) according to the manufacturer's protocol. Proteins were visualized by Coomassie Blue staining with GelCode Blue (Pierce, #24592).

Protein Recovery

200 µg of denatured immunodepleted human serum was separated on a superficially porous C18 column under the gradient elution conditions described in the above HPLC sample preparation, separation and fraction collection section. The column eluent was collected into 50 mL polystyrene conical tubes (BD #352073). Blank runs were performed in the same manner, however, with the column removed. The blanks were collected before and after the column recoveries. Blanks and column eluates (approx. 38 mL) were dried in a speed vacuum concentrator at medium drying temperatures overnight.

Dried samples of column and blank runs were solubilized with 0.5 mL of 3M Urea, 1% Triton X-100 and 0.25% acetic acid. The final urea concentration, including the urea present from the injected sample, was 5.5 M. Samples were extensively vortexed to solubilize all protein from the tube walls. Protein quantitation was performed with EZQ Protein Quantitation kit (R 33200) from Molecular Probes. An Ovalbumin standard was used for the creation of a least-squares fitted standard curve. 1 µL of each sample was spotted on assay paper; the samples were fixed, washed and stained with EZQ stain according to the manufacturer's protocol. Each sample was then processed in quadruplicates and fluorescence was measured by scanning the paper on a Typhoon 8600 laser scanner (Amersham) using a 532 nm laser for the excitation and 580 nm emission filter.

LC/MS/MS

The RP protein fractions were lyophilized and re-dissolved in 100 mM ammonium bicarbonate, 8 M urea, pH 8.5 and digested with Lys-C and trypsin (suitable REFs). The digestion reaction was quenched with the addition of 3 µL acetic acid. The entire digestion solution, from each individual RP fraction (~70 µg for the depleted serum), was loaded on a serially connected RP-SCX column (Agilent Zorbax 300SB-C18, 5 µm, 35×0.3 mm and Agilent Zorbax BIO-SCX II, 3.5 µm, 35×0.3 mm) offline using an Agilent 1100 HPLC (Agilent, Palo Alto, Calif., USA). The two-phase column was then connected to a capillary RP column (Agilent, Zorbax 300SB-C18, 3.5 µm, 150×0.1 mm) and was analyzed by 2D LC-MS/MS using an Agilent nano-LC-MS system (Agilent 1100 Nano-LC and Agilent XCT ion trap). Peptides were first eluted to the SCX column from the first RP phase column with high organic solvent content. Then 10 salt steps were used at following concentration of ammonium acetate: 10, 25, 50, 100, 150, 200, 300, 400, 500, 1,000 mM (REFs), about 2 hours for each step. An XCT ion trap was operated in standard scan mode for MS analysis and in ultra-scan mode for MS/MS.

The MS/MS data were analyzed with Spectrum Mill (Agilent, Palo Alto, Calif., USA) against NCBI non-redundant human database. The following filter was used after database searching: peptide score >8, peptide % SPI >70 and protein score >9. Only fully tryptic peptides were considered with one mis-cleavage allowed.

Referring to the Figures, FIGS. 1 and 2 are discussed in Examples 1 and 2, respectively, below.

Figure 3:
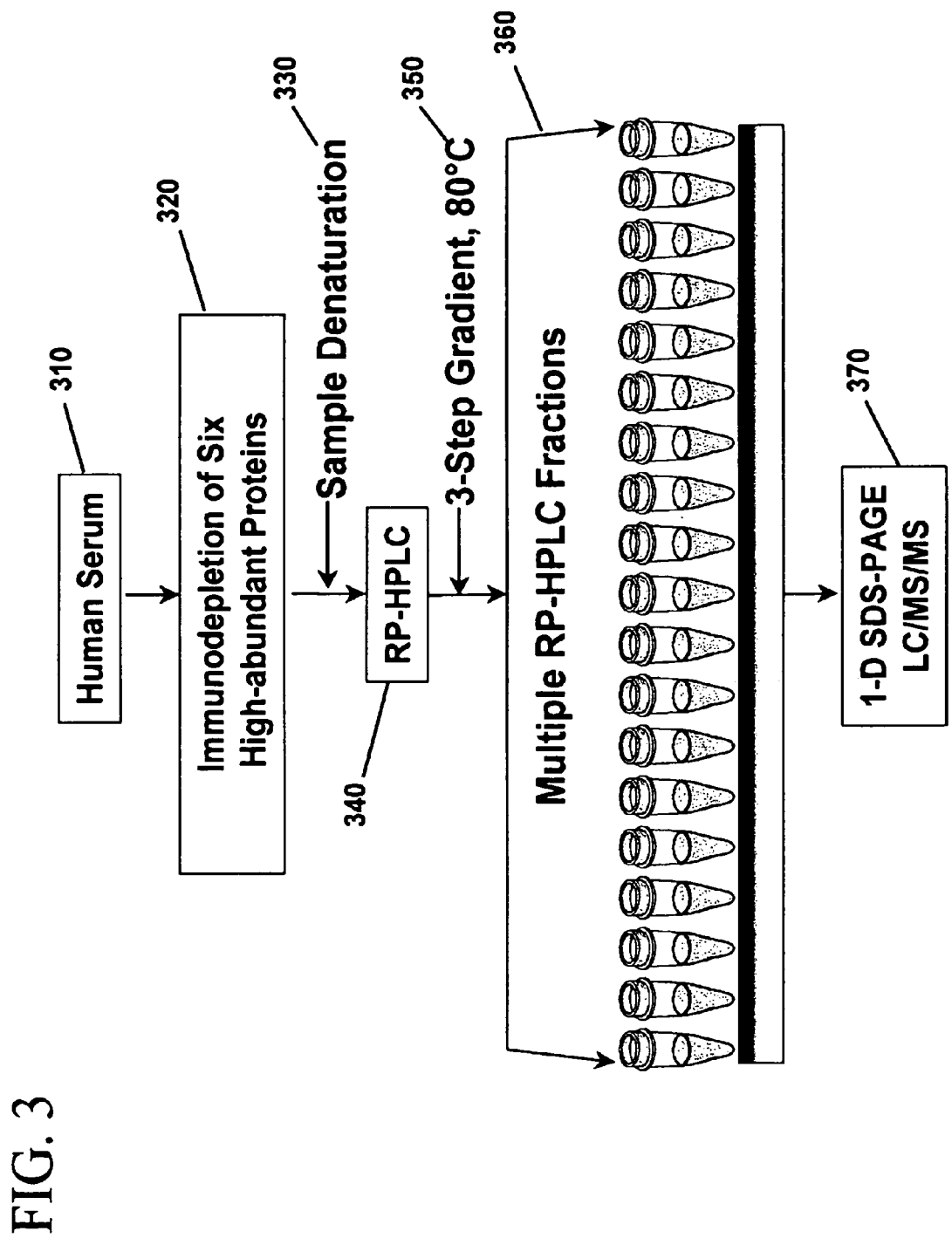
FIG. 3 illustrates an exemplary workflow schematic, in embodiments of the present disclosure.

FIG. 3 illustrates an exemplary workflow schematic where, for example, a human serum sample (310) is immunodepleted (320) of, for example, its six most abundant protein constituents, followed by sample denaturation (330), RP-HPLC (340), having a 3-step gradient at elevated temperature (350), such as 80° C., to afford multiple RP-HPLC fractions (360) which can be further analyzed by, for example, 1D SDS-PAGE LC/MS/MS (370).

Immunoaffinity Serum Depletion

Figure 4A:
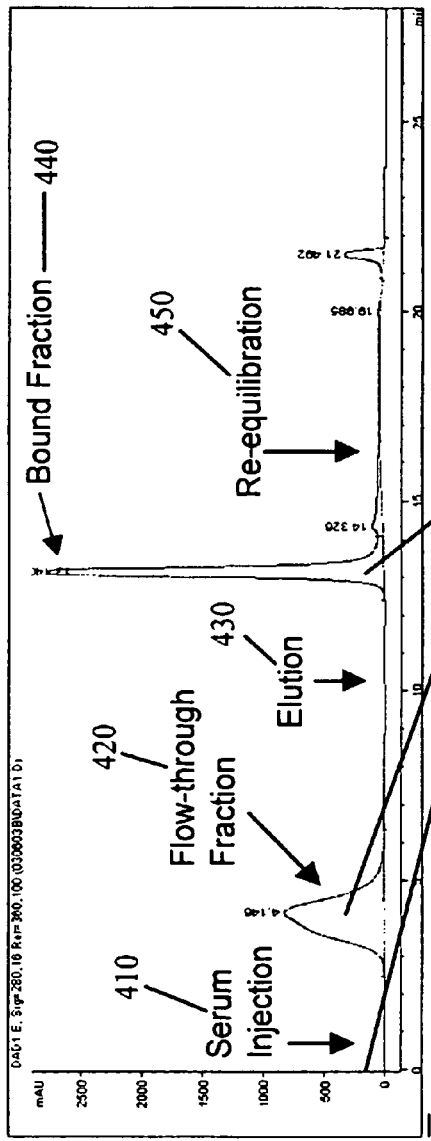
FIG. 4A-4B illustrate an exemplary chromatogram and a 1D SDS gel electrophoresis for affinity high-abundance protein depletion from human serum, respectively, in embodiments of the present disclosure.
Figure 4B:
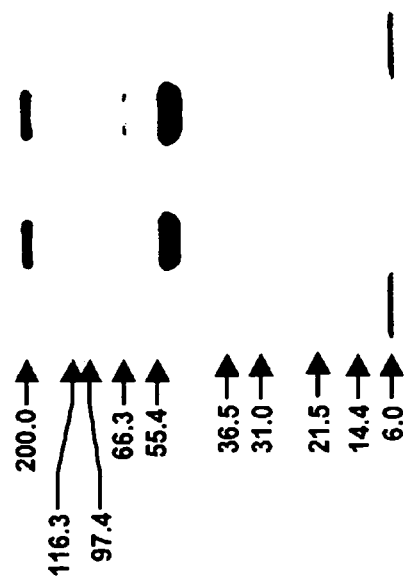

FIGS. 4A and 4B illustrate an exemplary chromatogram and 1D SDS gel electrophoresis for affinity high-abundance protein depletion from human serum, respectively. In FIG. 4A, 36 µL of serum were diluted 5× and injected (410) on a 4.6×100 mm immunoaffinity column (0.50 mL/min). A flow-through peak (3-5.0 min) (420), depleted of the top six high-abundant proteins, was collected for reversed-phase HPLC fractionation. The column was then washed with Buffer B (430) and the bound top six high-abundant proteins (440) eluted and discarded. The column was re-equilibrated with buffer A (450) for repeated use. In FIG. 4B, an equal amount (10 µg) of crude serum (Lane 2), flow-through (Lane 3) and bound fractions (Lane 4) were separated on 4-20% SDS-PAGE under non-reducing conditions. Lanes 1 and 5 are the molecular weight standards (Mark12) from Invitrogen. Based on the protein assay of the flow-through fraction, 85% of total protein was removed from the crude serum. FIG. 4A shows removal of highly abundant proteins from a human serum sample. Ideally, in embodiments, a depletion column should possess little or no binding of non-targeted proteins, and preferentially should bind several high-abundant proteins simultaneously. Antibody-based selection strategies can offer the desired characteristics, since immunoaffinity separations are known to be capable of excellent specificity and acceptable sample capacity. An SDS-PAGE analysis of the flow-through and bound fraction indicates high specificity for the removal of the abundant proteins (FIG. 4B, Lane 4) and enrichment of low-abundant proteins in the flow-through fraction (FIG. 4B, Lane 3). By removing high-abundant proteins, it was possible to reduce the total serum protein mass by 85%. From each column pass, 0.38 mg of low-abundant protein was collected in the flow-through fraction, depleting about 2.14 mg of high-abundant proteins from 36 µL of injected human serum. Flow-through fractions were processed as needed for the down-stream separation by RP-HPLC (see material & methods). The samples were added directly to the denaturant (acidic urea or guanidine hydrochloride) and required no other post depletion processing prior to reversed phase HPLC.

Ordinarily, immunodepleted serum samples require added steps to desalt and/or concentrate prior to electrophoretic and mass spectral analyses. More common techniques and procedures rely on the use of membrane filters, dialysis, and spin concentrators. However, using these methods also increases the chances for protein precipitation and losses due to irreversible membrane binding. HPLC sample clean up is a well-known and commonly practiced technique and can be used as a desalting step prior to the start of the separation. By direct HPLC injection of flow-through, without additional desalting, new protein identifications were made with the appearance of new 1D gel bands not previously detected when using a spin concentrator to desalt. In addition, immunodepleted flow-through fractions could be concentrated on the column through multiple injections and a delayed response gradient. This permitted a one-time reproducible separation for any given columns loading capacity.

Figure 5A:
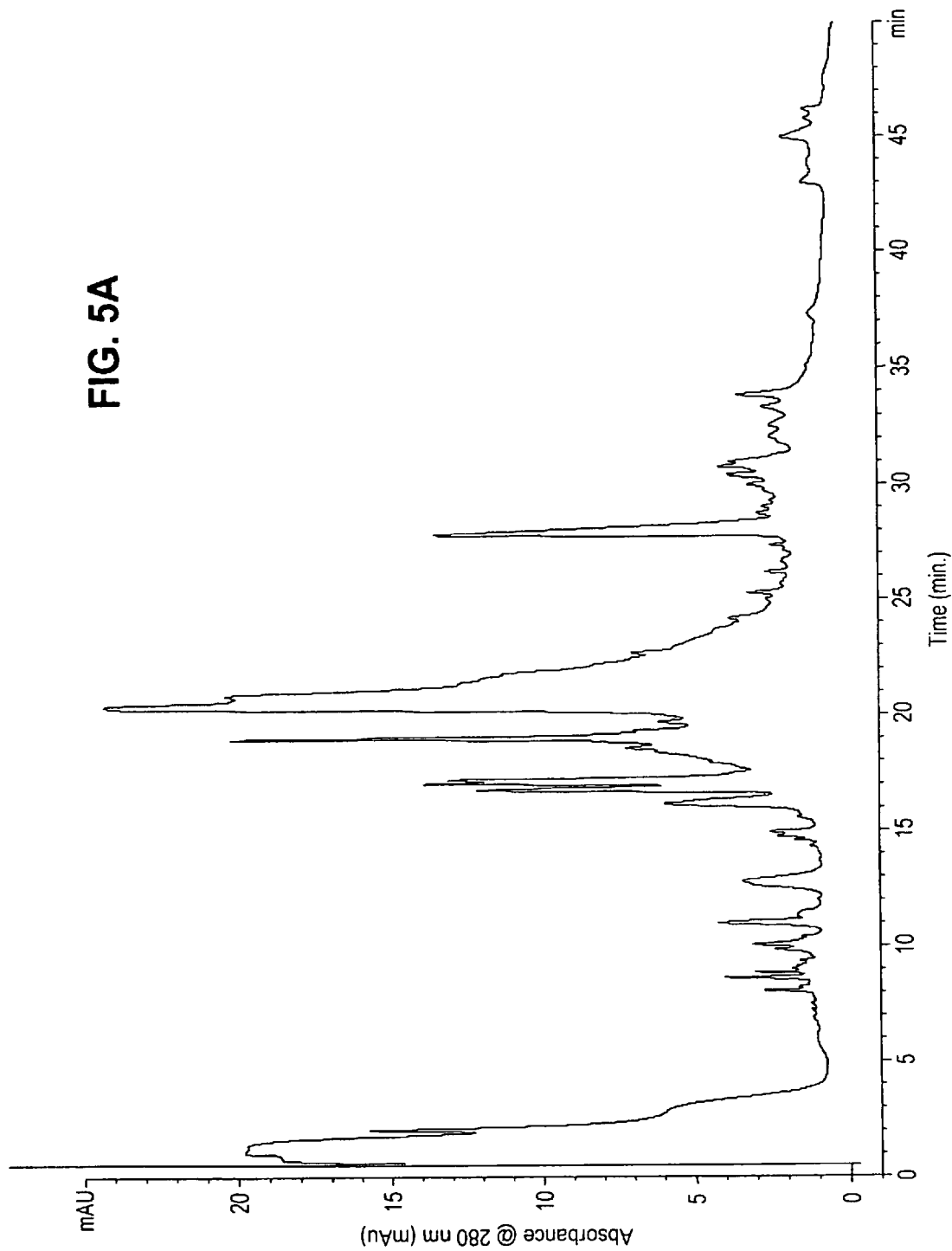
FIG. 5A-5B illustrate a comparison of the RP-HPLC elution profiles for crude human serum (A) and human serum depleted of high abundant proteins (B), respectively, in embodiments of the present disclosure.
Figure 5B:
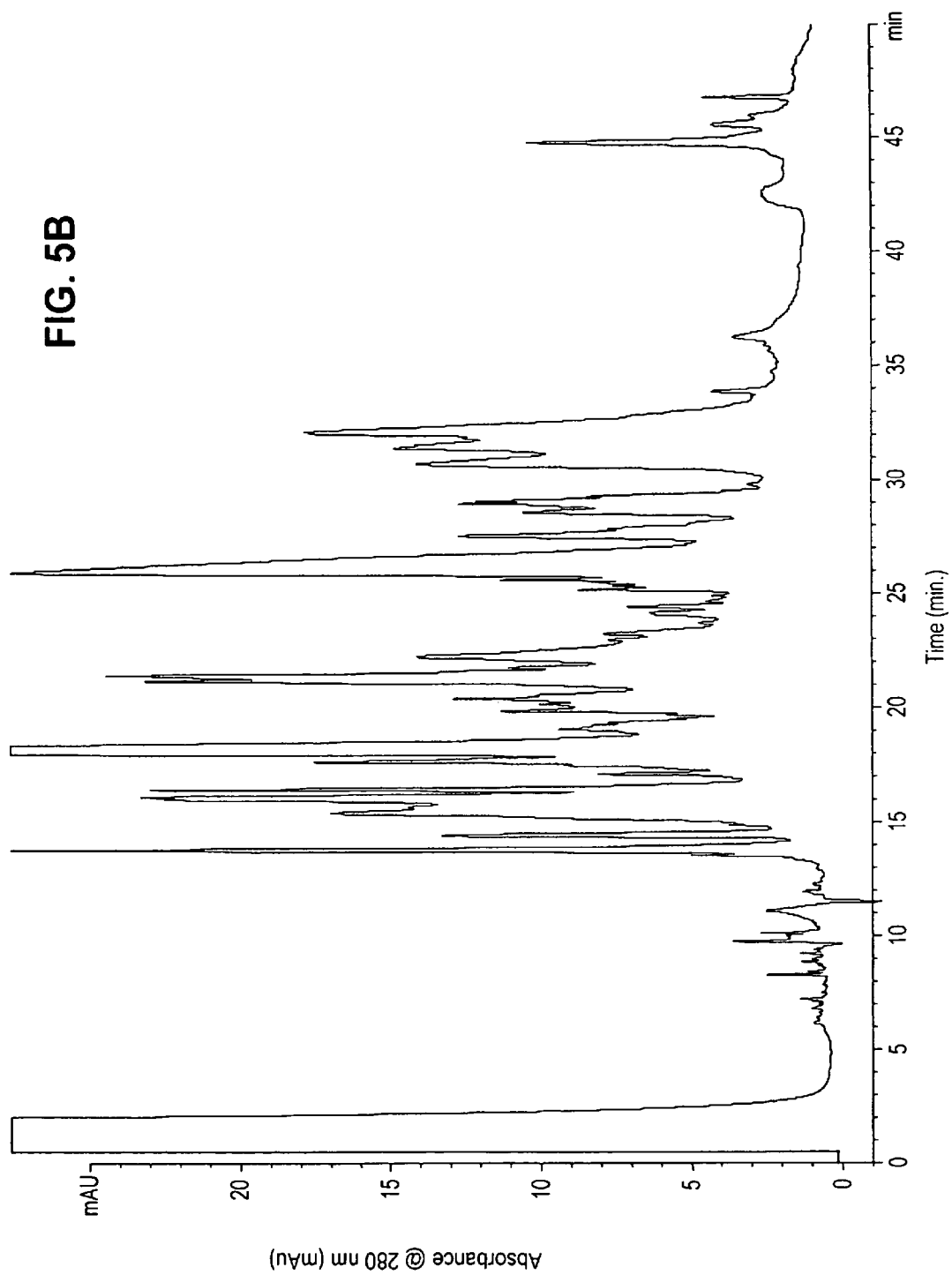

FIGS. 5A-5B illustrate a comparison of the RP-HPLC elution profiles at a wavelength of 280 nm for crude human serum (A) and human serum depleted of high abundant proteins (B), respectively. An aqueous TFA and ACN (TFA) gradient was run at 80° C. at a flow rate of 0.75 mL/min on a 4.6×50 mm macroporous column. Each sample comprised a total of 270 µg protein in 6 M urea/0.1% AcOH. However, the depleted serum sample also contained the flow-through salts present from the immunodepletion process. Representative chromatograms comparing a reversed-phase separation of whole human serum versus immunodepleted serum are shown in FIGS. 5A and 5B. The reversed phase separation in FIG. 5A was performed without an immunodepletion step. The separation is poorly resolved and overloaded, clearly demonstrating the need for a reduction in sample complexity. The chromatogram shown in FIG. 5B is a reversed phase separation in which the serum sample has been depleted of the top six most abundant proteins—HSA, IgG, IgA, Haptoglobin, Transferrin and Alpha1-antitrypsin. When contrasted against the non-immunodepleted chromatogram of FIG. 5A, the FIG. 5B immunodepleted chromatogram displays a highly resolved separation with improved sensitivity for proteins otherwise obscured by overly abundant proteins.

Reversed-phase Column Performance

Conventional reversed-phase column materials and the operational conditions under which they are used to prefractionate, have produced encouraging results to further reduce sample complexity and thus unmask lower abundant proteins. However, the use of RP chromatography doesn't come without some trepidation. In a current review on chromatographic prefractionation methods, Pierre Lescuyer et al., describe the utility of RP chromatography to prefractionate complex protein mixtures. The authors describe the importance of RP-HPLC for obtaining high-resolution separations during fraction collection, but caution against the protein losses commonly associated with this analytical technique. See, e.g., Lescuyer, et al., *Electrophoresis*. 2004 April; 25(7-8): 1125-35.

A reversed-phase superficially porous column packing material (mRP-C18) was studied and conditions developed for the prefractionation of immunodepleted serum. The column was evaluated for separation characteristics, recovery, capacity and reproducibility. To emphasize areas of enhanced column performance, the results obtained were contrasted with those obtained from a more traditional porous reversed phase column material.

First, the mRP-C18 was investigated for its ability to separate immunodepleted human sera. Of particular interest, were the conditions needed to achieve a separation in which the serum depleted proteins were uniquely resolved to confine remaining higher abundant proteins into concise fractions, while also providing maximum band spacing for reducing sample complexity. To accomplish this objective, temperature and gradient conditions were investigated and novel conditions identified. Results were compared against those performed on a totally porous column under the same or similar conditions.

Figure 6A:
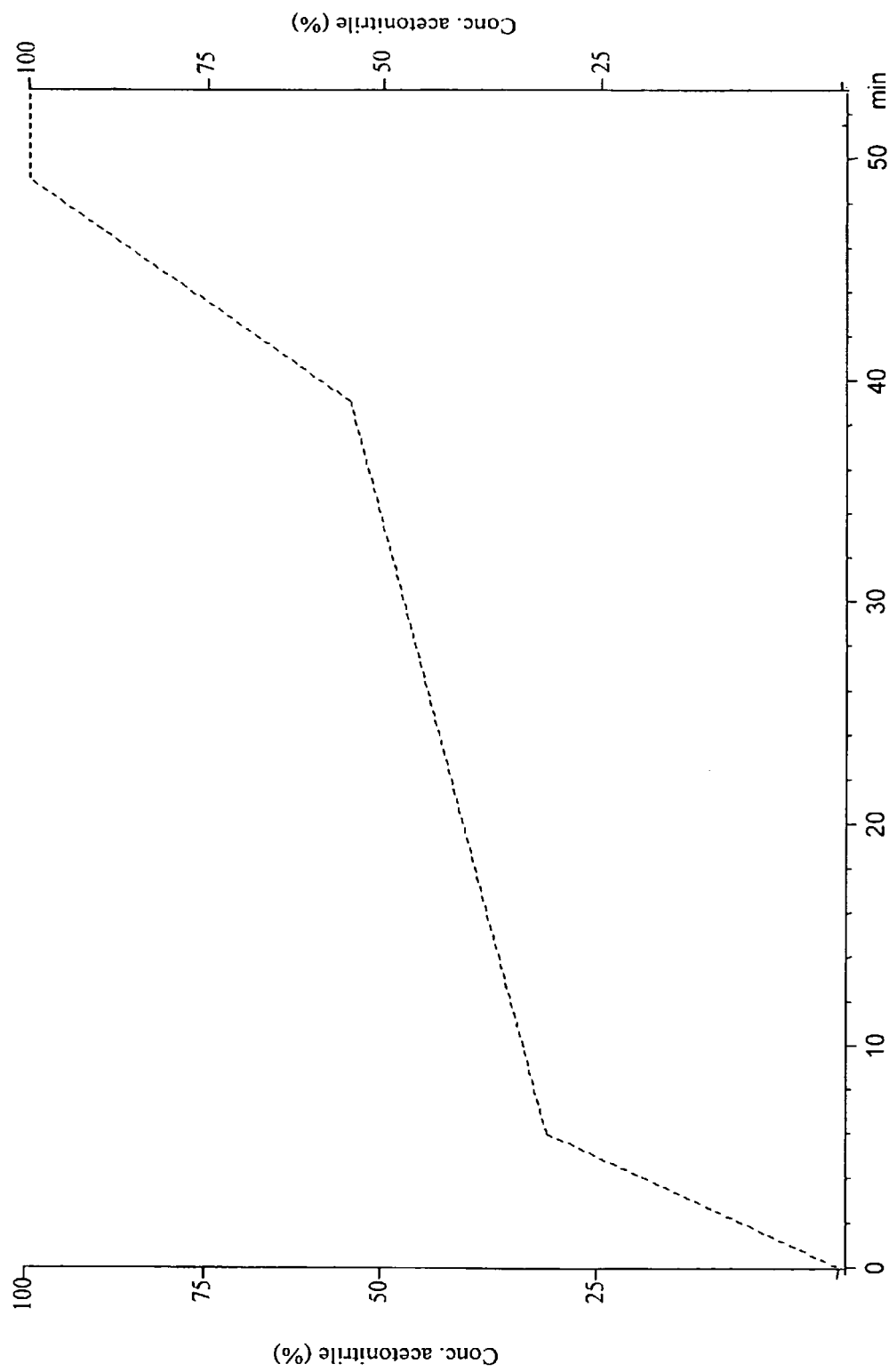

FIGS. 6A-6C illustrate the effect of temperature on chromatographic separation using a 3-step gradient elution on a macroporous C18 (4.6×50 mm) support or stationary phase. In FIG. 6A, the step gradient elution conditions at a flow rate of 0.75 mL/min were 4.5% eluent B/min from 3-30%, 0.76% B/min. from 30-55%, 4.5% B/min. from 55-100%, 100% B 4 min. FIG. 6B shows RP chromatographic separation at ambient temperature (26° C.) and of Apolipoprotein A1 (650). FIG. 6C shows the details of the enhanced resolution and selectivity gains for α-1-acid glycoprotein (660), Apolipoprotein A1 (670) and Complement C4 (680) when the same RP-HPLC separation is performed at elevated temperatures (e.g., 80° C.). The arrows indicate the presence of protein identified by 1D-SDS-PAGE analysis. The mobile phase A can be, for example, from about 0.01 to about 2 weight % trifluoroacetic acid in water. Eluent B can be, for example, from about 0.01 to about 2 weight % trifluoroacetic acid in acetonitrile. Gradient elutions can be accomplished with, for example, various specified combinations or mixtures of mobile phase A and eluent B.

mRP-C18 separations were performed at increasing temperatures of 26°, 65°, and 80° C. As temperatures were elevated, chromatographic performance became enhanced. In contrast to separations performed at ambient temperature, separations at 70° and higher show enhanced protein selectivity and a modest shift towards higher resolution. For example, FIGS. 6B and 6C show two gradient separations on mRP-C18 at 26° C. and 80° C., respectively. Selectivity for Complement component C4 and α-1-acid-glycoprotein has been lost at 26°. In addition, Apolipoprotein A1 is less resolved and has shown a large degree of tailing as further revealed by a 1D-SDS PAGE analysis of the entire separation. Also at 80° C., the macroporous column remained stable and gave no indications of deterioration after 50 column run cycles.

A second important parameter for reversed-phase separation, was determining a set of elution conditions for delivering a highly resolved separation of hydrophilic and hydrophobic co-eluting serum proteins, with the goal of obtaining a broad distribution of the immunodepleted serum proteins. Enhanced resolution permits unmasking of low-abundant proteins for enhanced LC/MS identifications.

Initial gradient investigations began with depleted serum flow-throughs denatured in 6 M guanidine hydrochloride. As gradient work progressed, a switch was made to 6 M acidic urea as the denaturant. The driving factor behind the switch was to first compare any denaturant effects on the separation, and second to consider the possible downstream effects guanidine would have SCX fractions for 2D LC/MS/MS analysis. Chromatographic runs independently using the two different denaturants, under the same conditions, had little effects on the separation. The resolution remained comparable and sensitivities went unchanged. However, the downstream effect from using guanidine hydrochloride created some problems during the off-line SCX separation. Although not desired to be limited by theory, it was initially postulated that guanidine would be removed as a salt plug in the beginning of the separation, however, fouling of the off-line SCX separation, prior to LC/MS, suggested salt contamination in each of the collected fractions.

Figure 7:
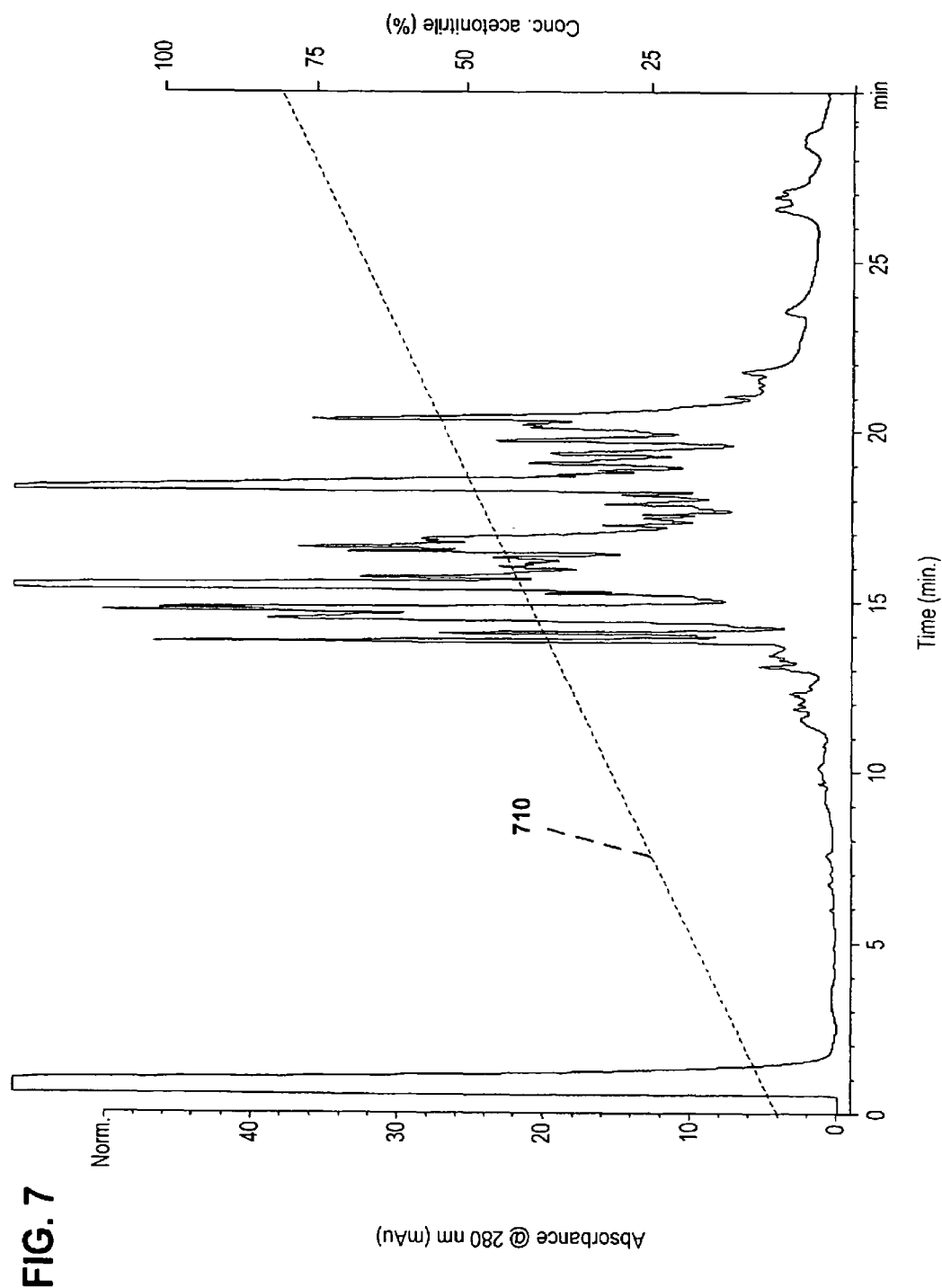
FIG. 7 illustrates a representative RP-HPLC elution profile of immunodepleted human serum obtained when using linear elution conditions, in embodiments of the present disclosure.

FIG. 7 illustrates a representative RP-HPLC elution profile of immunodepleted human serum obtained using linear elution conditions, for example, increasing concentrations of acetonitrile (TFA) on a 4.6×50 mm macroporous C18 column. The dotted line (710) gradient represents increasing amounts of 2.3% eluent B/min from 10 to 80%. Gradient methods were evaluated (80° C.) by changing the water/acetonitrile (TFA) gradient, denaturant, acid modifier (TFA), and flow rate. Beginning with linear elution gradients of aqueous TFA and ACN (TFA), the depleted serum separations did not deliver the broad peak distribution preferred for optimal fraction collecting. As shown in FIG. 7, the majority of hydrophobic proteins eluted within a narrow range of increasing organic concentration. Systematically lowering the gradients and extending the run times to widen peak profiles also produced peak overlapping and less than desired separations. Upon further inspection of the linear elution profile, it was determined that the majority of proteins were rapidly eluting within 30-50% of ACN. Incrementally lowering the gradient within this region provided for higher selectivities and enhanced resolution. In combination with an initial and final linear steep gradient slope and a 100% isocratic hold of acetonitrile (for facilitating protein desorption), the 3-step gradient improved column performance and provided a much broader separation more amenable to fractionation (as discussed with respect to FIGS. 6A and 6C above).

Systematic changes of the TFA modifier were introduced for both the water and ACN mobile phases. Increases in the starting TFA concentrations were varied from 0.1% to 0.5% for water and 0.08% to 0.4% for ACN. The changes showed little selectivity effects on the retention behavior of the depleted serum sample, and although some shifts occurred, differences in TFA concentration did not improve or dramatically change the separation behavior. TFA amounts were therefore kept at the original concentrations of 0.1% for water and 0.08% for ACN.

FIG. 8 illustrates an SDS-PAGE analysis of a HPLC fractionated immunodepleted human serum obtained from a reversed-phase macroporous column (9.4×50 mm, 5 μm particle diameter). 1,350 μg of depleted serum sample was injected onto the column and eluted by a 3-step gradient (see FIG. 6A). The collected fractions were dried and dissolved in SDS sample buffer and loaded onto a 4-20% SDS-PAGE. The gel, of fractions 7 through 46, was stained with Coomassie Blue. Lane 1 represents the Invitrogen markers in kDa. Visualization of 1D gel patterns was used as another gauge to measure separation efficiency of the fractionated proteins. Examination of band patterns can determine the effectiveness, or ineffectiveness, of the separation based on band repetitions across gel lanes or lack thereof. Band intensities can also give an indication of column capacities by the extent of their carryover from one lane to another as mentioned further below. As shown in FIG. 8, fractions collected from a mRP-C18 immunodepletion separation are limited in band redundancy for the regions of the chromatogram where protein separation and UV signal were greatest. Fractions 9-30 are representative for the 12-33 minute region of the chromatogram in FIG. 6C. The gel patterns within this region highlight the separation efficiency of abundant proteins and reveal many distinct and unique bands that would otherwise be obscured.

The combination of chromatography with an electrophoretic analysis has enabled a more thorough approach to define the efficiency of the total serum separation for fractionating, rather than relying on the chromatographic data independently.

Figure 9A:
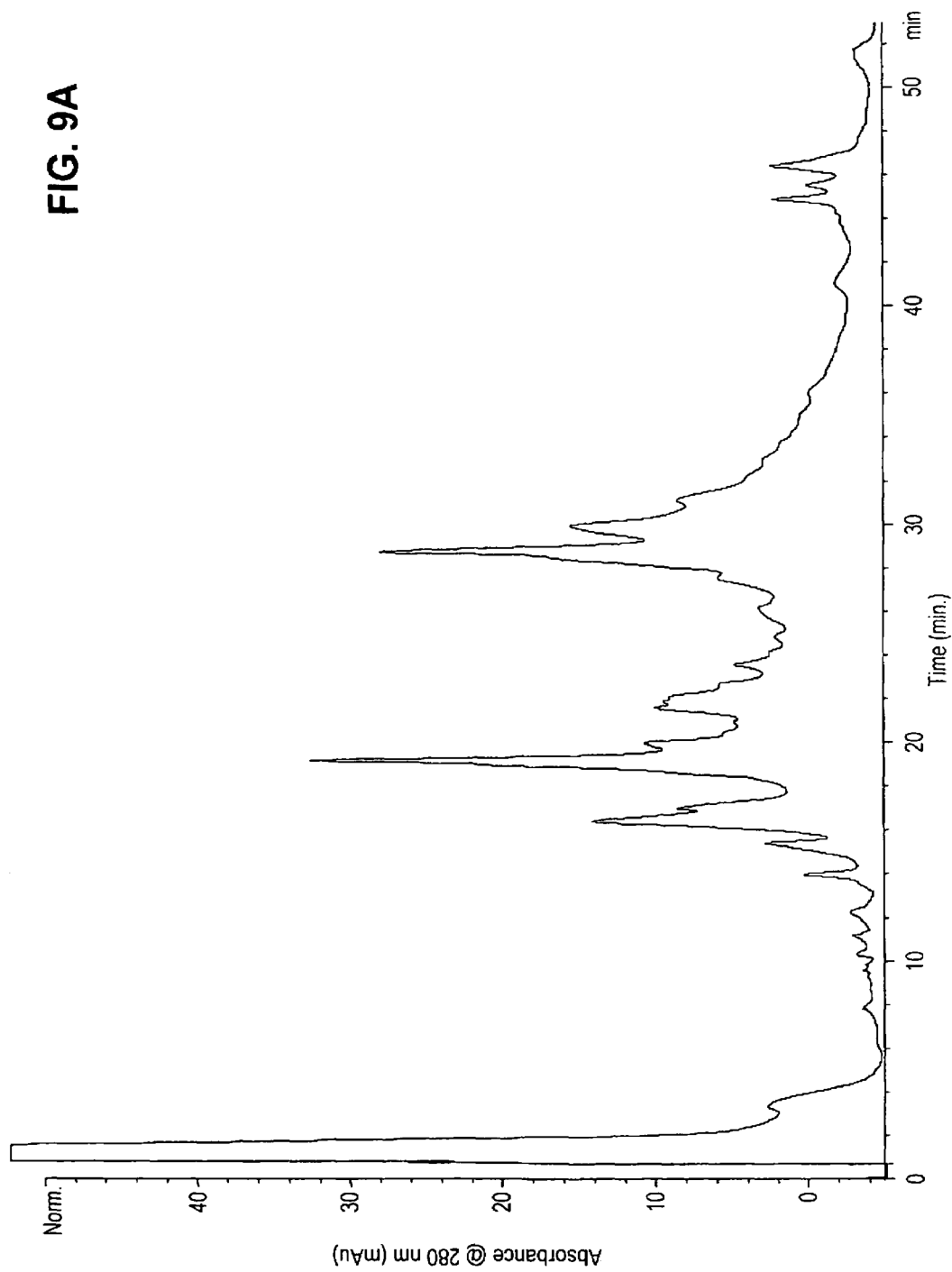
FIG. 9A-9B illustrate a 300SB-C8 HPLC separation of immunodepleted human serum, and an electrophoretic analysis of the resulting fractionated immunodepleted human serum, respectively, in embodiments of the present disclosure.
Figure 9B:
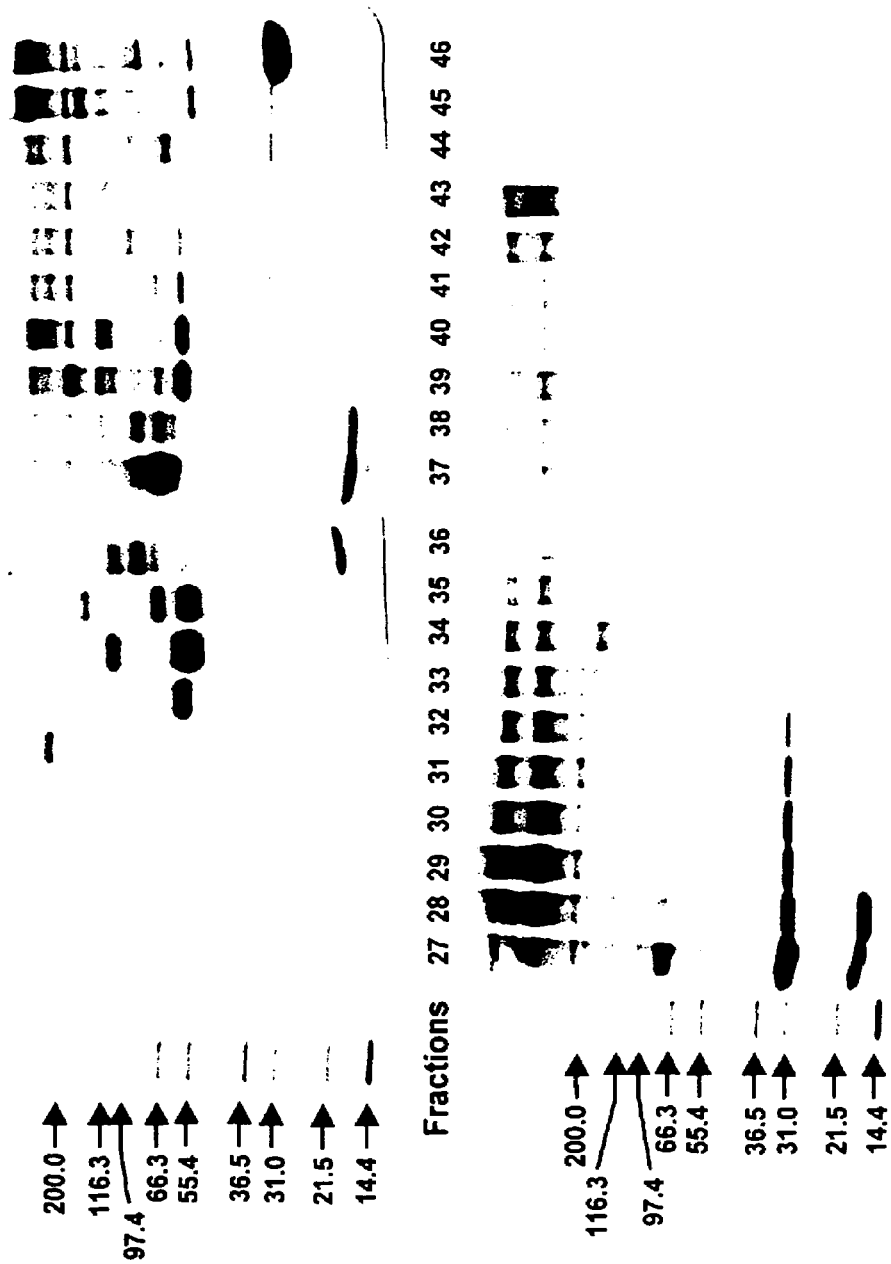

With these criteria, the separation efficiency between porous and non-porous phase types was evaluated. The chromatographic performance of immunodepleted human serum was evaluated on a conventional porous column under the conditions described above. FIG. 9A illustrates a RP-HPLC separation of 270 μg immunodepleted human serum performed on a 4.6×50 mm Zorbax 300SB-C8 (300 Å, 5 μm particle dia.) under the conditions described for FIG. 7. FIG. 9B illustrates an electrophoretic analysis of the resulting fractionated immunodepleted human serum presented in FIG. 9A. The collected fractions were dissolved in SDS sample buffer and loaded onto a 4-20% 1D SDS-PAGEPA gel. The gel was stained with Coomassie Blue. The chromatographic performance, shown in FIG. 9A, displayed a significant loss in protein retentions characterized by the poor resolution of both hydrophobic and hydrophilic proteins. Upon comparing regions of hydrophilic protein elution (0-14 minutes) for the mRP-C18 and porous chromatograms (FIGS. 7B and 9A), the porous separation showed a loss of resolution and peak shifting to areas of higher protein abundance. Likewise, the elution profile for hydrophobic proteins became even more dramatic in terms of resolution. As shown in FIG. 9A there was diminished peak fine structure and significant losses in selectivity.

To electrophoretically contrast the extent of separation efficiency between the two column types, 39 fractions were collected from the porous column at the same time intervals as the mRP-C18. Next, a 1D SDS-PAGE was performed, shown in FIG. 9B, and the band patterns compared in Fractions 9-30 which constitute the region of highest protein elution. The porous column gels revealed similar high abundant proteins bands within each fraction, however, the bands were carried across many more gel lanes and showed a pattern of repeating intensities.

One of the important attributes of a reliable, complex sample separation is the ability to recover injected material. RP-HPLC protein recoveries accomplished at ambient and elevated column temperatures were compared. In order to calculate the recoveries with the developed HPLC separation protocol, a series of injections of the immunodepleted serum with and without (blank) the reversed phase column were performed. Chromatographic fractions were pooled and processed according to the procedure described herein. Recovery values were normalized against sham injections (no column present), which were considered as 100% recovered. A solid-phase, fluorescence-based protein assay (EZQ Protein Quantitation Kit, Molecular Probes, cat # R33200) was used to quantify proteins in the presence of detergents and urea among other interfering agents. The compatibility and quality of this method ensured accurate protein quantitations and supplemented preliminary BCA (Pierce) findings.

As shown in Table 1, recovery values for the mRP-C18 and totally porous columns were similar. The reversed phase separations performed under elevated temperature, specifically 80° C., provided near quantitative recovery of the injected immunodepleted serum. In contrast, separations performed under room temperature conditions yielded much poorer recoveries, resulting in approximately 30% of total protein losses. Post column blank runs performed during gradient investigations showed significant peak "ghosting" (i.e., UV absorbing eluting materials) after the completion of each run at room temperature.

TABLE 1

Protein recoveries from reversed phase separation.

| Separation Media | % Recovery, 80° C. | % Recovery, 20° C. |
| --- | --- | --- |
| Superficially Porous C18 | 103.0 ± 5.6 | 70.5 ± 0.4 |
| Fully Porous 300 C8 | 99.1 ± 2.6 | 70.2 ± 6.9 |

Gradient separations completing at 80% acetonitrile, routinely used for protein and peptide separations, gave repeated and consistent losses of 15-20% of protein. Over time these adsorbed and bound proteins can degrade the reproducible performance of reversed phase columns and require column replacement. Typically, column-cleaning methods are sometimes used, such as washing with solutions containing trifluoroethanol or guanidineHCl, to remove hydrophobic or membrane proteins, however, this serves only as a provision to extended column life, and does not address poor recovery performances. It was found that by completing the gradient with 100% acetonitrile, and holding for a short period of time, it was possible to regenerate the column surface free of absorbed proteins and obtain recoveries to near quantitative values, without any evidence of protein precipitation or compromises to downstream analyses. However, performing reversed-phase separations at high organic solvent content is a potential concern with respect to undesired protein precipitation. No evidence of precipitation or protein loss was observed and it is believed that the combination of high temperatures, low mobile phase pH, and acetonitrile as the organic modifier, maintain all or most of the proteins' solubility, without any compromises to column stability.

Loading larger amounts of protein makes it possible to detect and characterize proteins that were below the detection limit threshold for MS analysis. Increased protein loads improve the quality of MS data both in terms of peptide sequence coverage and quality of the spectra (signal-to-noise). The increased protein loads also aid in visualization of low abundant serum proteins in 1D & 2D gel electrophoresis. The criteria to determine column capacities for such a complex separation was to minimize band broadening and maintain selectivity for high abundant proteins. The uppermost capacity at which fractionation caused band repetition across 1D gel lanes was determined and found to be similar to the criteria used for electrophoretic evaluation of column resolution. The 4.6×50 mm mRP-C18 had a fractionating capacity of 400 μg protein and the 9.4×50 mm column afforded capacities in the range of 1,400-1,600 μg of protein. The same capacity study was also performed on a porous column. Capacities within the same column dimensions were recorded at less than 5 times the capacity for the mRP-C18 column. The mRP-C18 displayed better resolution and showed significantly less band broadening than the porous column.

Finally, under the conditions disclosed herein, the mRP-C18 column was evaluated for reproducibility. Chromatographic separations combined with an electrophoretic analysis of the separation can detail the precision and accuracy of the repeated separation.

Figure 10B:
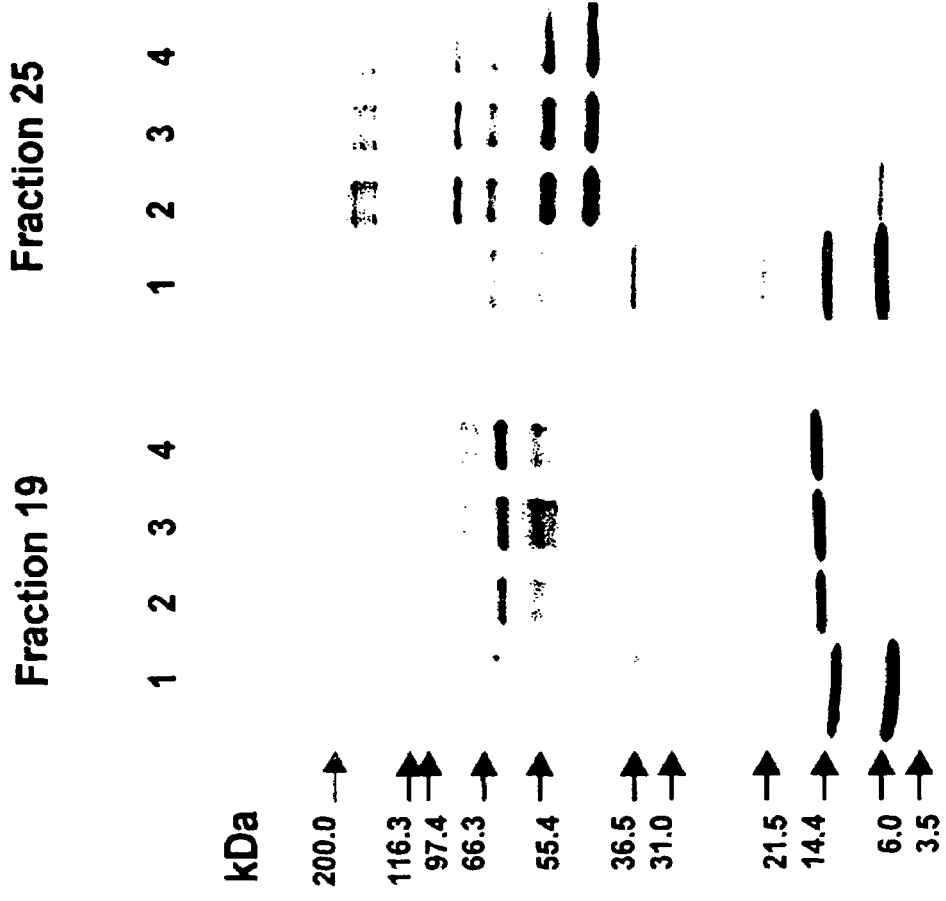

FIG. 10A illustrates a composite overlay of chromatograms from four reversed-phase separations (runs 1 (1030), 2 (1040), 3 (1050) and 4 (1060)) of immunodepleted human serum on a 9.4×50 mm macroporous column. 1,080 μg of depleted serum in 6 M urea/0.1% AcOH was separated in each run under the conditions described in the above "HPLC sample preparation, separation and fraction collection" section. The shaded regions represent areas of fraction collection, fraction 19 (1010) and fraction 25 (1020), for 1D-SDS PAGE reproducibility analysis. FIG. 10B illustrates a 1-D gel analysis of fractions 19 and 25 from the reversed-phase separation shown in FIG. 10A. Each of the collected fractions were dissolved in SDS sample buffer and loaded onto a 4-20% SDS-PAGE. Lane 1 represents the Invitrogen markers. Lanes 2, 3, and 4 represent fractions 19 and 25 from each of runs 2, 3 and 4 shown in FIG. 10A.

Multiple separations of immunodepleted serum samples were performed by collecting precise fraction slices from each run. FIG. 10A details the chromatographic reproducibility of 4 consecutive immunodepleted serum separations. The UV trace at 280 nm showed no changes from run to run and the peak intensities remained identical and overlapping. In addition, there did not appear to be any shift in retention times for any of the peaks fine structure. FIG. 10B details the reproducibility of the separation by comparing two randomly selected fractions. The gel patterns for fractions collected at equivalent time slices appear identical in both pattern and band intensity.

2D LC/MS/MS

FIG. 11 illustrates a superficially porous particle RP-HPLC separation of immunodepleted human serum (1,350 μg) under gradient conditions disclosed herein on a 9.4×50 mm mRP-C18 column, with fractions collected for subsequent protein identification using two dimensional LC/MS/MS analysis. The shaded regions represent fractions chosen for 2D LC/MS analysis. The 1D SDS-PAGE for this separation is shown in FIG. 8 above. −50-1.0 min. fractions were collected from a separation of 1,350 μg of immunodepleted human serum and 5 representative fractions were selected for evaluation by LC/MS/MS (FIG. 11). Fractions 16 (1110), 20 (1120), 29 (1130) and 32 (1140) were selected for their different band patterns and MW distribution. Fraction 9 (1110), however, was selected for its content of lower molecular weight proteins.

EXAMPLES

The following examples serve to more fully describe the manner of using the above-described disclosure, as well as to set forth the best modes contemplated for carrying out various aspects of the disclosure. It is understood that these examples in no way serve to limit the true scope of this disclosure, but rather are presented for illustrative purposes.

Method A

Protein Separation with Removal of High Abundance Proteins

In an illustrative general procedure, samples of human serum that had been previously depleted of their six most abundant proteins, for example by immunodepletion methods, were separated under a variety of reversed-phase high pressure liquid chromatography (RP HPLC) conditions using a totally porous stationary phase designated 300SB-C8 or a superficially porous stationary phase designated mRP-C18. The depleted six-most-abundant proteins were albumin (about 54% by weight), immunoglobulin G (about 16%), alpha-1-antitrypsin (about 4%), immunoglobulin A (about 3.5%), transferrin (about 3%), and haptoglobin (about 3%). The less abundant protein faction balance totaled about 15 wt %.

The quality of the separations was determined by the electrophoretic gel patterns of the fractionated proteins. The RP HPLC column fractions were investigated by identifying proteins via tryptic fragmentation and peptide analysis using multidimensional LC/MS/MS. The conditions developed and evaluated for the less abundant protein separations permitted enhanced peak resolution and enabled high protein recoveries and increased column loads. In particular, use of particular superficially porous RP HPLC column materials operated at elevated temperatures, in combination with a multi-segment elution gradient provided enhanced peak selectivity, reduced band broadening, and improved protein recovery, while permitting robust and reproducible operation of the separation.

Example 1

Referring to the Figures, FIGS. 1A-1C demonstrate protein separations, recoveries and resolutions obtained by the method of the present disclosure compared to those obtained using an alternative porous stationary phase. Both separations were accomplished at an elevated temperature of 80° C. FIG. 1A shows the elution of protein sample components in quantity (mAU) versus time on a superficially porous C18 stationary phase, which provided a protein recovery or yield of about 92% (n=3). FIG. 1B shows the comparative elution of the same protein sample components on a 300SB-C8 phase, which provided a provided a protein recovery yield of about 62% (n=3). FIG. 1C shows the superposition of blank or baseline runs (free protein sample) for the stationary phase used in FIG. 1A (10) and for the stationary phase used in FIG. 1B (20).

The use of superficially porous packing materials in the present method, at elevated temperatures, provided significantly higher protein recoveries, for example by about 30 weight %. At 80° C. an injection of 85 micrograms of protein yielded 78 micrograms of total protein from the macroporous C18 column, compared to 53 micrograms recovered from the totally porous C8 column. The differences in protein carryover between the C18 and C8 columns were demonstrated by performing subsequent blank runs on each column at 80° C. The materials and conditions for the comparison were as follows.

Columns and Supports (stationary phase): superficially porous C18, 300SB-C8, 5.0 microns particle diameter, 4.6× 50 mm i.d., stainless steel.

Sample: 85 micrograms protein injected in 100 microliters of 6M urea/5% AcOH, at 0.75 mL/min, 80° C., DAD 280 nm.

Mobile phase: A-0.1% TFA/water, B-0.08% TFA/CAN.

Gradient conditions: 60-80% B in 2.7 min., 80% B for 3.3 min, 80-20% B in 3.0 min, 45 minutes runtime.

Example 2

FIGS. 2A-2B further illustrates protein separations, separation selectivities, and resolutions of the present method compared to an alternative method using an alternative stationary phase. Use of elevated temperature and the superficially porous C18 column packing material resulted in an increase in selectivity and resolution, and provided higher protein recoveries, such as demonstrated in Example 1. Comparison of the respective chromatograms at 80° C. for the superficially porous C18 stationary phase of FIG. 2A and the totally porous C8 stationary phase of FIG. 2B showed a loss in resolution for higher abundant protein complexes. For example in FIG. 2A an α-1-acid-glycoprotein (210) and a complement component C4 (220) were satisfactorily resolved whereas in FIG. 2B these components were not fully resolved. The materials and conditions for the comparison were as follows.

Columns and Supports: As in Example 1.

Sample: 135 micrograms protein injected in 6M urea/5% AcOH, 0.75 mL/min, DAD 280 nm, at 80° C.

Mobile phase: As in Example 1.

Gradient conditions: 5-30% B in 5 min, 30-55% B in 33 min., 55-100% B in 10 min; 100% B 4 min.

Method B

Protein Separation without Removal of High Abundance Proteins

Method B demonstrated application of protein separation techniques of the present invention to membrane-associated proteins. The methods described below utilize the same principles employed in Method A but without removal of high abundance proteins by immunoaffinity depletion. In embodiments, the protein sample for separation is a membrane sample isolated from a population of cells or a tissue. In further embodiments, the membrane sample included membrane lipid rafts.

In further illustration of the present invention, membrane samples including human membrane lipid rafts were separated under a variety of reversed-phase high pressure liquid chromatography (RP HPLC) conditions using a superficially porous stationary phase designated mRP-C18. The quality of the separations was determined by the electrophoretic gel patterns of the fractionated proteins. In particular embodiments, a superficially porous RP HPLC column materials were operated at elevated temperatures in combination with a multi-segment elution gradient which provided enhanced peak selectivity, reduced band broadening, and improved protein recovery, while permitting robust and reproducible operation of the separation.

Membrane Sample Preparation

Membrane samples for HPLC chromatographic separation according to the present methods may be isolated or enriched according to conventional methods. Generally, cells or tissue samples are collected and suspended in a suitable buffer. Tissue samples are homogenized and cells are lysed. Membrane samples (also referred to as "membrane fractions") are separated from soluble cellular components by centrifugation followed by phase partitioning. See, for example, Elortza et al. (2003) *Molecular and Cellular Proteomics* 2.12:1261; Nuhse et al. (2003) *Molecular and Cellular Proteomics* 2.11: 1234; Eichacker et al. (2004) *J. Biol. Chem.* 279:50915-50922; and Han et al. (2004) *J. Prot. Res.* 3:807-812, herein incorporated by reference. For example, HeLa cell membrane samples may be prepared according to Elortza by lysing HeLa cells in 100 mM $Na_2CO_3$, pH 11.0, followed by mechanically disruption. The lysates are clarified and combined with an equal volume of 90% sucrose in MES-buffered saline (MBS) (150 mM NaCl, 25 mM MES, pH 6.5) for a final sucrose concentration of 45%. This solution is then placed in the bottom of an ultracentrifuge tube as the base of a discontinuous sucrose gradient. Additional layers consisting of 35 and 5% sucrose in MBS are gently placed onto it, and the whole gradient is centrifuged at 166,000×g for 18 h at 4° C. The resulting low density light-scattering band (about 18% sucrose) is extracted, diluted 4× in $Na_2CO_3$, and centrifuged for a further 2 h (166,000×g, 4° C.) to pellet the membrane sample.

Example 3

Reversed-phase Liquid Chromatography

The membrane fractions, in the present example human brain membrane lipid rafts, were solubilized for HPLC according to an embodiment of the present invention by drying the membrane fraction sample in a speed vacuum. The dried sample was re-dissolved in a 2:1 v:v ratio of 80% formic acid:membrane fraction. The mixture was sonicated for 30 seconds and re-dried in a speed vacuum to dryness. The sample was resolubilized in a about 5:1 v:v ratio of 80% formic acid:membrane sample.

Figure 12:
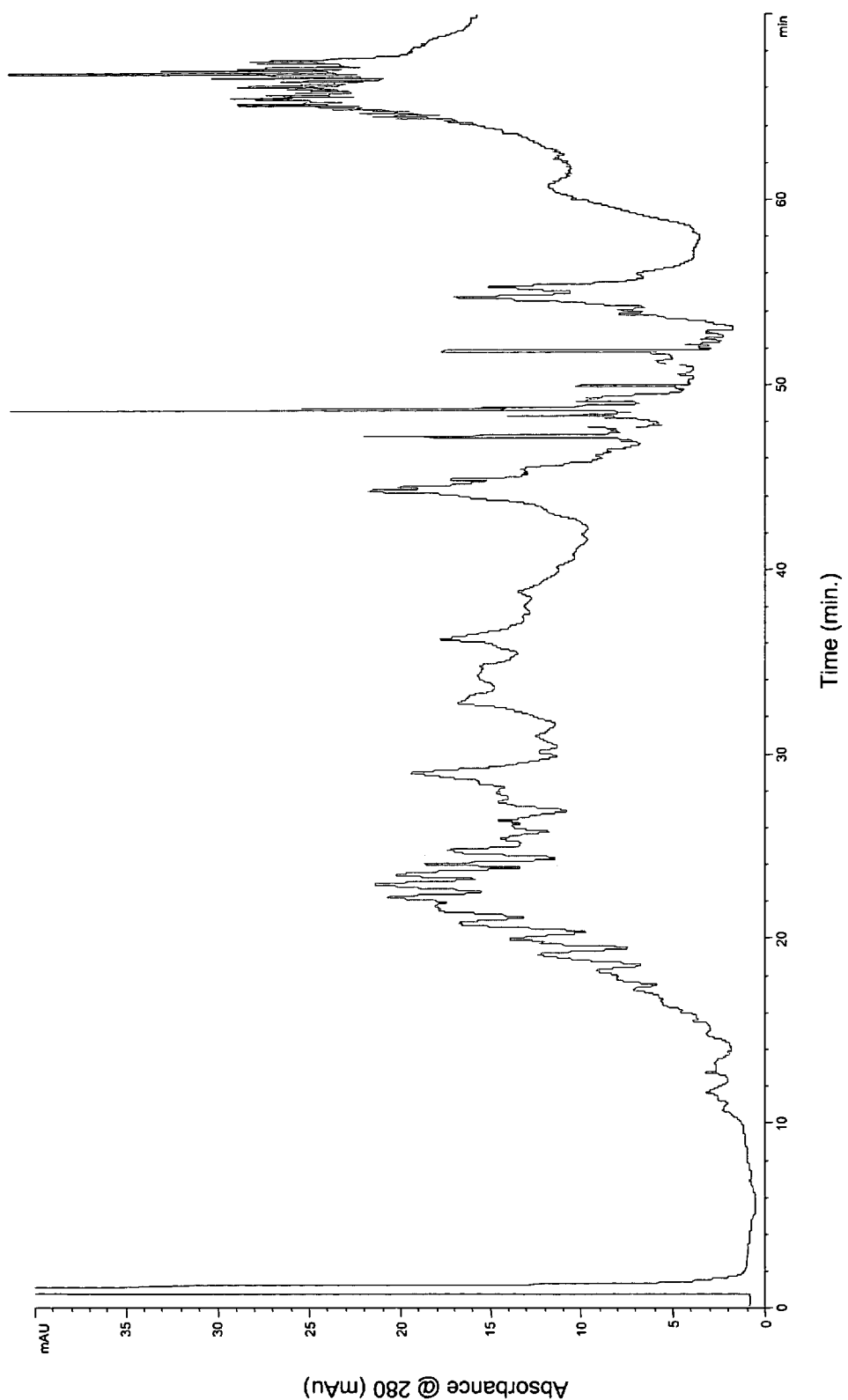
FIG. 12 illustrates a representative RP-HPLC elution profile of membrane lipid rafts on a superficially porous column in an embodiment of the present disclosure.
Figure 13:
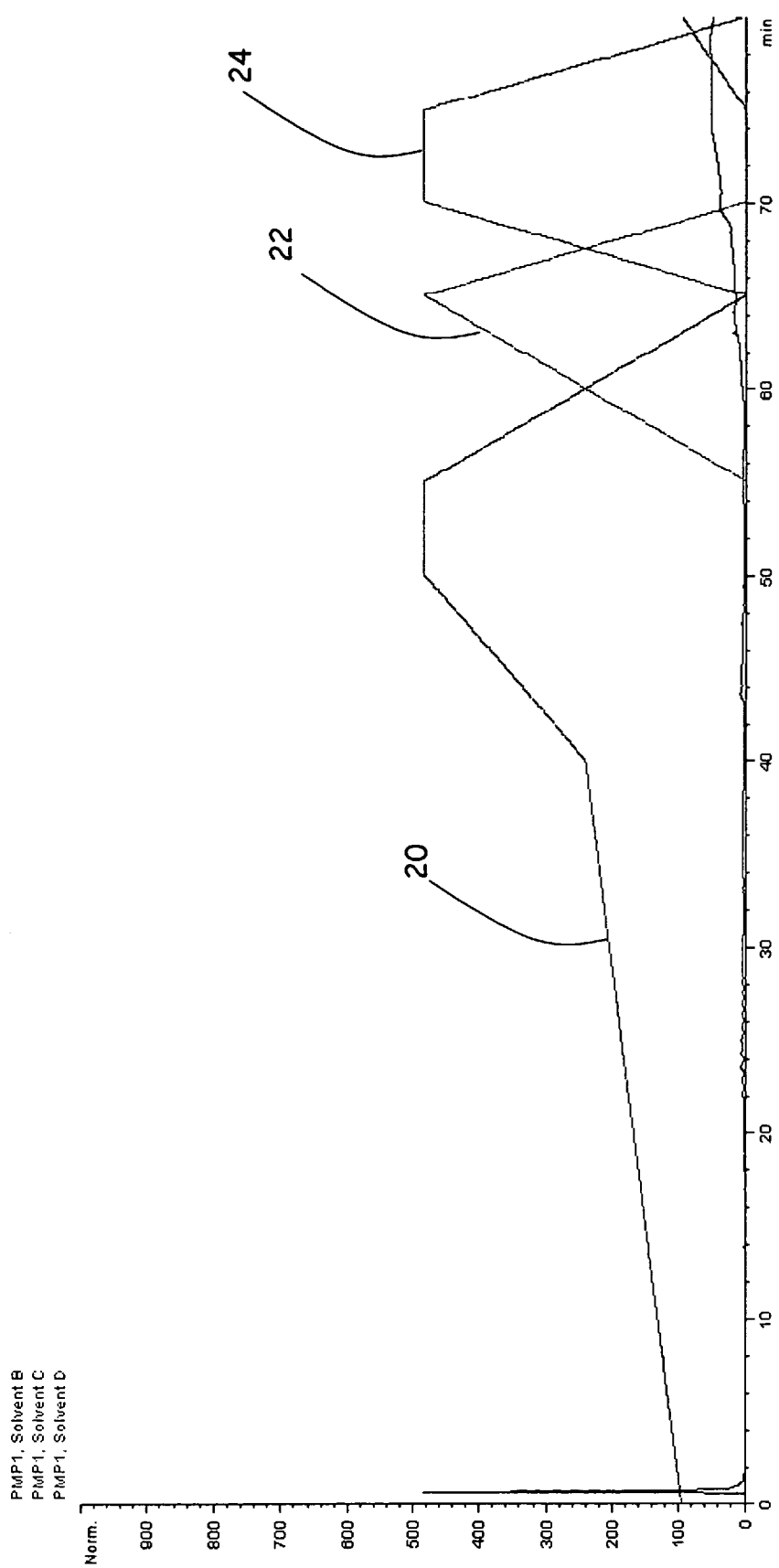
FIG. 13 illustrates a representative RP-HPLC step gradient elution conditions in an embodiment showing increasing concentrations of acetonitrile with TFA, followed by acetonitrile with formic acid, followed by isopropanol on a 4.6×50 mm superficially porous C18 column.

FIGS. 12-17 illustrate the chromatographic separation performed on human brain membrane lipid rafts using a multi-step gradient elution on a superficially porous C18 (4.6×50 mm) stationary phase. FIG. 12 illustrates a RP-HPLC elution profile at a wavelength of 280 nm that resulted for an embodiment of a separation human membrane lipid rafts. FIG. 13 illustrates representative RP-HPLC step gradient elution conditions with increasing concentrations of acetonitrile/TFA, actonitrile/formic acid, and isopropanol on a 4.6×50 mm superficially porous C18 column.

HPLC was performed on an automated Agilent 1100 LC system (Chemstation A.10.01 software) using standard configurations with operation at ambient and elevated temperatures. The LC station components included a quaternary pump, degasser, thermostated auto injector, diode-array detector (280 nm), column heater and analytical scale thermostat-controlled fraction collector. The LC system set-up allowed automated separations of multiple samples and fulfilled necessary requirements such as monitoring, precise fraction collection, injection and cooling of injected and collected samples. A reversed-phase 5.0 µm particle diameter superficially porous C18 resin was prepared and packed into, 4.6×50 mm PEEK HPLC column. In embodiments, alternative column sizes and alternative reversed-phase particle diameter and type may be used. For example, a 4.6×50 mm column has a fractionating capacity of up to about 500 µg protein and a 9.4×50 mm column afforded capacities in the range of 1,400-1,600 µg of protein.

In embodiments, the protein separation methods of the present disclosure can be accomplished using a superficially porous phase at elevated temperature and which elevated temperature can be maintained relatively uniform, that is substantially isothermally, throughout the superficially porous phase separation, such as at a temperature or temperature range as illustrated herein, and having a temperature variation of, for example, from about plus or minus 10° C., from about plus or minus 5° C., from about plus or minus 2.5° C., from about plus or minus 1.0° C., or from about plus or minus 0.5° C. In embodiments, the protein separation methods of the present disclosure are accomplished at elevated temperatures, for example 80° C. In embodiments, the RP-HPLC system can include, for example, a pressure restrictor, or like devices or apparatus that can prevent or minimize solvent(s) boil-off to maintain the performance characteristics of the mobile phase and the integrity of the separation method.

Approximately 500 µg in a volume of about 500 µL of lipid rafts was injected onto 4.6×50 mm superficially porous particle columns at 80° C. Separations were performed using a stepwise gradient elution, with buffer A: 0.1% TFA in water, buffer B: 0.08% TFA in acetonitrile, buffer C: 20% formic acid in acetonitrile, and buffer D: isopropyl alcohol. The elution profile that resulted from a representative separation of the membrane lipid rafts according to the present method is shown in FIG. 12. The step gradient consisted of six steps with increasing concentrations of buffer B in buffer A: 20-50% B 30 min., 50-100% B 10 min., hold 100% B 5 min, buffer B: 0-100% C 10 min., buffer C: 0-100% D 5 min., hold 100% D, 5 min., at a flow rate of 0.75 mL/min for a total runtime of 75.0 min. During consecutive runs, a 5.0 min. post run comprising of buffer A: 20.0% buffer B was added to re-equilibrate the column. The column eluent was collected into 50 mL polystyrene conical tubes. Blank runs were performed in the same manner, however, with the column removed from the flow path. The blanks were collected before and after the column recoveries. The chromatograms were monitored at 280 nm and 70 fractions collected at 1.0 min. intervals from 1.0-70.0 min. In an embodiment, fractions 1-10, 11-15, 16-20, 51-60, 51-60, and 61-70 were combined. Each fraction or combined fraction was dried in a speed vacuum concentrator and stored at −80° C. for LC/MS/MS and 1D SDS-PAGE analysis. Blanks and column eluates (approx. 50 mL) were dried in a speed vacuum concentrator at medium drying temperatures overnight.

Figure 14:
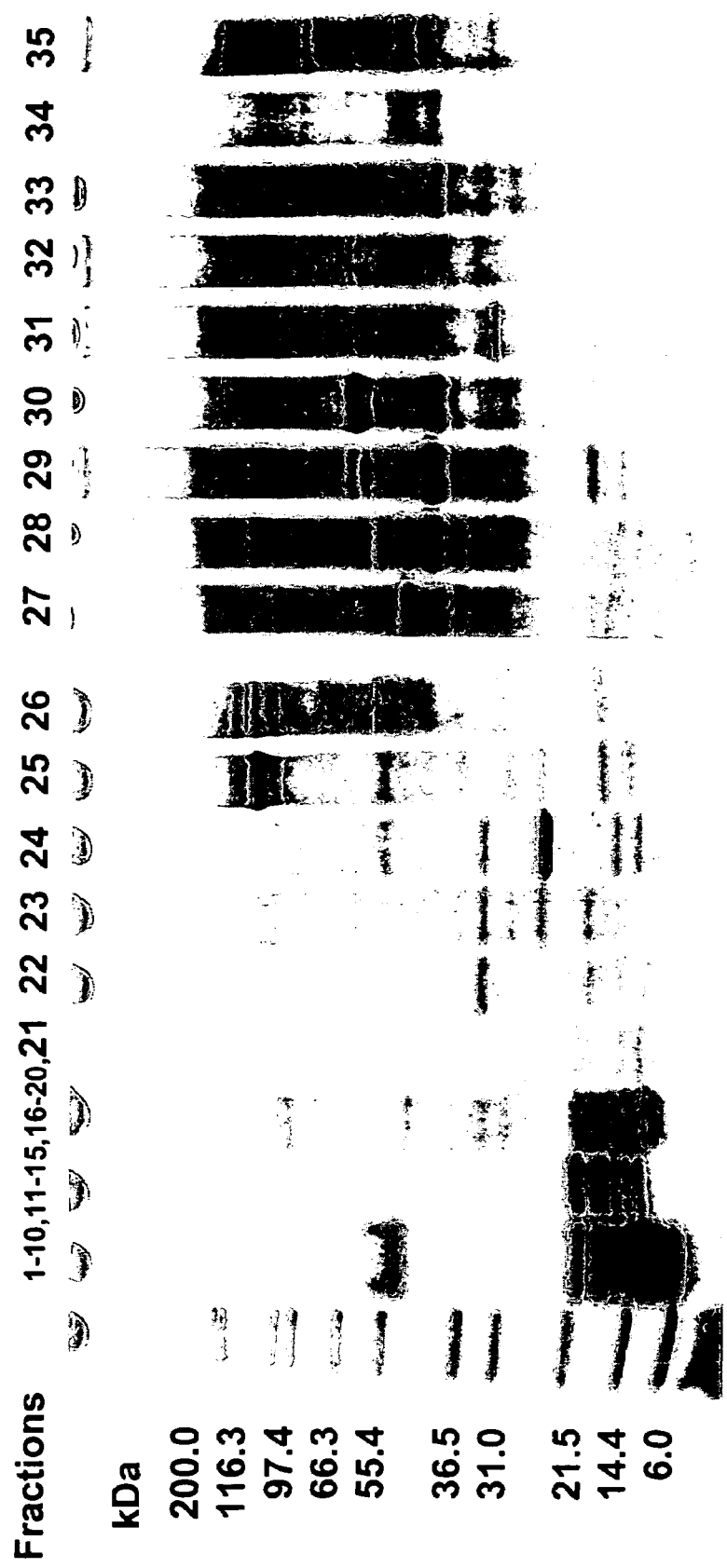
FIG. 14 illustrates an SDS-PAGE analysis of fractions 1-35 of HPLC fractionated membrane lipid rafts corresponding to the elution profile provided in FIG. 12.
Figure 15:
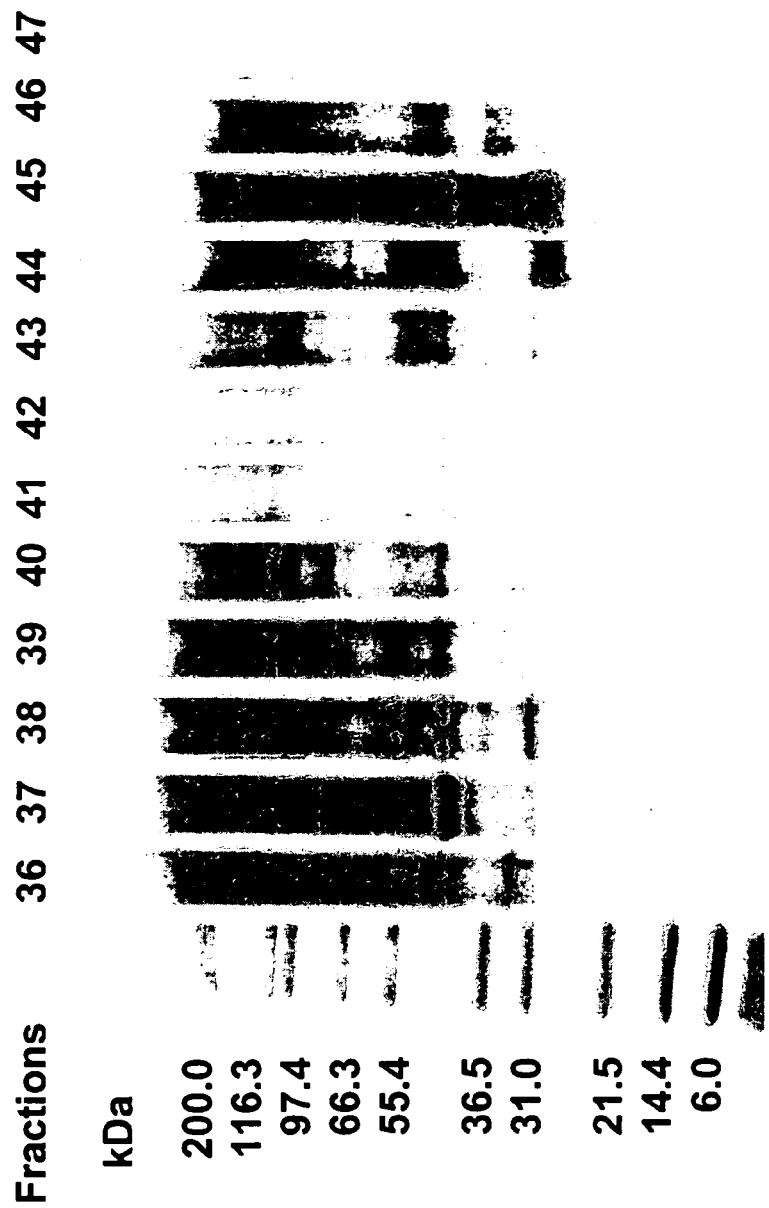
FIG. 15 illustrates SDS-PAGE analysis of fractions 36-47 of HPLC fractionated membrane lipid rafts corresponding to the elution profile provided in FIG. 12.

In addition, under the conditions disclosed above, the mRP-C18 column was evaluated for reproducibility. Multiple separations of human membrane lipid rafts were performed by collecting precise fraction slices from each run. FIG. 14 details results from five consecutively preformed human membrane lipid raft separations thereby having demonstrated the chromatographic reproducibility of the method. The UV trace at 280 nm showed no changes from run to run and the peak intensities remained identical and overlapping. In addition, there did not appear to be any shift in retention times for any of the peaks fine structure. FIG. 15 illustrates and compares results from the pre-run column blank and a post-run blank that were run before and after the 5 consecutive separations. The UV trace at 280 nm showed insignificant changes from pre to post-run indicating minimal residual contamination of the column.

Electrophoretic Analysis

1D SDS-PAGE analysis was carried out using Invitrogen Tris-glycine precast gels (4-20% acrylamide, 10 wells, 1 mm, #EC6025BOX) according to the manufacturer's protocol. Each fraction was resolubilized in 2×SDS loading buffer and heated to 65° C. for 1 min prior to loading. Proteins were visualized by Coomassie Blue staining with GelCode Blue (Pierce, #24592).

Figure 16:
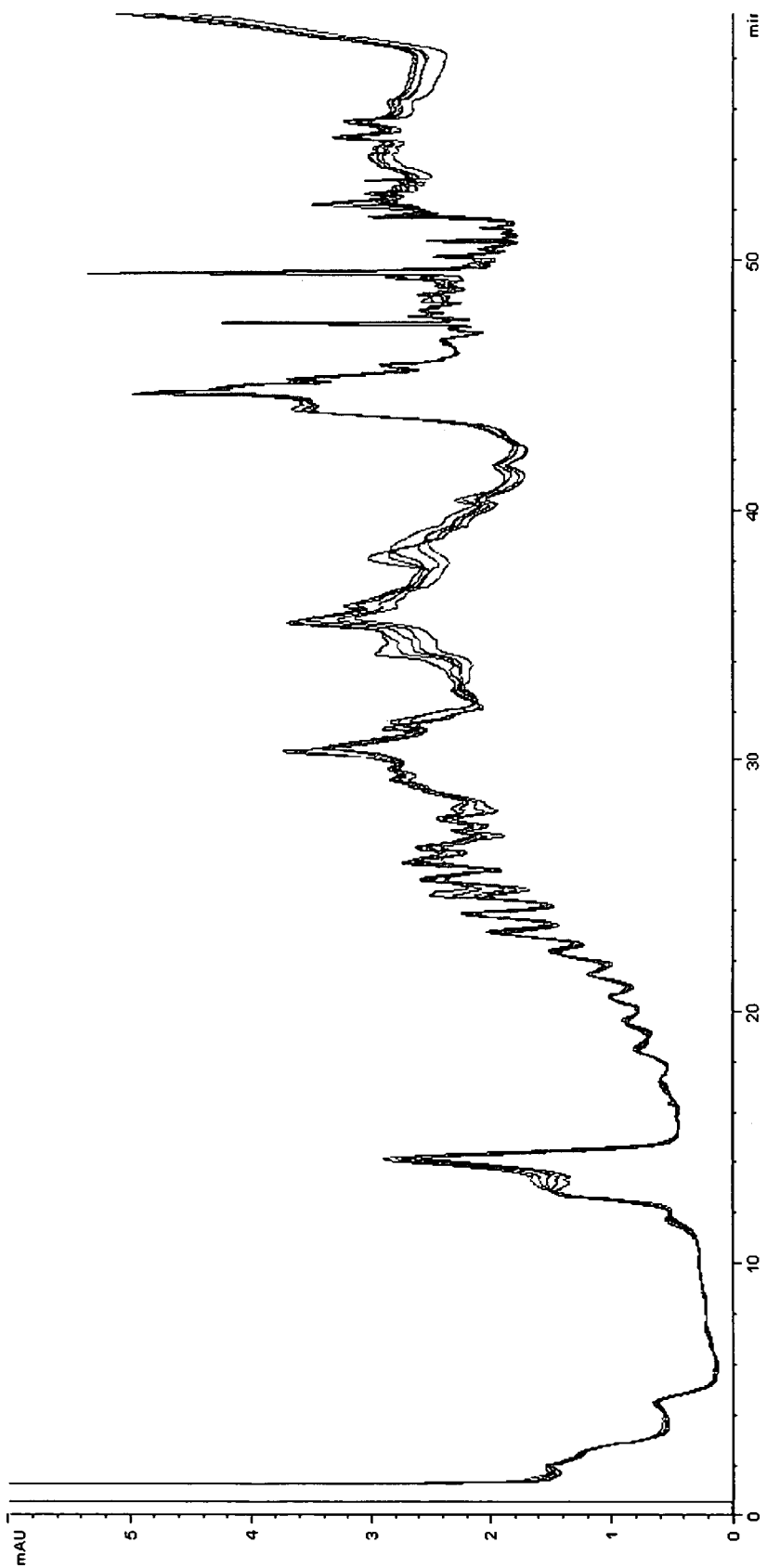
FIG. 16 illustrates a composite overlay of chromatograms from five reversed-phase separations of membrane lipid rafts on a superficially porous column, in embodiments of the present disclosure.
Figure 17:
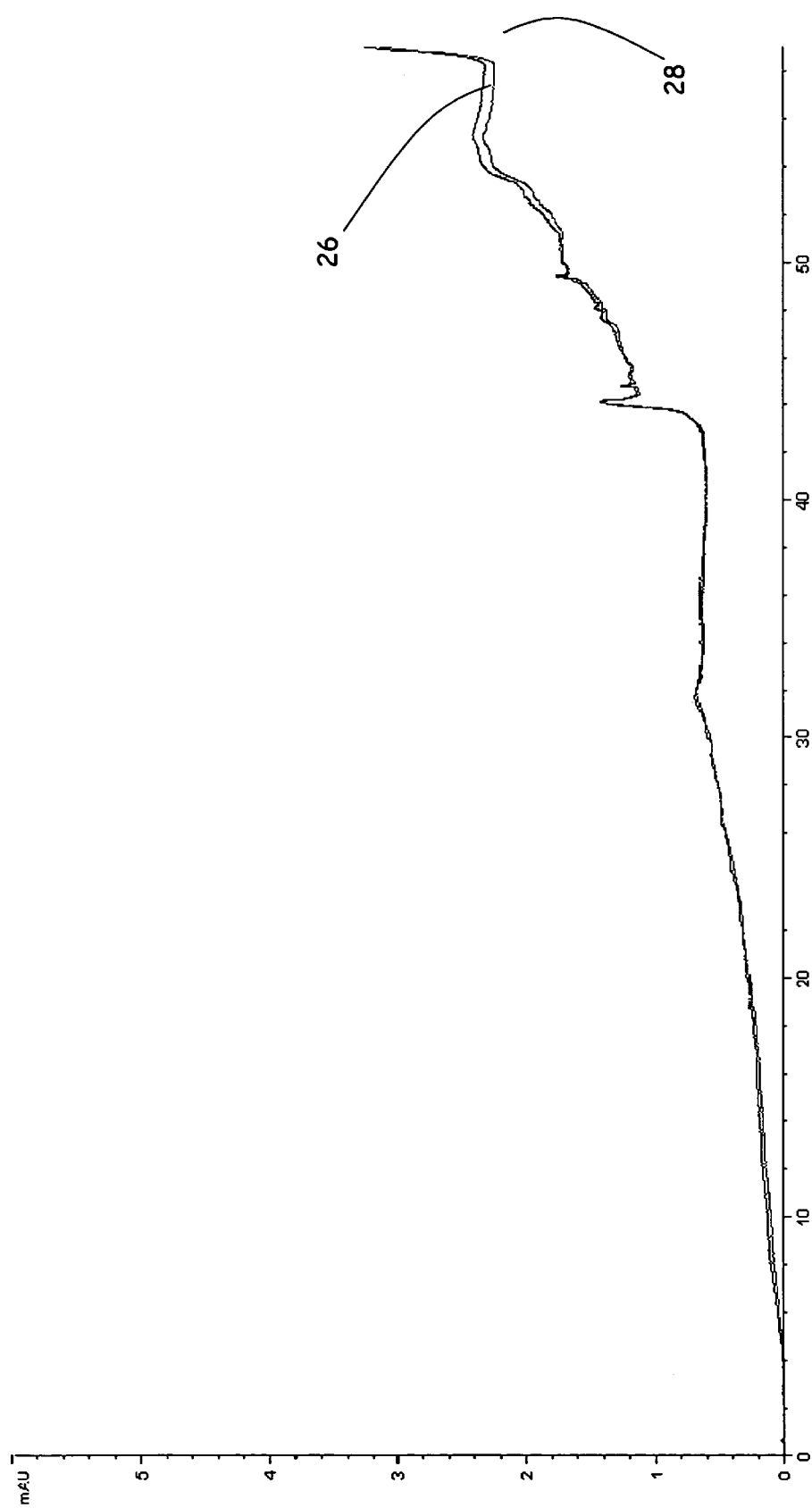
FIG. 17 illustrates a composite overlay of chromatograms from prerun and postrun fractions from the superficially porous column utilized in the five reversed phase separations of membrane lipid rafts shown in FIG. 16.

FIGS. 16 and 17 illustrate results achieved by HPLC fractionation of human membrane samples according to the above methods by SDS-PAGE analysis. The collected fractions were dried and dissolved in SDS sample buffer and loaded onto a 4-20% SDS-PAGE. Lane 1 represented the Invitrogen markers in kDa. Visualization of 1D gel patterns was used as another gauge to measure separation efficiency of the fractionated proteins. Examination of band patterns was used to determine the effectiveness, or ineffectiveness, of the separation based on band repetitions across gel lanes or lack thereof. Band intensities may also have given an indication of column capacities by the extent of their carryover from one lane to another.

Protein Recovery

One of the important attributes of a reliable, complex sample separation is the ability to recover injected material. Recovery values were normalized against sham injections (no column present), which were considered as 100% recovered.

Dried samples of column and blank runs were solubilized with 0.5 mL of 6M Urea, 1% Triton X-100 and 0.25% acetic acid. Samples were extensively vortexed to solubilize all protein and remove any material adhering to the tube walls. Samples were transferred to eppendorf tubes and sonicated in a water bath for 2 minutes. Protein quantitation was performed with BCA protein assay (Pierce). 50 µL of sample was mixed with d.i.$H_2O$ to a final volume of 100 µL and the protein assay performed according to manufacturer's suggested protocol.

Similar recovery results have been obtained using the EZQ Protein Quantitation kit (R 33200) from Invitrogen/Molecular Probes. An ovalbumin standard was used for the creation of a least-squares fitted standard curve. 1 µL of each sample was spotted on assay paper; the samples were fixed, washed and stained with EZQ stain according to the manufacturer's protocol. Each sample was then processed in quadruplicates and fluorescence was measured by scanning the paper on a Typhoon 8600 laser scanner (Amersham Biosciences, Piscataway, N.J.) using a 532 nm laser for the excitation and 580 nm emission filter.

As shown in Table 2, the reversed phase separations performed under elevated temperature, specifically 80° C., provided near quantitative recovery of the injected membrane lipid rafts.

TABLE 2

Protein recoveries from reversed phase separation.

| Separation Media | % Recovery, 80° C. |
|---|---|
| Superficially Porous C18 n = 4 | 113.8 ± 10.9 |

Example 4

Separation of HeLa Cell Membrane proteins according to protein separation methods of the present invention was also demonstrated. A HeLa Cell membrane sample was generally prepared and separated according to the methods provided in Example 3. The HeLa cell membrane sample was solubilized for HPLC according to an embodiment of the present invention by drying the membrane sample in a speed vacuum. The dried sample was re-dissolved in a 2:1 v:v ratio of 80% formic acid:membrane fraction. The mixture was sonicated for 30 seconds and re-dried in a speed vacuum to dryness. The sample was resolubilized in a about 5:1 v:v ratio of 80% formic acid:membrane sample and was subsequently loaded onto the column for separation.

Figure 18:
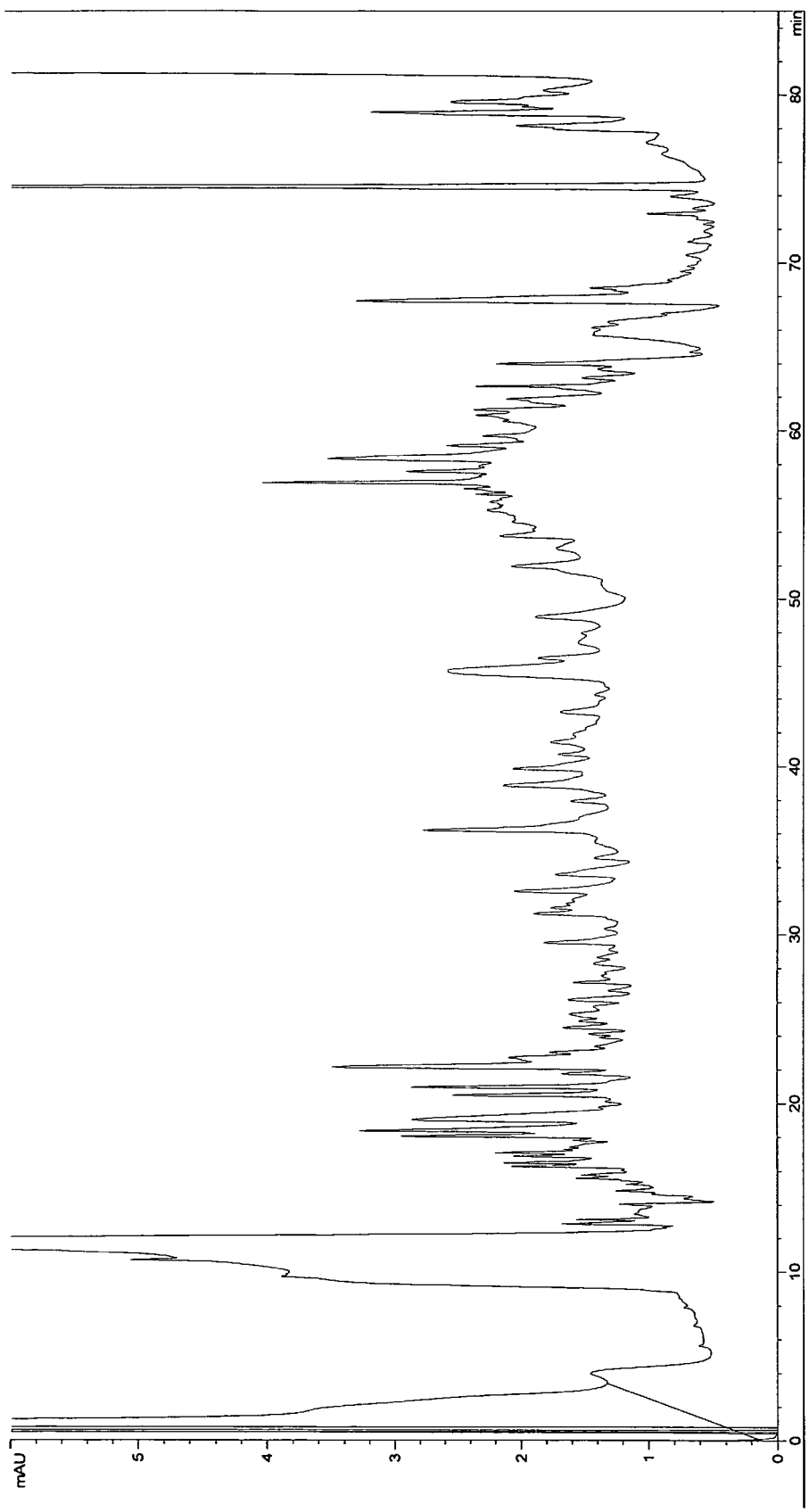
FIG. 18 illustrates illustrates a representative RP-HPLC elution profile of a HeLa cell membrane sample on a superficially porous column in an embodiment of the present disclosure.
Figure 19:
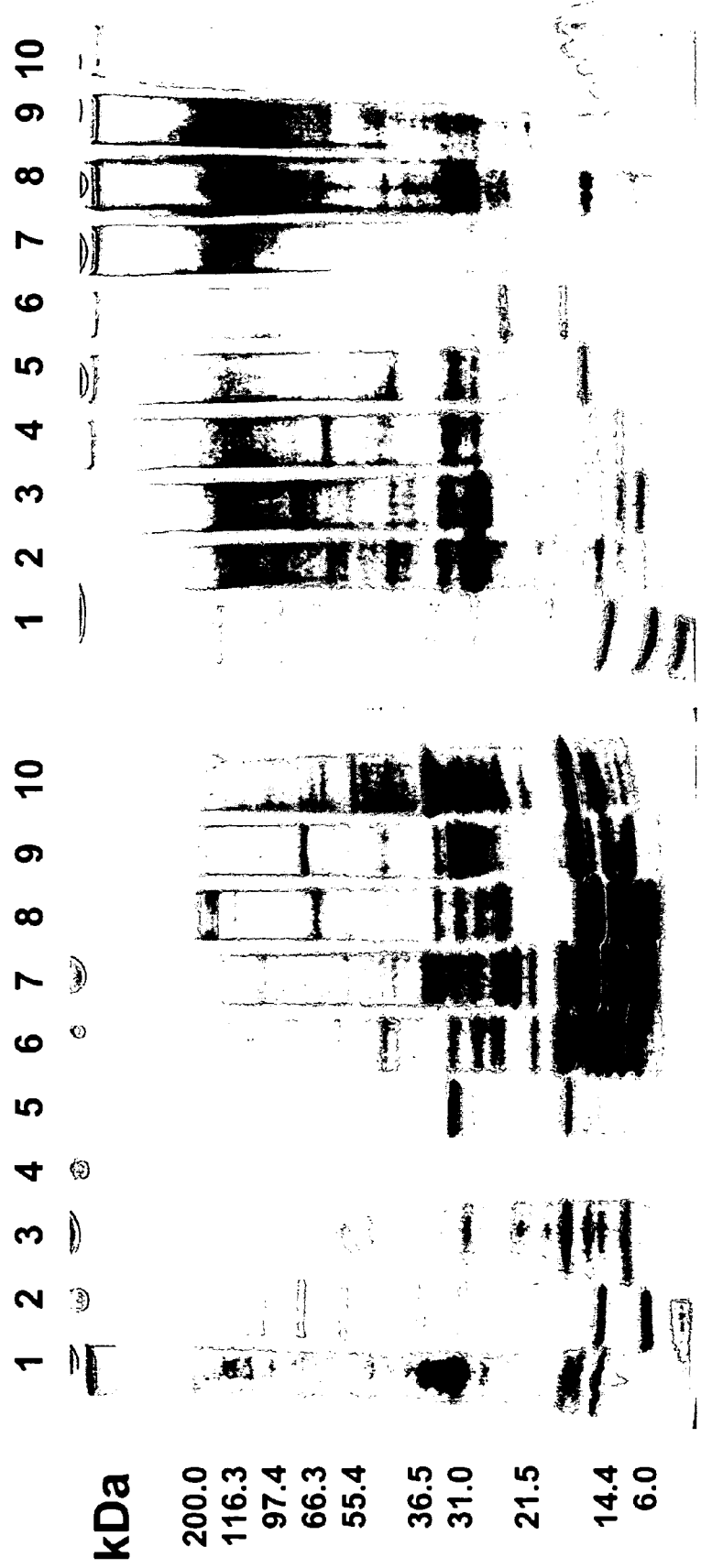
FIG. 19 illustrates SDS-PAGE analysis of fractions of an HPLC fractionated HeLa cell membrane sample corresponding to the elution profile provided in FIG. 18.

A 146 µg of HeLa cell membrane sample was separated on a 4.6 mm×50 mm mRP-C18 column. The gradient system and column parameters were as provided above. FIG. 18 illustrates a RP-HPLC elution profile at a wavelength of 280 nm for the separation of HeLa cell membrane sample. A second HPLC fractionation of 720 µg of HeLa membrane sample was performed on a 4.6×50 mm mRP-C18 column according to the methods provided above. The collected fractions were pooled as indicated in Table 3, dried, and dissolved in SDS sample buffer, and loaded onto a 4-20% SDS-PAGE. The results obtained from the SDS PAGE separation are illustrated in FIG. 19.

TABLE 3

| Gel 1 | Gel 2 |
|---|---|
| #1 Hela membranes, starting material, 22 µg | #1 Mark12 standards |
| #2 Mark12 standards | #2 Fractions 33-36 |
| #3 Fractions 1-4 | #3 Fractions 37-40 |
| #4 Fractions 5-8 | #4 Fractions 41-44 |
| #5 Fractions 9-12 | #5 Fractions 45-48 |
| #6 Fractions 13-16 | #6 Fractions 49-52 |
| #7 Fractions 17-20 | #7 Fractions 53-56 |
| #8 Fractions 21-24 | #8 Fractions 57-60 |
| #9 Fractions 25-28 | #9 Fractions 61-64 |
| #10 Fractions 29-32 | #10 Fractions 65-68 |

CONCLUSIONS

Similar to the results demonstrated by Method A, it was found that by completing the gradient with 100% acetonitrile, formic acid/ACN, and isopropanol and holding for a short period of time, it was possible to regenerate the column surface free of absorbed proteins and obtain recoveries to near quantitative values. No evidence of protein precipitation or protein loss from the membrane samples was observed. The combination of high temperatures, low mobile phase pH, and acetonitrile as an organic modifier, maintain all or most of the proteins' solubility, without any compromises to column stability for separation of membrane samples.

The entire disclosure for publications, patents, and patent documents are incorporated herein by reference, as though individually incorporated by reference. The disclosure has been described with reference to various specific embodiments and techniques. Additional aspects of the disclosure are additionally described in Appendix A and in the Figures provided therewith. However, it should be understood that many variations and modifications are possible while remaining within the spirit and scope of the disclosure.

REFERENCES

1. Agnew, B. J., D. Murray, and W. F. Patton, *A rapid solid-phasefluorescence-based protein assay for quantitation of protein electrophoresis samples containing detergents, chaotropes, dyes, and reducing agents*. Electrophoresis, 2004. 25(15): p. 2478-85.
2. Badock, V., et al., *Prefractionation of protein samples for proteome analysis using reversed-phase high-performance liquid chromatography*. Electrophoresis, 2001. 22(14): p. 2856-64.
3. Bhardwaj, S. and R. A. Day, *Techniques in Protein Chemistry VIII*. 1997: p. 469-480.
4. Bhardwaj, S. and R. A. Day, *Trifluoroethanol Removes Bound Proteins from Reversed-Phase Columns*. LC-GC, 1999. 17(4): p. 354-355.
5. Chen, Y., C. T. Mant, and R. S. Hodges, *Temperature selectivity effects in reversed-phase liquid chromatography due to conformation differences between helical and non-helical peptides*. J ChromatogrA, 2003. 1010(1): p. 45-61.
6. Chemokalskaya, E., et al., *Ultrafiltration for proteomic sample preparation*. Electrophoresis, 2004. 25(15): p. 2461-8.
7. Duan, X., et al., *A mouse serum two-dimensional gel map: Application to profiling burn injury and infection*. Electrophoresis, 2004. 25(17): p. 3055-65.

8. Fujii, K., et al., *Multidimensional protein profiling technology and its application to human plasma proteome*. J Proteome Res, 2004. 3(4): p. 712-8.
9. Jack, G. W., *Immunoaffinity Chromatography*. Mol. Biotech, 1994. 1: p. 59-86.
10. Janini, G. M., et al., *Two-dimensional liquid chromatography-capillary zone electrophoresis-sheathless electrospray ionization-mass spectrometry: evaluation for peptide analysis and protein identification*. Electrophoresis, 2004. 25(13): p. 1973-80.
11. Lee, H., et al., *Optimization of reversed-phase microcapillary liquid chromatography for quantitative proteomics*. J Chromatogr B Analyt Technol Biomed Life Sci, 2004. 803(1): p. 101-10.
12. Lee, W. C., Lee, K. H., *Applications of affinity chromatography in proteomics*. Anal BioChem, 2004. 324: p. 1-10.
13. Lescuyer, P., D. F. Hochstrasser, and J. C. Sanchez, *Comprehensive proteome analysis by chromatographic protein prefractionation*. Electrophoresis, 2004. 25(7-8): p. 1125-35.
14. Liu, H., R. G. Sadygov, and J. R. Yates, 3rd, *A model for random sampling and estimation of relative protein abundance in shotgun proteomics*. Anal Chem, 2004. 76(14): p. 4193-201.
15. Marshall, J., et al., *Human serum proteins pre-separated by electrophoresis or chromatography followed by tandem mass spectrometry*. J Proteome Res, 2004. 3(3): p. 364-82.
16. Moffatt, F., P. Senkans, and D. Ricketts, *Approaches towards the quantitative analysis of peptides and proteins by reversed-phase high-performance liquid chromatography in the absence of a pure reference sample*. J Chromatogr A, 2000. 891(2): p. 235-42.
17. Neverova, I. and J. E. Van Eyk, *Application of reversed phase high performance liquid chromatography for sub-proteomic analysis of cardiac muscle*. Proteomics, 2002. 2(1): p. 22-31.
18. Righetti, P. G., et al., *Prefractionation techniques in proteome analysis*. Proteomics, 2003. 3(8): p. 1397-407.
19. Rose, K., et al., *Industrial-scale proteomics: from liters of plasma to chemically synthesized proteins*. Proteomics, 2004. 4(7): p. 2125-50.
20. Szafranski, C., et al., *Enhancing Analytical Access to Low-abundant Proteins in the Human Plasma Proteome*. Pharmagenomics, 2004.
21. Tirumalai, R. S., et al., *Characterization of the low molecular weight human serum proteome*. Mol Cell Proteomics, 2003. 2(10): p. 1096-103.
22. Van den Bergh, G., et al., *Reversed-phase high-performance liquid chromatography prefractionation prior to two-dimensional difference gel electrophoresis and mass spectrometry identifies new differentially expressed proteins between striate cortex of kitten and adult cat*. Electrophoresis, 2003. 24(9): p. 1471-81.

The claimed invention is:

1. A method of membrane protein separation comprising:
fractionating a membrane sample on a reversed-phase superficially porous stationary phase at a temperature of greater than or equal to about 40° C. with a gradient comprising increasing amounts of aqueous trifluoroacetic acid in an organic solvent and alternating amounts of increasing and decreasing concentrations of formic acid in an organic solvent and alternating amounts of increasing and decreasing concentrations of an alcohol to recover greater than about 70 weight percent of the fractionated membrane sample.

2. The method according to claim 1, wherein the fractionating is accomplished at from about 60 to about 95° C. to recover greater than about 90 weight percent of the fractionated membrane sample.

3. The method according to claim 1, wherein the fractionating is accomplished at from about 60 to about 95° C. to recover greater than about 95 weight percent of the fractionated membrane sample.

4. The method according to claim 1, wherein the weight percent of the recovered membrane protein increases with increases in temperature.

5. The method according to claim 1, wherein the reversed-phase superficially porous stationary phase has an average particle diameter of about 2 to about 20 micrometers.

6. The method according to claim 1, wherein the reversed-phase comprises a $C_6$ to about $C_{30}$ hydrocarbon selected from the group consisting of alkane, substituted alkane, alkene, substituted alkene, aryl or substituted aryl, and combinations thereof.

7. The method according to claim 1, wherein the reversed-phase comprises a silane compound having a $C_{10}$ to about $C_{30}$ hydrocarbon.

8. The method according to claim 1, wherein the reversed-phase comprises a divalent silane having a structure:

$$-Si(R)(Me)-(CH2)_3-Si(R)(Me)-$$

wherein R is n-octadecyl group, n-tetradecyl group, or mixtures thereof, and Me is methyl.

9. The method according to claim 1, wherein the reversed-phase comprises a silane of the formula:

$$A-O-SiR_1R_2R_3$$

where R1, R2, and R3 are each independently alkane, substituted alkane, alkene, substituted alkene, aryl or substituted aryl; and A is a surface group of the substrate to which the silane is attached.

10. The method according to claim 1, wherein the membrane sample, prior to fractionating, is solubilized in an aqueous mixture of concentrated formic acid.

11. The method according to claim 1, wherein the mixture of proteins, prior to fractionating, is solubilized in a mixture of about 5:1 v:v of 80% formic acid :membrane sample.

12. The method according to claim 1, wherein the gradient is accomplished stepwise, linearly, or a combination thereof.

13. The method according to claim 1, wherein the organic solvent is acetonitrile.

14. The method according to claim 13, wherein the alcohol is isopropanol.

15. The method according to claim 1, wherein fractionating is accomplished with a mobile phase having time-varying mixtures of one or more of the following:
from about 0.01 to about 2 weight % trifluoroacetic acid in water,
from about 0.01 to about 2 weight % trifluoroacetic acid in acetonitrile,
from about 5 to about 50 weight % formic acid in acetonitrile,
about 100 weight % isopropanol, and combinations or mixtures thereof.

16. The method according to claim 1, wherein the membrane sample is eluted with a gradient comprised of:
about 80% weight percent of about 0.01 to about 2 weight % trifluoroacetic acid in water and about 20 weight % of about 0.01 to about 2 weight % trifluoroacetic acid in acetonitrile with addition over time of:

from about 20 to about 50 weight % of about 0.01 to about 2 weight % trifluoroacetic acid in acetonitrile, in about 1 to 50 minutes;

from about 50 to about 100 weight % of about 0.01 to about 2 weight % trifluoroacetic acid in acetonitrile, in about 1 to 20 minutes;

from about 0 to about 100 weight % of about 5 to about 50 weight % formic acid in acetonitrile, in about 1-20 minutes; and from about 0 to 100 weight % of about 100% weight isopropanol, in about 1 to 20 minutes.

17. The method according to claim 1, wherein the load of membrane sample on the stationary phase is from about 100 micrograms to about 2 grams.

18. The method according to claim 1, further comprising separating each fractionated protein.

19. The method according to claim 18 further comprising analyzing at least one of the separated membrane proteins.

* * * * *